US008993573B2

(12) United States Patent
Ciufolini et al.

(10) Patent No.: US 8,993,573 B2
(45) Date of Patent: *Mar. 31, 2015

(54) 2-(3-AMINOARYL) AMINO-4-ARYL-THIAZOLES AND THEIR USE AS C-KIT INHIBITORS

(71) Applicant: AB Science, Paris (FR)

(72) Inventors: Marco Ciufolini, Vancouver (CA); Camille Wermuth, Srasbourg (FR); Bruno Giethlen, Altofr (FR); Alain Moussy, Paris (FR)

(73) Assignee: AB Science, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/089,946

(22) Filed: Nov. 26, 2013

(65) Prior Publication Data
US 2014/0088108 A1 Mar. 27, 2014

Related U.S. Application Data

(63) Continuation of application No. 13/015,664, filed on Jan. 28, 2011, now Pat. No. 8,835,435, which is a continuation of application No. 11/779,633, filed on Jul. 18, 2007, now abandoned, which is a continuation of application No. 10/523,018, filed as application No. PCT/IB03/03685 on Jul. 31, 2003, now abandoned, and a continuation of application No. 10/632,101, filed on Aug. 1, 2003, now Pat. No. 7,423,055.

(60) Provisional application No. 60/400,064, filed on Aug. 2, 2002.

(51) Int. Cl.
C07D 417/04 (2006.01)
C07D 277/42 (2006.01)
C07D 417/14 (2006.01)
C07D 277/56 (2006.01)

(52) U.S. Cl.
CPC ............ C07D 417/04 (2013.01); C07D 277/42 (2013.01); C07D 277/56 (2013.01); C07D 417/14 (2013.01)
USPC ................... 514/252.19; 514/236.8; 514/342

(58) Field of Classification Search
CPC .. C07D 417/04; C07D 277/42; C07D 417/14; C07D 277/56
See application file for complete search history.

(56) References Cited

U.S. PATENT DOCUMENTS

| | | | |
|---|---|---|---|
| 3,192,225 A | 6/1965 | Spivak et al. | |
| 3,201,409 A | 8/1965 | Dexter et al. | |
| 3,467,666 A | 9/1969 | Dexter et al. | |
| 3,740,420 A | 6/1973 | Herschler et al. | |
| 3,743,727 A | 7/1973 | Herschler | |
| 3,772,295 A | 11/1973 | Robba et al. | |
| 3,989,816 A | 11/1976 | Rajadhyaksha | |
| 4,322,433 A | 3/1982 | Leslie et al. | |
| 4,343,940 A | 8/1982 | Kreighbaum et al. | |
| 4,379,454 A | 4/1983 | Campbell et al. | |
| 4,405,616 A | 9/1983 | Rajadhyaksha | |
| 4,411,893 A | 10/1983 | Johnson | |
| 4,460,372 A | 7/1984 | Campbell et al. | |
| 4,540,269 A | 9/1985 | Nishiyama | |
| 4,575,515 A | 3/1986 | Sandborn | |
| 4,615,699 A | 10/1986 | Gale et al. | |
| 5,217,999 A | 6/1993 | Levitzki et al. | |
| 5,302,606 A | 4/1994 | Spada et al. | |
| 5,330,992 A | 7/1994 | Eissenstat et al. | |
| 5,521,184 A | 5/1996 | Zimmerman | |
| 5,556,611 A | 9/1996 | Biesalski | |
| 5,656,643 A | 8/1997 | Spada et al. | |
| 5,682,252 A | 10/1997 | Ando | |
| 5,710,158 A | 1/1998 | Myers et al. | |
| 5,714,493 A | 2/1998 | Myers et al. | |
| 5,721,237 A | 2/1998 | Myers et al. | |
| 5,776,020 A | 7/1998 | Barone | |
| 5,792,783 A | 8/1998 | Tang et al. | |
| 5,834,504 A | 11/1998 | Tang et al. | |
| 5,883,113 A | 3/1999 | Tang et al. | |
| 5,883,116 A | 3/1999 | Tang et al. | |
| 5,886,020 A | 3/1999 | Tang et al. | |
| 5,906,202 A | 5/1999 | Schuster et al. | |
| 6,239,172 B1 * | 5/2001 | Kaesemeyer | 514/460 |
| 6,291,514 B1 | 9/2001 | Illig et al. | |
| 6,697,600 B2 | 2/2004 | Nishikino et al. | |
| 6,892,245 B1 | 5/2005 | Shishido | |
| 7,423,055 B2 * | 9/2008 | Ciufolini et al. | 514/342 |

(Continued)

FOREIGN PATENT DOCUMENTS

EP 0 602 851 10/1996
EP 0 520 722 12/1996

(Continued)

OTHER PUBLICATIONS

U.S. Appl. No. 60/359,652, filed Feb. 27, 2002, Moussy et al.
U.S. Appl. No. 60/359,651, filed Feb. 27, 2002, Moussy et al.
Golub et al., Science, vol. 286, Oct. 15, 1999, pp. 531-537.
Schantl et al., Synthetic Communications, 1998, 29(8): 1451-1462.
Kim et al., "Inhibition of vascular endothelial growth factor-induced angiogenesis suppresses tumour grown in vivo", Nature, vol. 362, pp. 841-844, Apr. 29, 1993.
Nairn et al., "Solutions, Emulsions, Suspensions and Extractives", Remington's Pharmaceutical Sciences, 16$^{th}$ edition, pp. 1438-1462, 1980.
Dugard et al., "Effects of Ionic Surfactants on Permeability of Human Epidermis: An Electrometric Study", The Journal of Investigative Dermatology, vol. 60, No. 5, pp. 263-269, 1973.

(Continued)

Primary Examiner — Anna Pagonakis
(74) Attorney, Agent, or Firm — Clark & Brody

(57) ABSTRACT

Novel compounds selected from 2-(3-aminoaryl)amino-4-aryl-thiazoles of formula (I) that selectively modulate, regulate, and/or inhibit signal transductions mediated by certain native and/or mutant tyrosine kinases implicated in a variety of human and animal diseases such as cell proliferative metabolic, allergic and degenerative disorders. More particularly, these compounds are potent and selective c-kit inhibitors.

10 Claims, 2 Drawing Sheets

(56) References Cited

U.S. PATENT DOCUMENTS

Figure 1:
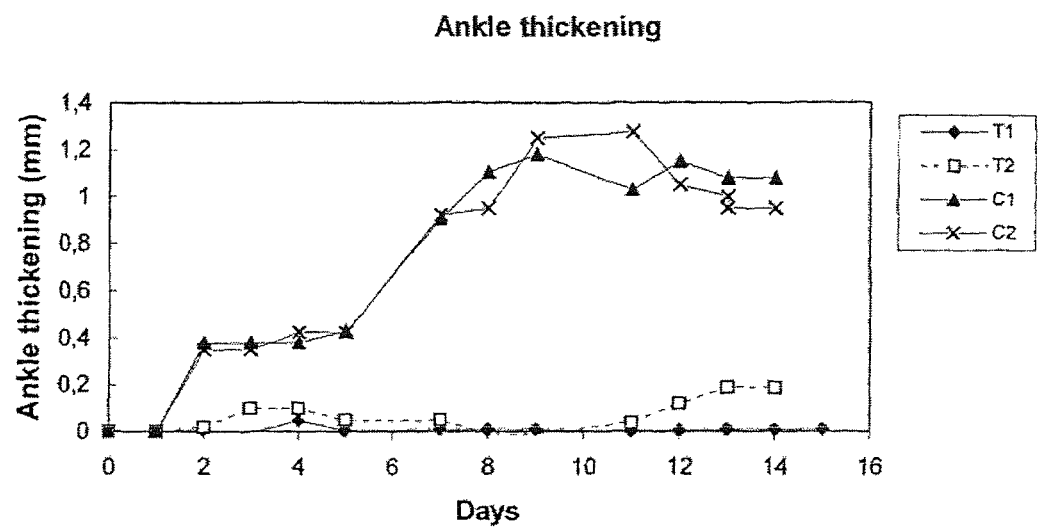

| | | |
|---|---|---|
| 2001/0044545 A1 | 11/2001 | Dhanoa et al. |
| 2003/0158199 A1 | 8/2003 | Stieber et al. |
| 2004/0110801 A1 | 6/2004 | Ciufolini et al. |
| 2004/0110810 A1 | 6/2004 | Ciufolini |
| 2012/0053186 A1 | 3/2012 | Ciufolini et al. |

FOREIGN PATENT DOCUMENTS

| | | |
|---|---|---|
| EP | 0 584 222 | 10/1997 |
| EP | 0 934 931 | 8/1999 |
| JP | 63-136462 | 9/1988 |
| JP | 63-028447 | 12/1996 |
| JP | 2002-185796 | 6/2002 |
| JP | 2003-134307 | 5/2003 |
| JP | 4333676 | 11/2004 |
| WO | 91/15495 | 10/1991 |
| WO | 92/20642 | 11/1992 |
| WO | 92/21660 | 12/1992 |
| WO | 94/03427 | 2/1994 |
| WO | 94/14808 | 7/1994 |
| WO | 95/15758 | 6/1995 |
| WO | 96/01825 | 9/1996 |
| WO | 96/40116 | 12/1996 |
| WO | 99/03854 | 1/1999 |
| WO | 00/33842 | 5/2000 |
| WO | 00/38519 | 7/2000 |
| WO | 00/75120 | 12/2000 |
| WO | 01/64200 | 9/2001 |
| WO | 01/64674 | 9/2001 |
| WO | 02/080925 | 10/2002 |
| WO | 03/002105 | 1/2003 |
| WO | 03/002106 | 1/2003 |
| WO | 03/002107 | 1/2003 |
| WO | 03/002108 | 1/2003 |
| WO | 03/002109 | 1/2003 |
| WO | 03/002114 | 1/2003 |
| WO | 03/003004 | 1/2003 |
| WO | 03/003006 | 1/2003 |
| WO | 03/004006 | 1/2003 |
| WO | 03/004007 | 1/2003 |
| WO | 03/035049 | 5/2003 |
| WO | 03/035050 | 5/2003 |
| WO | 03/039550 | 5/2003 |
| WO | 03/062215 | 7/2003 |
| WO | 2008/098949 | 8/2008 |

OTHER PUBLICATIONS

Sekura et al., "The Percutaneous Absorption of Alkyl Methyl Sulfoxides", Pharmacology of the Skin, Advances in Biology of Skin, vol. 60, pp. 257-269, 1972.

Cooper et al., "Interaction of Surfactants with Epidermal Tissues: Physicochemical Aspects", Surfactant Science Series, vol. 16, pp. 195-210, 1987.

Beslu et al., "Phosphatidylinositol-3[1] Kinase is Not Required for Mitogenesis or Internalization of the Flt3/Flk2 Receptor Tyrosine Kinase", The Journal of Biological Chemistry, vol. 271, No. 33, pp. 20075-20081, Aug. 16, 1996.

Rottapel et al., "The Steel/W Transduction Pathway: Kit Autophosphorylation and Its Association with a Unique Subset of Cytoplasmic Signaling Proteins is induced by the Steel Factor", Molecular and Cellular Biology, vol. 11, No. 6, pp. 3043-3051, Jun. 1991.

Choi et al., "Correlation of Computed Tomography and Positron Emission Tomography in Patients With Metastatic Gastrointestinal Stromal Tumor Treated at a Single Institution With Imatinib Meylate: Proposal of New Computer Tomography Response Criteria", Journal of Clinical Oncology, vol. 25, No. 13, May 1, 2007, pp. 1753-1759.

Darzynkiewicz et al., "Features of Apoptotic Cells Measured by Flow Cytometry", Cyometry, 13:795-808 (1992).

Therasse et al., "New Guidelines to Evaluate the Response to Treatment in Solid Tumors", Journal of the National Cancer Institute, vol. 92, No. 3, Feb. 2, 2000, pp. 205-216.

Jager et al., "Imatinib mesylate for the treatment of gastrointestinal stromal tumours: best monitored with FDG PET", Nuclear Medicine Communications, 2004, vol. 25, No. 5, pp. 433-438.

Demetri et al., "Efficacy and Safety of Imatinib Mesylate in Advanced Gastrointestinal Stromal Tumors", N Engl J Med, vol. 347, No. 7, Aug. 15, 2002, pp. 472-480.

Verweij et al., "Progression-free survival in gastrointestinal stromal tumours with high-dose imatinib: randomized trial", The Lancet, vol. 364, Sep. 25, 2004, pp. 1127-1134.

Blanke et al., Phase III Randomized, Intergroup Trial Assessing Imatinib Mesylate at Two Dose Levels in Patients With Unresectable or Metastatic Gastrointestinal Stromal Tumors Expressing the Kit Receptor Tyrosine Kinase: S0033, Journal of Clinical Oncology, vol. 26, No. 4, Feb. 1, 2008, pp. 626-632.

Blay et al., "Prospective Multicentric Randomized Phase III Study of Imatinib in Patients With Advanced Gastrointestinal Stromal Tumors Comparing Interruption Versus Continuation of Treatment Beyond 1 Year: The French Sarcoma Group", Journal of Clinical Oncology, vol. 25, No. 9, Mar. 20, 2007, pp. 1107-1113.

Heinrich et al., "Molecular Correlates of Imatinib Resistance in Gastrointestinal Stromal Tumors", Journal of Clinical Oncology, vol. 24, No. 29, Oct. 10, 2006, pp. 4764-4774.

Van Glabbeke et al., "Initial and Late Resistance to Imatinib in Advanced Gastrointestinal Stromal Tumors Are Predicted by Different Prognostic Factors: A European Organisation for Research and Treatment of Cancer-Italian Sarcoma Group-Australasian Gastrointestinal Trials Group Study", Journal of Clinical Oncology, vol. 23, No. 24, Aug. 20, 2005, pp. 5795-5803.

Blay et al., "Consensus meeting for the management of gastrointestinal stromal tumors, Report of the GIST Consensus Conference of Mar. 20-21, 2004, under the auspices of ESMO", Annals of Oncology 16: 566-578, 2005.

Debeic-Rychter et al., "KIT mutations and dose selection for imatinib in patients with advanced gastrointestinal stromal tumors", European Journal of Cancer 42 (2006) 1093-1103.

Van Glabbeke et al., "Comparison of two doses of imatinib for the treatment of unresectable or metastatic gastrointestinal stromal tumors (GIST): A meta-analysis based on 1,640 patents (pts).", American Society of Clinical Oncology, 2007 ASCO Annual Meeting Proceedings Part 1. vol. 25, No. 18S (Jun. 20 Supplement), 2007: 10004.

Zalcberg et al., "Outcome of patients with advanced gastro-intestinal stromal tumours crossing over to a daily imatinib dose of 800 mg after progression on 400 mg", European Journal of Cancer 41 (2005) 1751-1757.

Soria et al., "Phase 1 dose-escalation study of oral tyrosine kinase inhibitor masitinib in advanced and/or metastatic solid cancers", European Journal of Cancer 45 (2009) 2333-2341.

Tebib et al., "Masitinib in the treatment of active rheumatoid arthritis: results of a multicentre, open-label, dose-ranging, phase 2a study", Arthritis Research & Therapy, 2009, vol. 11, No. 3, pp. 1-12.

Van Glabbeke et al., "Predicting toxicities for patients with advanced gastrointestinal stromal tumours treated with imatinib: A study of the European Organisation for Research and Treatment of Cancer, the Italian Sarcoma Group, and the Australasian Gastro-Intestinal Trials Group", European Journal of Cancer 42 (2006) 2277-2285.

Lassau et al., "Gastrointestinal Stromal Tumors Treated with Imatinib: Monitoring Response with Contrast-Enhanced Sonography", Gastrointestinal Imaging, Nov. 2006, pp. 1267-1273.

Prior et al., "Early Prediction of Response to Sunitinib After Imatinib Failure by [18]F-Flourodeoxyglucose Positron Emission Tomography in Patients With Gastrointestinal Stromal Tumor", Journal of Clinical Oncology, vol. 27, No. 3, Jan. 20, 2009 pp. 439-445.

Van Den Abbeele et al., "Use of positron emission tomography in oncology and its potential role to assess response to imatinib mesylate therapy in gastrointestinal stromal tumors (GISTs)", European Journal of Cancer, vol. 38 Suppl. 5 (2002) S60-S65.

Chami et al., "Quantitative functional imaging by dynamic contrast enhanced ultrsonography (DCE-US) in patients with GIST treated by thyrosine kinase inhibitor (TKI)", J Clin Oncol 26: 2008 (May 20 suppl; abstr 10552).

(56) References Cited

OTHER PUBLICATIONS

Benjamin et al., "We Should Desist Using RECIST, at Least in GIST", Journal of Clinical Oncology, vol. 25, No. 13, May 1, 2007, pp. 1760-1764.
Le Cesne et al., "Absence of Progression as Assessed by Response Evaluation Criteria in Solid Tumors Predicts Survival in Advanced GI Stromal Tumors Treated With Imatinib Mesylate: The Intergroup EORTC-ISG-AGITG Phase III Trial", Journal of Clinical Oncology, vol. 27, No. 24, Aug. 20, 2009 pp. 3969-3974.
Demetri et al., "Efficacy and safety of sunitinib in patients with advanced gastrointestinal stromal tumour after failure of imatinib: a radomised controlled trial", The Lancet, vol. 368, Oct. 14, 2006, pp. 1329-1337.
Siesser et al., "The Signaling and Biological Implications of FAK Overexpression in Cancer", Clinical Cancer Research, Jun. 1, 2006, pp. 3233-3237.
Kindblom et al., "Gastrointestinal Pacemaker Cell Tumor (GIPACT), Gastrointestinal Stromal Tumors Show Phenotypic Characteristics of the Interstitial Cells of Cajal", American Journal of Pathology, vol. 152, No. 5, May 1998, pp. 1259-1269.
Hirota et al. "Gain-of-Function Mutations of c-kit in Human Gastrointestinal Stromal Tumors" Science, vol. 279, Jan. 23, 1998, pp. 577-580.
Heinrich et al., "PDGFRA Activating Mutations in Gastrointestinal Stromal Tumors", Science, Jan. 31, 2003, vol. 299, pp. 708-710.
Sleijfer et al., "Improved Insight into Resistance Mechanisms to Imatinib in Gastrointestinal Stromal Tumors: A Basis for Novel Approaches and Individualization of Treatment", The Oncologist, 2007; 12: 719-726.
Blanke et al., "Long-Term Results From a Randomized Phase II Trial of Standard-Versus Higher-Dose Imatinib Mesylate for Patients With Unresectable or Metastatic Gastrointestinal Stromal Tumors Expressing KIT", Journal of Clinical Oncology, vol. 26, No. 4, Feb. 1, 2008, pp. 620-625.
Demetri et al., "Imatinib Plasma Levels Are Correlated With Clinical Benefit in Patients With Unresectable/Metastatic Gastrointestinal Stromal Tumors", Journal of Clinical Oncology, vol. 27, No. 19, Jul. 1, 2009, pp. 3141-3147.
Dubreuil et al., "Masitinib (AB1010), a Potent and Selective Tyrosine Kinase Inhibitor Targeting KIT", PLoS ONE, Sep. 2009, vol. 4, Issue 9, pp. 1-12.
Abbott NJ. Inflammatory mediators and modulation of blood-brain barrier permeability. Cell Mol Neurobiol. Apr. 2000;20(2):131-47.
Adenis A. Masitinib mesylate in imatinib-resistant advanced GIST: A randomized phase II trial. Oral Abstract Session, 2012. 10007.
Aggarwal BB, Schwarz L, Hogan ME, Rando RF. Triple helix-forming oligodeoxyribonucleotides targeted to the human tumor necrosis factor (TNF) gene inhibit TNF production and block the TNF-dependent growth of human glioblastoma tumor cells. Cancer Res 1996;56(22):5156-64.
Aggarwal BB, Shishodia S, Sandur SK, Pandey MK, Sethi G. Inflammation and cancer: How hot is the link? Biochemical Pharmacology 2006: 72: 1605-1621.
Akiyama H, Barger S, Barnum S, Bradt B, Bauer J, Cole GM, Cooper NR, et al. Inflammation and Alzheimer's disease. Neurobiol Aging. May-Jun. 2000;21(3):383-421.
Al-Muhsen SZ, Shablovsky G, Olivenstein R, Mazer B, Hamid Q. The expression of stem cell factor and c-kit receptor in human asthmatic airways. Clin Exp Allergy. Jun. 2004: 34(6):911-6.
Anastassiadis T, Deacon SW, Devarajan K, Ma H, Peterson JR. Comprehensive assay of kinase catalytic activity reveals features of kinase inhibitor selectivity. Nature Biotechnology. Oct. 30, 2011: 1-7.
Anderson JC, McFarland BC, Gladson CL. New Molecular Targets in the Angiogenic Vessels of Glioblastoma. NIH Public Access Author Manuscript. 2009 Expert Rev Mol Med. ; 10: e23.
Appel H, Maier R, Wu P, Scheer R, Hempting A, Kayser R, Theil A, Radbruch A, Loddenkemper C, Sieper J. Analysis of IL-17+ cells in facet joints of patients with spondyloarthritis suggests that the innate immune pathway might be greater relevance than the TH17-mediated adaptive immune respons. Arthritis Research & Therapy. 2011, 13:R95
Attoub S, Rivat C, Rodrigues S, Van Bocxlaer S, Bedin M, Bruyneel E, Louvet C, Kornprobst M, André T, Mareel M, Mester J, Gespach C. The c-kit tyrosine kinase inhibitor STI571 for colorectal cancer therapy. Cancer Res. Sep. 1, 2002;62(17):4879-83.
Bakharevski O, Ryan PF. Mast cells as a target in the treatment of rheumatoid arthritis. Inflammopharmacology. 1999;7(4):351-62.
Banks ML, Andersen ML, Murnane KS, Meyer RC, Howell LL. Behavioral and neurachemical effects of cocaine and diphenhydramine combinations in rhesus monkeys. Psychopharmacology (Berl.) Aug. 2009; 205(3): 467-474.
Bebo BF Jr, Yong T, Orr EL, Linthicum DS. Hypothesis: a possible role for mast cells and their inflammatory mediators in the pathogenesis of autoimmune encephalomyelitis. J Neurosci Res. 1996; 45:340-348.
Bellone, G., Carbone, A., Sibona, N., Bosco, O., Tibaudi, D., Smirne, C., Martone, T., Gramigni, C., Camandona, M., Emanuelli, G., and Rodeck, U. Aberrant activation of c-kit protects colon carcinoma cells against apoptosis and enhances their invasive potential. Cancer Res., 61: 2200-2206, 2001.
Bellone, G., Silvestri, S., Artusio, E., Tibaudi, D., Turletti, A., Geuna, M., Giachino, C., Valente, G., Emanuelli, G., and Rodeck, U. Growth stimulation of colorectal carcinoma cells via the c-kit receptor is inhibited by TGF. J. Cell. Physiol., 172:1-11, 1997.
Bidri M, Feger F, Varadaradjalou S, Ben Hamouda N, Guillosson JJ, Arock M. Mast cells as a source and target for nitric oxide. Int Immunopharmacol. 2001;1:1543-1558.
Blum-Degen D, Müller T, Kuhn W, Gerlach M, Przuntek H, Riederer P. Interleukin-1 beta and interleukin-6 are elevated in the cerebrospinal fluid of Alzheimer's and de novo Parkinson's disease patients. Neurosci Lett 1995; 202: 17-20.
Blunk JA, Schmelz M, Zeck S, Skov P, Likar R, Koppert W. Opiod-Induced Mast Cell Activation and Vascular Responses in Not Mediated by μ-Opiod Receptors: An In Vivo Mincrodialysis Study in Human Skin. Anesth Analg 2004; 98: 364-70.
Bowman GL, Kaye JA, Moore M, Waichunas D, Carlson NE, Quinn JF. Blood-brain barrier impairment in Alzheimer disease: Stability and functional significance. Neurology. May 22, 2007; 68(21): 1809-1814.
Bradding P, Roberts JA, Britten KM, Montefort S, Djukanovic R, Mueller R, Heusser CH, Howarth PH, Holgate ST. Interleukin-4, -5, and -6 and tumor necrosis factor-alpha in normal and asthmatic airways: evidence for the human mast cell as a source of these cytokines. Am J Respir Cell Mol Biol. May 1994;10(5):471-80.
Brenner T, Soffer D, Shalit M, Levi-Schaffer F. Mast cells in experimental allergic encephalomyelitis: characterization, distribution in the CNS and in vitro activation by myelin basic protein and neuropeptides. J Neurol Sci. 1994;122:210-213.
Brown MA, Tanzola MB, Robbie-Ryan M. Mechanisms underlying mast cell influence on EAE disease course. Mol Immunol. 2002;38(16-18):1373-78.
Cacabelos R, Yamatodani A, Niigawa H, Hariguchi S, Tada K, Nishimura T, Wada H, Brandeis L, Pearson J. Brain histamine in Alzheimer's disease. Methods Find Exp Clin Pharmacol. May 1989;11(5):353-60.
Cadot P, Hensel P, Bensignor E, Hadjaje C, Marignacs G, Beco L, Fontaine J, Jamet JP, Georgescu G, Campbell K, Connon A, Osborn SC, Messinger L, Gogny-Goubert M, Dubreuil P, Moussy A, Hermine O. Masitinib decreases signs of canine atopic dermatitis: a multicentre, randomized, double-blind, placebo-controlled phase 3 trial. Veterinary Dermatology 2011; 1-11.
Cai SW, Yang SZ, Gao J, Pan K, Chen JY, Wang YL, Xin LX, Dong JH. Prognostic significance of mast cell count following curative resection for pancreatic ductal adenocarcinoma. Surgery Apr. 2011: 576-584.
Caroselli C, Perfetti P, Fruno G. High serum tryptase value in massive acute myocardial infarction with ventricular arrhythmia exortion in cocain abuser. Int J Immunopathol Pharmacol. Apr.-Jun. 2009; 22(2): 525-9.

(56) References Cited

OTHER PUBLICATIONS

Ceponis A, Konttinen YT, Takagi M, Xu JW, Sorsa T, Matucci-Cerinic M, Santavirta S, Bankl HC, Valent P. Expression of stem cell factor (SCF) and SCF receptor (c-kit) in synovial membrane in arthritis: correlation with synovial mast cell hyperplasia and inflammation. J Rheumatol. Dec. 1998;25(12):2304-14.

Ch-ng S, Wallis RA, Yuan L, Davis PF, Tan ST. Mast cells and cutaneous malignancies. Modern Pathology 2006, 19; 149-159.

Chang DZ, Ma Y, Ji B, Wang H, Deng D, Liu Y, Abbruzzese JL, Liu YJ, Logsdon CD, Hwu P. Mast Cells in Tumor Microenvironment Promotes the In Vivo Growth of Pancreatic Ductal Adenocarcinoma. Clinical Cancer Research: Nov. 15, 2011; 17(22).

Cho JY. Recent Advances in Mechanisms and Treatments of Airway Remodeling in Asthma: A message from the Bench Side to the Clinic. Korean J Intern Med 2011; 26:367-383.

Christy AL, Brown MA. The Multitasking Mast Cell: Positive and Negative Roles in the Progression of Autoimmunity. J Immunol 2007; 179: 2673-2679.

Cirulli F, et al. Increased number of mast cells in the central nervous system of adult male mice following chronic subordination stress. Brain behav immune 1998; 12: 123-133.

Clifford PM, Zarrabi S, Siu G, Kinsler KJ, Kosciuk MC, Venkataraman V, D'Andrea MR, Dinsmore S, Nagele RG. Aβ peptides can enter the brain through a defective blood-brain barrier and bind selectively to neurons. Brain Research 1142 (2007) 223-236.

Coussens LM, Werb Z. Inflammation and cancer. Nature. Dec. 19-26, 2002;420(6917):860-7.

Crisp AJ, et al. Mast cells in rheumatoid arthritis. J R Soc Med. Jun. 1984; 77(6): 450-451.

Damsgaard TE, Olesen AB, Sørensen FB, Thestrup-Pedersen K, Schiøtz PO. Mast cells and atopic dermatitis. Stereological quantification of mast cells in atopic dermatitis and normal human skin. Arch Dermatol Res. Apr. 1997;289(5):256-60.

Davies H, Bignell GR, Cox C, et al: Mutations of the BRAF gene in human cancer. Nature 417:949-954, 2002.

Davis MI, Hunt JP, Herrgard S, Ciceri P, Wodicka LM, Pallares G, Hocker M, Treiber DK, Zarrinkar PP. Comprehensive analysis of kinase inhibitor selectivity. Nature Biotechnology. Oct. 30, 2011.

Demetri GD. Differential Properties of Current Tyrosine Kinase Inhibitors in Gastrointestinal Stromal Tumors. Seminars in Oncology. Apr. 2011. vol. 38, No. 2, Suppl. 1. pp. S10-S19.

Di Bello MG, Masini E, Ioannides C, Fomusi Ndisang J, Raspanti S, Bani Sacchi T, Mannaioni PF. Histamine release from rat mast cells induced by the metabolic activation of drugs of abuse into free radicals. Inflamm Res. Mar. 1998;47(3):122-130).

Di Chiara G. The role of dopamine in drug abuse viewed from the perspective of its role in motivation. Drug Alcohol Depend. May 1995;38(2):95-137.

DiPaola RS, Kuczynski WI, Onodera K, Ratajczak MZ, Hijiya N, Moore J, Gewirtz AM. Evidence for a functional kit receptor in melanoma, breast, and lung carcinoma cells. Cancer Gene Ther. May-Jun. 1997;4(3):176-82.

Dobbs RJ, Charlett A, Purkiss AG, Dobbs SM, Weller C, Peterson DW. Association of circulating TNF-alpha and IL-6 with ageing and parkinsonism. Acta Neurol Scand 1999; 100: 34-41.

Dubreuil P, Letard S, Ciufolini M, Gros L, Humbert M, Casteran N, Borge L, Hajem B, Lermet A, Sippl W, Voisset E, Arock M, Auclair C, Leventhal PS, Mansfield CD, Alain M, Hermine O. Masitinib (AB1010), a Potent and Selective Tyrosine Kinase Inhibitor Targeting KIT. PLos ONE Sep. 2009, vol. 4, Issue 9, e7258.

Dvorak AM, Monahan RA, Osage JE, Dickersin GR. Crohn's disease: transmission electron microscopic studies. II. Immunologic inflammatory response. Alterations of mast cells, basophils, eosinophils, and the microvasculature. Hum Pathol 1980; 11: 606-619.

Edston E, van Hage-Hamsten M. Anaphylactoid shock—a common cause of death in heroin addicts? Allergy. Sep. 1997;52(9):950-4.

Esposito P, Gheorghe D, Kandere K, Pang X, Connolly R, Jacobson S, Theoharides TC. Acute stress increases permeability of the blood-brain-barrier through activation of brain mast cells. Brain Res. Jan. 5, 2001;888(1):117-127.

Esposito P, Chandler N, Kandere K, Basu S, Jacobson S, Connolly R, Tutor D, Theoharides TC. Corticotropin-releasing hormone and brain mast cells regulate blood-brain-barrier penmeability induced by acute stress. J Pharmacol Exp Ther. 2002;303:1061-1066.

Farooq RK, Isingrini E, Tanti A, Le Guisquest AM, Arlicot N, Minier F, Leman S, Chalon S, Belzung C, Camus V. Is unpredictable chronic mild stress (UCMS) a reliable model to study despression-induced neuroinflammation? Behavioral Brain Research 231 (2012) 130-137.

Freemont AJ, Denton J. Disease distribution of synovial fluid mast cells and cytophagocytic mononuclear cells in inflammatory arthritis. Ann Rheum Dis. May 1985;44(5):312-5.

Frischer JM, Bramow S, Dal-Bianco A, Lucchinetti CF, Rauschka H, Schmidbauer M, Laursen H, Sorensen PS, Lassmann H.). The relation between inflammation and neurodegeneration in multiple sclerosis brains. Brain. May 2009;132(Pt 5):1175-89.

Garbuzova-Davis S, Saporta S, Haller E, Kolomey I, Bennett SP, Potter H, Sanberg PR. Evidence of Compromised Blood-Spinal Cord Barrier in Early and Late Symptomatic SOD1 Mice Modeling ALS. PloS ONE Nov. 2007, Issue 11, e1205.

Gaspar RC, Willarreal SA, Bowles N, Hepler RW, Joyce JG, Shughrue PJ. Oligomers of beta-amyloid are sequestered into and seed new plaques in the brains of an AD mouse model. Exp Neurol, Jun. 2010; 223(2): 394-400.

Geissler EN, Melanie AR, Housman DE. The Dominant-White Spotting (W) Locus of the Mouse Encodes the c-kit Proto-Oncogene. Cell, vol. 55, 185-192, Oct. 7, 1988.

Gelbmann CM, Mestermann S, Gross V, Kollinger M, Scholmerich J, Falk W. Strictures in Crohn's disease are characterised by an accumulation of mast cells colocalised with laminin but not with fibronectin or vitronectin. Gut 1999; 45: 210-217.

Getting SJ, Flower RJ, Parente L, de Medicis R, Lussier A, Woliztky BA, Martins MA, Perretti M. Molecular determinants of monosodium urate crystal-induced murine peritonitis: a role for endogenous mast cells and a distinct requirement for endothelial-derived selectins. J Pharmacol Exp Ther. Oct. 1997;283(1):123-30.

Gilbert RE, Rumble JR, Cao Z, Cox AJ, van Eeden P, Allen TJ, Kelly DJ, Cooper ME. Endothelin receptor antagonism ameliorates mast cell infiltration, vascular hypertrophy, and epidermal growth factor expression in experimental diabetes. Circ Res. Feb. 4, 2000;86(2):158-65.

Gilfillan AM, Tkaczyk C. Integrated signaling pathways for mast-cell activation. Nature Mar. 2006, vol. 6. 218-230.

Gilfillan AM, Rivera J. The tyrosine kinase network regulating mast cell activation. Immunol Rev. Mar. 2009; 228(1): 149-169.

Gounaris E, Erdman SE, Restaino C, Gurish MF, Friend DS, Gounari F, Lee DM, Zhang G, Glickman JN, Shin K, Rao VP, Poutahidis T, Weissleder R, McNagny KM, Khazaie K. Mast cells are an essential hematopoietic component. PNAS Dec. 11, 2007, vol. 104, No. 50. 19977-19982.

Graves MC, Fiala M, Dinglasan LA, Liu NQ, Sayre J, Chiappelli F, Van Kooten C, Vinters HV. Inflammation in amyotrophic lateral sclerosis spinal cord and brain is mediated by activated macrophages, mast cells and T cells. Amyotroph Lateral Scler Other Motor Nueron Disord. Dec. 2004; 5(4): 213-9.

Grzanna R, Shultz LD (1982) The contribution of mast cells to the histamine content of the central nervous system: A regional analysis. Life Sci 30:1959-1964.

Harvima IT, Naukkarinen A, Harvina RJ, Horsmanheimo M. Enzyme- and immunohistochemical localization of mast cell tryptase in psoriatic skin. Arch Dermatol Res (1989) 281: 387-391.

Harvima IT, Nilsson G, Suttle MM, Naukkarinen A. Is there a role for mast cells in psoriasis? Arch Dermatol Res Jun. 2008.

Hassan S, Kinoshita Y, Kawanami C, Kishi K, Matsushima Y, Ohashi A, Funasaka Y, Okada A, Maekawa T, He-Yao W, Chiba T. Expression of protooncogene c-kit and its ligand stem cell factor (SCF) in gastric carcinoma cell lines. Dig Dis Sci. Jan. 1998;43(1):8-14.

He Shao-Heng. Key role of mast cells and their major secretory products in inflammatory bowel disease. World J Gastroenterol. Feb. 1, 2004;10(3):309-18. Review.

(56) References Cited

OTHER PUBLICATIONS

Heinrich MC, Rubin BP, Longley BJ, Fletcher JA. Biology and genetic aspects of gastrointestinal stromal tumors: KIT activation and cytogenetic alterations. Hum Pathol. May 2002; 33(5):484-95.

Heleniak E, O'Desky I. Histamine and prostaglandins in schizophrenia: revisited. Med Hypotheses. Jan. 1999;52(1):37-42.

Hermine O, Lortholary O, Leventhal PS, Catteau A, Soppelsa F, Baude C, Cohen-Akenine A, Palmerini F, Hanssens K, Yang Y, Sobol H, Fraytag S, Ghez D, Saurez F, Barete S, Casassus P, Sans B, Arock M, Kinet JP, Dubreuil P, Moussy A. Case-Control Cohort Study of Patients' Perceptions of Disability in Mastocytosis. PLoS ONE May 2008; vol. 3, Issue 5.

Hill PB, Olivry T. The ACVD task force on canine atopic dermatitis (V): biology and role of inflammatory cells in cutaneous allergic reactions. Vet Immunol Immunopathol. Sep. 20, 2001;81(3-4):187-98.

Hirota S, Isozaki K, Moriyama Y, Hashimoto K, Nishida T, Ishiguro S, Kawano K, Hanada M, Kurata A, Takeda M, Muhammad Tunio G, Matsuzawa Y, Kanakura Y, Shinomura Y, Kitamura Y. Gain-of-function mutations of c-kit in human gastrointestinal stromal tumors. Science. Jan. 23, 1998;279(5350):577-80.

Hirota S, Nishida T, Isozaki K, Taniguchi M, Nakamura J, Okazaki T, Kitamura Y: Gain-of-function mutation at the extracellular domain of KIT in gastrointestinal stromal tumours. J Pathol 2001, 193(4):505-510.

Hirsh EC, Hunot S. Neuroinflammation in Parkinson's disease: a target for neuroprotection? Lancet Neurol 2009; 8: 382-97.

Hohlfeld R, Kappos L. Progress in understanding inflammatory and autoimmune diseases of the central nervous system. Semin immunopathol (2009) 31:437-438.

Hou C, Jia F, Liu Y, Li L. CSF serotonin, 5-hydroxyindolacetic acid and neuropeptide Y levels in severe major depressive disorder. Brain Research 1095 (2006) 154-158.

Huang E, Nocka K, Beier DR, Chu TY, Buck J, Lahm HW, Weliner D, Leder P, Besmer P. The Hematopoietic Growth Factor KL Is Encoded by the Sl Locus and Is the Ligand of the c-kit Refeptor, the Gene Product of the W Locus. Cell, vol. 63, 225-233, Oct. 5, 1990.

Humbert M, Blay F, Garcia G, Prud'homme A, Leroyer C, Magnan A, Tunon-de-Lara JM, Pison C, Aubier M, Charpin D, Vachier I, Purohit A, Gineste P, Bade T, Moussy A, Hermine O, Chanez P. Masitinib, a c-kit/PDGF receptor tyrosine kinase inhibitor, improves disease control in severe corticosteroid-dependent asthmatics. Allergy 2009: 64: 1194-1201.

Hunot S, Boissiere F, Faucheux B, Brugg B, Mouatt-Prigent A, Agid Y, Hirsch EC, Nitric oxide synthase and neuronal vulnerability in Parkinson's disease, Neuroscience. May 1996;72(2):355-63.

Iadecola C, Alexander M. Cerebral ischemia and inflammation. Curr Opin Neurol. Feb. 2001;14(1):89-94.

Kalaria RN, Golde TE, Cohen ML, Younkin SG. Serum amyloid P in Alzheimer's disease. Implications for dysfunction of the blood-brain barrier. Ann N Y Acad Sci. 1991;640:145-8.

Kanbe T, Soma Y, Kawa Y, Kashima M, Mizoguchi M. Serum levels of soluble stem cell factor and soluble KIT are elevated in patients with atopic dermatitis and correlate with the disease severity. Br J Dermatol. Jun. 2001;144(6):1148-53.

Kavya R, Dikshit M. Role of Nitric Oxide/Nitric Oxide Synthase in Parkinsons's Disease. Annals of Neurosciences, Apr. 2005, vol. 12, Issue 2.

Kelley JL, Chi DS, Abou-Auda W, Smith JK, Krishnaswamy G. The molecular role of mast cells in atherosclerotic cardiovascular disease. Mol Med Today. Aug. 2000;6(8):304-8.

Kiener HP, Hofbauer R, Tohidast-Akrad M, Walchshofer S, Redlich K, Bitzan P, Kapiotis S, Steiner G, Smolen JS, Valent P. Tumor necrosis factor alpha promotes the expression of stem cell factor in synovial fibroblasts and their capacity to induce mast cell chemotaxis. Arthritis Rheum. Jan. 2000;43(1):164-174.

Kim YS, Ko HM, Kang NI, Song CH, Zhang X, Chung WC, Kim JH, Choi IH, Park YM, Kim GY, Im SY, Lee HK. Mast cells play a key role in the development of late airway hyperresponsiveness through TNF-α in a murine model of asthma. Eur. J. Immunol. 2007. 37: 1107-1115.

Kinet JP. The essential role of mast cells in orchestrating inflammation. Immunological Reviews 2007, vol. 217: 5-7.

Kitamura Y, Go S. Decreased production of mast cells in Sl/Sld anemic mice. Blood 1979 53: 492-497.

Kneilling M, Rocken M. Mast cells: novel clinical perspectives from recent insights. Experimental Dermatology 2009, 18, 488-496.

Kobayashi T, Miura T, Haba T, Sato M, Serizawa I, Nagai H, Ishizaka K. An essential role of mast cells in the development of airway hyperresponsiveness in a murine asthma model. J Immunol. Apr. 1, 2000;164(7):3855-61.

Kortekaas R, Leenders KL, van Oostrom JCH, Vaalburg W, Bart J, Willemsen ATM, Hendrikse NH. Blood-Brain Barrier Dysfunction in Parkinsonian Midbrain In Vivo. Ann Neurol 2005;57:176-179.

Lachter J, Stein M, Lichtig C, Eidelman S, Munichor M. Mast cells in colorectal neoplasias and premalignant disorders. Dis Colon Rectum. Mar. 1995;38(3):290-3.

Lasota J, Jasinski M, Sarlomo-Rikala M, Miettinen M. Mutations in exon 11 of c-Kit occur preferentially in malignant versus benign gastrointestinal stromal tumors and do not occur in leiomyomas or leiomyosarcomas. Am J Pathol. Jan. 1999;154(1):53-60.

Cesne AL, Blay JY, Bui BN, Bouche O, Adenis A, Domont J, Cioffi A, Ray-Coquard I, Lassau N, Bonvalot S, Moussy A, Kinet JP, Hermine O. Phase II study of oral masitinib mesilate in imatinib-naïve patients with locally advanced or metastatic gastro-intestinal stromal tumour (GIST). European Journal of Cancer 2010.

Lee DM, Friend DS, Gurish MF, Benoist C, Matins D, Brenner MB. Mast cells: a cellular link between autoantibodies and inflammatory arthritis. Science. Sep. 6, 2002;297(5587):1689-92.

Lee-Fowler TM, Guntur V, Dodam J, Cohn LA, DeClue AE, Reinero CR. The Tyrosine Kinase Inhibitor masitinib Blunts Airway Inflammation and Improves Associated Lung Mechanics in a Geline Model of Chronic Allergic Asthma. Int Arch Allergy Immunol 2012; 158:369-3744.

Leonardi A, Abbruzzese G, Arata L, Cocito L, Vische M. Cerebrospinal fluid (CSF) findings in amyotrophic lateral sclerosis. J Neurol. 1984;231(2):75-8.

Leza, I. Lizasoain, O. Martin-Clark and P. Lorenzo. Role of sodium cromoglycate on analgesia, locomotor activity and opiate withdrawal in mice. Psychopharmacology. 1992; 107(4) : 595-600.

Libby P, Ridker PM, Maseri A. Inflammation and Atherosclerosis Circulation. 2002;105:1135-1143.

Lilja I, Gustafson-Svard C, Franzen L, Sjodahl R. Tumor necrosis factor-alpha in ileal mast cells in patients with Crohn's disease. Digestion 2000; 61: 68-76.

Lindsberg PJ, Strbian D, Karjalainen-Lindsberg ML. Mast cells as early responders in the regulation of acute blood-brain barrier changes after cerebral ischemia and hemorrhage. Journal of Cerebral Blood Flow & Metabolism (2010) 30, 689-702.

Longley BJ, Reguera MJ, Ma Y. Classes of c-KIT activating mutations: proposed mechanisms of action and implications for disease classification and therapy. Leuk Res. Jul. 2001;25(7):571-6.

Maes M. Editorial board. Psychological stress and the inflammatory response system. Clin Sci (Lond), 2001; 101: 193-194.

Makowska JS, Cieslak M, Kowalski ML. Stem cell factor and its soluble receptor (c-kit) in serum of asthmatic patients—correlation with disease severity. BMC Pulmonary Medicine 2009, 9:27.

Marone, C. Stellato, P. Mastronardi and B. Mazzarella. Mechanism of activation of human mast cells and basophils by general anesthetic drugs. Ann Fr Anesth Ream. 1993; 12(2) : 116-125.

McGeer PL, Itagaki S, Boyes BE, McGeer EG. Reactive microglia are positive for HLA-DR in the substantia nigra of Parkinson's and Alzheimer's disease brains. Neurology 1988; 38: 1285-91.

Miettinen M, Lasota J. Gastrointestinal stromal tumors—definition, clinical, histological, immunohistochemical, and molecular genetic features and differential diagnosis. Virchows Arch (2001) 438:1-12.

Miettinen M, Lasota J. Gastrointestinal stromal tumors (GISTs): Definition, Occurrence, Pathology, Differential Diagnosis and Molecular Genetics. Pol J Pathol 2003, 54, 1, 3-24.

(56) References Cited

OTHER PUBLICATIONS

Mogi M, Harada M, Riederer P, Narabayashi H, Fujita K, Nagatsu T. Tumor necrosis factor-alpha (TNF-alpha) increases both in the brain and in the cerebrospinal fluid from parkinsonian patients. Neurosci Lett 1994; 165: 208-210.
Moor ACE, de Vries HE, de Boer AG, and Breimer DD (1994) The blood-brain barrier and multiple sclerosis. Biochem Pharmacol 47:1717-1724.
Müller T, Blum-Degen D, Przuntek H, Kuhn W. Interleukin-6 levels in cerebrospinal fluid inversely correlate to severity of Parkinson's disease. Acta Neurol Scand 1998; 98: 142-44.
Murphy GF, Sueki H, Teuscher C, Whitaker D, Korngold R. Role of mast cells in early epithelial target cell injury in experimental acute graft-versus-host disease. J Invest Deimatol. Apr. 1994;102(4):451-61.
Nabors LB, Suswam E, Huang Y, et al. Tumor Necrosis Factor α Induces Angiogenic Factor Up-Regulation in Malignant Glioma Cells: A Role for RNA Stabilization and HuR. Cancer Res Jul. 2003; 63: 4187.
Naslund J, Haroutunian V, Mohs R, Davis KL, Davies P, Greengard P, Buxbaum JD. Correlation Between Elevated Levels of Amyloid β-Peptide in the Brain and Cognitive Decline. JAMA Mar. 22-29, 2000—vol. 283, No. 12, 1571-1577.
Nautiyal KM, Ribeiro AC, Pfaff DM, Silver R. Brain mast cells link the immune system to anxiety-like behavior. PNAS, Nov. 188, 2008, vol. 105, No. 46, 18053-18057.
Nelson RB, Siman R, Iqbal MA, Potter H. Identification of a chymotrypsin-like mast cell protease in rat brain capable of generating the N-terminus of the Alzheimer amyloid beta-protein. J Neurochem. Aug. 1993;61(2):567-77.
Niederhorrer N, Levy R, Sick E, Andre P, Coupin G, Lombard Y, Gies JP. Amyloid beta peptides trigger CD47-dependent mast cell secretory and phagocytic responses. Int. J. Immunopathol Pharmacol. Apr.-Jun. 2009;22(2):473-83.
Nishizawa S, Benkelfat C, Young SN, Leyton M, Mzengeza S, de Montigny C, Blier P, Dikic. Differences between males and females in rates of serotonin synthesis in human Brain. Proc Natl Acad Sci USA. May 13, 1997; 94(10):5308-13.
Okayama Y, Ra C, Saito H. Role of mast cells in airway remodeling. Current Opinion in Immunology 2007, 19:687-693.
Owens MJ, Nemeroff CB. Role of serotonin in the pathophysiology of depression: focus on the serotonin transporter. 1994; Clin Chem. Feb. 1994;40 (2):288-95.
Ozdamar SO, Seckin D, Kandemir B, Turanli AY. Mast Cells in Psoriasis. Dermatology 1996; 192:190.
Paul C, Bolton C. Modulation of blood-brain barrier dysfunction and neurological deficits during acute experimental allergic encephalomyelitis by the N-methyl-D-aspartate receptor antagonist memantine. J Pharmacol Exp Ther. Jul. 2002:302(1):50-7.
Paul C, Sans B, Suarez F, Casassus P, Barete S, Lanternier F, Grandpeix-Guyodo C, Bubreuil P, Palmerini F, Mansfield CD, Bineste P, Moussy A, Hermine O, Lortholary O. Masitinib for the treatment of systemic and cutanesou mastocytosis with handicap: A phase 2a study. American Journal of Hematology. 85:921-925, 2010.
Peeker R, Enerbäck L, Fall M, Aldenborg F. Recruitment, distribution and phenotypes of mast cells in interstitial cystitis. J Urol. Mar. 2000;163(3):1009-15.
Pidhorecky I, Cheney RT, Kraybill WG, Gibbs JF. Gastrointestinal stromal tumors: current diagnosis, biologic behavior, and management. Ann Surg Oncol. Oct. 2000;7(9):705-12.
Pietsch T, Nicotra MR, Fraioli R, Wolf HK, Mottolese M, Natali PG. Expression of the c-Kit receptor and its ligand SCF in non-small-cell lung carcinomas. Int J Cancer. Jan. 19, 1998;75(2):171-5.
Piette F, Belmin J, Vincent H, Schmidt N, Panel S, Verny M, Marquis C, Mely J, Hugonot-Diener L, Kinet JP, Dubreuil P, Moussy A, Hermine O. Masitinib as an adjunct therapy for mild-to-moderate Alzheimer's disease: a randomized placebo-controlled phase 2 trial Alzheimer's Research & Terapy 2011, 3:16.

Polajeva J, Sjosten AM, Lager N, et al. Mast Cell Accumulation in Glioblastoma with a Potential Role for Stem Cell Factor and Chemokine CXCL12. PLoS ONE, Sep. 2011, vol. 6, Issue 9.
Raoul C, Estévez AG, Nishimune H, Cleveland DW, deLapeyrière O, Henderson CE, Haase G, Pettmann B. Motoneuron death triggered by a specific pathway downstream of Fas. potentiation by ALS-linked SOD1 mutations. Neuron. Sep. 12, 2002;35(6):1067-83.
Rascher G, Fischmann A, Kröger S, Duffner F, Grote EH, Wolburg H. Extracellular matrix and the blood-brain barrier in glioblastoma multiforme: spatial segregation of tenascin and agrin. Acta Neuropathol. Jul. 2002;104(1):85-91. Epub Mar. 28, 2002.
Reber L, Da Silva CA, Frossard N. Stem cell factor and its receptor c-Kit as targets for inflammatory diseases. Eur J Pharmacol. Mar. 8, 2006;533(1-3):327-40. Epub Feb. 17, 2006.
Reed JA, McNutt NS, Bogdany JK, Albino AP. Expression of the mast cell growth factor interleukin-3 in melanocytic lesions correlates with an increased number of mast cells in the perilesional stroma: implications for melanoma progression. J Cutan Pathol. Dec. 1996;23(6):495-505.
Ribatti D, Guidolin D, Marzullo A, et al. Mast cells and angiogenesis in gastric carcinoma. Int. J. Exp. Path. 2010, 91, 350-356.
Ronnberg E, Calounova G, Pejler G. Mast cells express tyrosine hydroxylase and store dopamine in serglycin-dependent manner. Bio Chem., vol. 393, pp. 107-112, Jan.-Feb. 2012.
Rüger BM, Hasan Q, Greenhill NS, Davis PF, Dunbar PR, Neale TJ. Mast cells and type VIII collagen in human diabetic nephropathy. Diabetologia. Oct. 1996;39(10):1215-22.
Sant GR, Theoharides TC. The role of the mast cell in interstitial cystitis. Urol Clin North Am. Feb. 1994;21(1):41-53.
Sant GR, Kempuraj D, Marchand JE, Theoharides TC. The Mast Cell in Interstitial Cystitis: Role in Pathophysiology and pathogenesis. Urology. Apr. 2007; 69(4suppl):34-40.
Sasaki Y, Tanaka M, Kudo H. Differentiation between ulcerative colitis and Crohn's disease by a quantitative immunohistochemical evaluation of T lymphocytes, neutrophils, histiocytes and mast cells. Pathol Int 2002; 52: 277-285.
Sayed BA, Christy AL, Walker ME, Brown MA. Meningeal Mast Cells Affect Early T Cell Central Nervous System infiltration and Blood-Brian Barrier Integrity through TNF: A Role for Neutrophil Recruitment? J Immuno 2010; 184:6891-6900.
Schiltz C, Lioté F, Prudhommeaux F, Meunier A, Champy R, Callebert J, Bardin T. Monosodium urate monohydrate crystal-induced inflammation in vivo: quantitative histomorphometric analysis of cellular events. Arthritis Rheum. Jun. 2002;46(6):1643-50.
Schneider SW, Ludwig T, Tatenhorst L, Braune S, Oberleithner H, Serener V, Paulus W. Glioblastoma cells release factors that disrupt blood-brain barrier features. Acta Neuropathol (2004) 107: 272-276.
Schubert C, Christophers E. Mast Cells and Macrophages in Early Relapsing Psoriasis. Arch Dermatol Res (1985) 277:352-358.
Secor VH, Secor WE, Gutekunst CA, Brown MA. Mast cells are essential for early onset and severe disease in a murine model of multiple sclerosis. J Exp Med. Mar. 6, 2000;191(5):813-22.
Shao Z, Zhang H, Chen G, Wang L, Li K, Zhang Y, Li L, Sun J. Expression and function of c-kit receptor in bone marrow mononuclear cells of patients with myelodysplastic syndromes. Chin Med J (Engl). May 2001;114(5):481-5.
Shimizu, M., Minakuchi, K., Tsuda, A., Hiroi, T., Tanaka, N., Koga, J., and Kiyono, H. Role of stem cell factor and c-kit signaling in regulation of fetal intestinal epithelial cell adhesion to fibronectin. Exp. Cell Res., 266: 311-322, 2001.
Siitonen T, Savolainen ER, Koistinen P. Expression of the c-Kit proto-oncogene in myeloproliferative disorders and myelodysplastic syndromes. Leukemia. Apr. 1994;8(4):631-7.
Silverman AJ, Sutherland AK, Wilhelm M, Silver R: Mast cells migrate from blood to brain. J Neurosci 2000, 20:401-408.
Skaper SD, Facci L, Romanello S, Leon A. Mast cell activation causes delayed neurodegeneration in mixed hippocampal cultures via the nitric oxide pathway. J Neurochem. 1996;66:1157-1166.
Soter NA, Mihm MC Jr, Dvorak HF, Austen KF. Cutaneous necrotizing venulitis: a sequential analysis of the morphological alterations occurring after mast cell degranulation in a patient with a unique syndrome. Clin Exp Immunol Apr. 1978;32(1):46-58.

(56) References Cited

OTHER PUBLICATIONS

Sperr WR, Stehberger B, Wimazal F, Baghestanian M, Schwartz LB, Kundi M, Semper H, Jordan JH, Chott A, Drach J, Jäger U, Geissler K, Greschniok A, Horny HP, Lechner K, Valent P. Serum tryptase measurements in patients with myelodysplastic syndromes. Leuk Lymphoma. May 2002;43(5):1097-105.

Stassen M, Hültner L, Müller C, Schmitt E. Mast cells and inflammation. Arch Immunol Ther Exp (Warsz). 2002;50(3):179-85.

Steptoe, A., Willemsen, G., Owen, N., Flower, L., Mohamed-Ali, V. Acute mental stress elicits delayed increases in circulating inflammatory cytokine levels. Clin. Sci. (2001) 101, 185-192.

Strbian D, Karjalainen-Lindsberg ML, Tatlisumak T, Lindsberg PJ. Cerebral mast cells regulate early ischemic brain swelling and neutrophil accumulation. Journal of Cerebral Blood Flow & Metabolism (2006) 26,605-612.

Strbian D, Karjalainen-Lindsberg ML, Kovanen PT, Tatlisumak T, Lindsberg PJ. Mast Cell Stabilization Reduces Hemorrhage Formation and Mortality After Administration of Thrombolytics in Experimental Ischemic Stroke. Circulation. 2007; 116:411-418.

Strbian D. The Role of Mast Cells in Ischemic and Hemorrhagic Brain Injury. Helsinki University Biomedical Dissertations No. 106. Helsinki, 2008.

Strbian D, Kovanen PT, Katjalainen-Lindsberg ML, Tatlisumak T, Lindsberg PJ. An emerging role of mast cells in cerebral ischemia and hemorrhage. Annals of Medicine. 2009; 41: 438-450.

Strouch MJ, Cheon EC, Salabat MR, et al. Crosstalk between mast cells and pancreatic cancer cells contributes to pancreatic tumor progression. Clin Cancer Res. Apr. 15, 2010; 16(8): 2257-2265.

Stypula G, Kunert-Radek J, Stepień H, Zylińska K, Pawlikowski M. Evaluation of interleukins, ACTH, cortisol and prolactin concentrations in the blood of patients with Parkinson's disease. Neuroimmunomodulation 1996; 3: 131-34.

Subramanian N, Theodore D, Abraham J. Experimental cerebral infarction in primates: regional changes in brain histamine content. J Neural Transm. 1981;50(2-4):225-32.

Taiwo OB, Kovacs KJ, Sperry LC, Larson AA. Naloxone-induced morphine withdrawal increases the number and degranulation of mast cells in the thalamus of the mouse. Neuropharmacology 46 (2004) 824-835.

Tazawa K, Tsukada K, Makuuchi H, Tsutsumi Y. An immunohistochemical and clinicopathological study of gastrointestinal stromal tumors. Pathol Int. Sep. 1999;49(9):786-8.

Tebib J, Mariette X, Bourgeois P, Flipo RM, et al. Masitinib in the treatment of active rheumatoid arthritis: results of a multicentre, open-label, dose-ranging, phase 2a study.Arthritis Research & Therapy 2009, 11:R95.

Theoharides TC, Sieghart W, Greengard P, Douglas WW (1980) Antiallergic drug cromolyn may inhibit histamine secretion by regulating phosphorylation of a mast cell protein. Science 207:80-82.

Theoharides TC, Kempuraj D, Sant GR. Mast cell involvement in interstitial cystitis: a review of human and experimental evidence. Urology. Jun. 2001;57(6 Suppl 1):47-55.

Theoharides TC. Mast cells and stress—a psychoneuroimmunological perspective. J Clin Psychopharmacol. Apr. 2002;22(2):103-8.

Theoharides TC, Donelan J, Kandere-Grzybowska K, Konstantinidou A. The role of mast cells in migraine pathophysiology. Brain Res Brain Res Rev. Jul. 2005;49(1):65-76.

Tomita M, Matsuzaki Y, Onitsuka T. Effect of mast cells on tumor angiogenesis in lung cancer. Ann Thorac Surg. Jun. 2000;69(6):1686-90.

Toruniowa B., Jablonska S. Mast cells in the initial stages of psoriasis. Arch Dermaatol Res (1988) 280: 189-193.

Tóth-Jakatics R, Jimi S, Takebayashi S, Kawamoto N. Cutaneous malignant melanoma: correlation between neovascularization and peritumor accumulation of mast cells overexpressing vascular endothelial growth factor. Hum Pathol. Aug. 2000;31(8):955-960.

Toyry S, Fraki J, Tammi R. Mast cell density in psoriatic skin. The effect of PUVA and corticosteriod therapy. Arch Dermatol Res (1988) 280: 282-285.

Tsujimura T, Furitsu T, Morimoto M, Isozaki K, Nomura S, Matsuzawa Y, Kitamura Y, Kanakura Y. Ligand-independent activation of c-kit receptor tyrosine kinase in a murine mastocytoma cell line P-815 generated by a point mutation. Blood. May 1, 1994;83(9):2619-26.

Van Meir E, Ceska M, Effenberger F, Walz A, Grouzmann E, Desbaillets I, et al. Interleukin-8 is produced in neoplastic and infectious diseases of the human central nervous system. Cancer Res 1992;52(16):4297-4305.

Vermersch P, Benrabah R, Schmidt N, Zephir H, et al. Masitinib treatment in patients with progressive multiple sclerosis: a randomized pilot study. BMC Neurology 2012, 12:36.

Volkow ND, Wang GJ, Fischman MW, Foltin RW, Fowler JS, Abumrad NN, Vitkun S, Logan J, Gatley SJ, Pappas N, Hitzemann R, Shea CE. Relationship between subjective effects of cocaine and dopamine transporter occupancy. Nature. Apr. 24, 1997;386(6627):827-30.

Weydt P, Weiss MD, Möller T, Carter GT.Neuro-inflammation as a therapeutic target in amyotrophic lateral sclerosis. Curr Opin Investig Drugs. Dec. 2002;3(12):1720-24.

Wimazal F, Sperr WR, Horny HP, Carroll V, Binder BR, Fonatsch C, Walchshofer S, Födinger M, Schwarzinger I, Samorapoompichit P, Chott A, Dvorak AM, Lechner K, Valent P. Hyperfibrinolysis in a case of myelodysplastic syndrome with leukemic spread of mast cells. Am J Hematol. May 1999;61(1):66-77.

Yamamoto T, Katayama I, Nishioka K. Possible contribution of stem cell factor in psoriasis vulgaris. Journal of Dermatological Science 24 (2000) 171-176.

Yano H, Kinuta M, Tateishi H, Nakano Y, Matsui S, Monden T, Okamura J, Sakai M, Okamoto S. Mast cell infiltration around gastric cancer cells correlates with tumor angiogenesis and metastasis. Gastric Cancer. May 1999;2(1):26-32.

Yasuda A, Sawai H, Takahashi H, Ochi N, et al. The stem cell factor/c-kit receptor pathway enhances proliferation and invasion of pancreatic cancer cells. Molecular Cancer 2006, 5:46.

Yousem SA. The potential role of mast cells in lung allograft rejection. Hum Pathol. Feb. 1997;28(2):179-182.

Yuzurihara M, Ikarashi Y, Ishige A, Sasaki H, Kuribara H, Maruyama Y. Effects of drugs acting as histamine releasers or histamine receptor blockers on an experimental anxiety model in mice. Pharmacol Biochem Behav. Sep. 2000; 67(1):145-50.

Zhang W, Stanimirovic D. Current and future therapeutic strategies to target inflammation in stroke. Curr Drug Targets Inflamm Allergy. Jun. 2002;1(2):151-66.

Zhuang X, Silverman AJ, Silver R. Brain mast cell degranulation regulates blood-brain barrier. J Neurobiol. Dec. 1996;31(4):393-403.

Zotova E, Nicoll J AR, Kalaria R, Holmes C, Boche D. Inflammation in Alzheimer's disease: relevance to pathogenesis and therapy. Alzheimer's Research & Therapy 2010, 2:1.

Lowenberg et al., Acute Myeloid Leukemia. N. Eng. J. Med. 1999; 341: 1051-1062.

* cited by examiner

US 8,993,573 B2

2-(3-AMINOARYL) AMINO-4-ARYL-THIAZOLES AND THEIR USE AS C-KIT INHIBITORS

CROSS-REFERENCE TO RELATED APPLICATIONS

This application is a continuation of U.S. patent application Ser. No. 13/015,664 filed on Jan. 28, 2011, which is a continuation of U.S. patent application Ser. No. 11/779,633 filed on Jul. 18, 2007, which is a continuation of U.S. patent application Ser. No. 10/523,018 filed on Feb. 2, 2005, which is a national stage of PCT/IB03/03685 filed under 35 U.S.C. §371 on Jul. 31, 2003, which claims the benefit of U.S. Provisional Application No. 60/400,064 filed on Aug. 2, 2002, the complete disclosures of which are incorporated into this application by reference. This application also claims the benefit of U.S. patent application Ser. No. 10/632,101 filed Aug. 1, 2003, which claims the benefit of U.S. Provisional Application No. 60/400,064 filed on Aug. 2, 2002.

DESCRIPTION OF THE INVENTION

The present invention relates to novel compounds selected from 2-(3-aminoaryl)amino-4-aryl-thiazoles that selectively modulate, regulate, and/or inhibit signal transduction mediated by certain native and/or mutant tyrosine kinases implicated in a variety of human and animal diseases such as cell proliferative, metabolic, allergic, and degenerative disorders. More particularly, these compounds are potent and selective c-kit inhibitors.

Tyrosine kinases are receptor type or non-receptor type proteins, which transfer the terminal phosphate of ATP to tyrosine residues of proteins thereby activating or inactivating signal transduction pathways. These proteins are known to be involved in many cellular mechanisms, which in case of disruption, lead to disorders such as abnormal cell proliferation and migration as well as inflammation.

As of today, there are about 58 known receptor tyrosine kinases. Other tyrosine kinases are the well-known VEGF receptors (Kim et al., Nature 362, pp. 841-844, 1993), PDGF receptors, c-kit and the FLK family. These receptors can transmit signals to other tyrosine kinases including Src, Raf, Frk, Btk, Csk, Abl, Fes/Fps, Fak, Jak, Ack. etc.

Among tyrosine kinase receptors, c-kit is of special interest. Indeed, c-kit is a key receptor activating mast cells, which have proved to be directly or indirectly implicated in numerous pathologies for which the Applicant filed WO 03/004007, WO 03/004006, WO 03/003006, WO 03/003004, WO 03/002114, WO 03/002109, WO 03/002108, WO 03/002107, WO 03/002106, WO 03/002105, WO 03/039550, WO 03/035050, WO 03/035049, U.S. 60/359,652 and U.S. 60/359,651.

It was found that mast cells present in tissues of patients are implicated in or contribute to the genesis of diseases such as autoimmune diseases (rheumatoid arthritis, inflammatory bowel diseases (IBD)) allergic diseases, tumor angiogenesis, inflammatory diseases, and interstitial cystitis. In these diseases, it has been shown that mast cells participate in the destruction of tissues by releasing a cocktail of different proteases and mediators such as histamine, neutral proteases, lipid-derived mediators (prostaglandins, thromboxanes and leucotrienes), and various cytokines (IL-1, IL-2, IL-3, IL-4, IL-5, IL-6, IL-8, TNF-α, GM-CSF, MIP-1a, MIP-1b, MIP-2 and IFN-γ).

The c-kit receptor also can be constitutively activated by mutations leading to abnormal cell proliferation and development of diseases such as mastocytosis and various cancers.

For this reason, it has been proposed to target c-kit to deplete the mast cells responsible for these disorders.

The main objective underlying the present invention is therefore to find potent and selective compounds capable of inhibiting wild type and/or mutated c-kit.

Many different compounds have been described as tyrosine kinase inhibitors, for example, bis monocyclic, bicyclic or heterocyclic aryl compounds (WO 92/20642), vinylene-azaindole derivatives (WO 94/14808) and 1-cyclopropyl-4-pyridyl-quinolones (U.S. Pat. No. 5,330,992), styryl compounds (U.S. Pat. No. 5,217,999), styryl-substituted pyridyl compounds (U.S. Pat. No. 5,302,606), selenoindoles and selenides (WO 94/03427), tricyclic polyhydroxylic compounds (WO 92/21660) and benzylphosphonic acid compounds (WO 91/15495), pyrimidine derivatives (U.S. Pat. No. 5,521,184 and WO 99/03854), indolinone derivatives and pyrrole-substituted indolinones (U.S. Pat. No. 5,792,783, EP 934 931, U.S. Pat. No. 5,834,504, U.S. Pat. No. 5,883,116, U.S. Pat. No. 5,883,113, U.S. Pat. No. 5,886,020, WO 96/40116 and WO 00/38519), as well as bis monocyclic, bicyclic aryl and heteroaryl compounds (EP 584 222, U.S. Pat. No. 5,656,643 and WO 92/20642), quinazoline derivatives (EP 602 851, EP 520 722, U.S. Pat. No. 3,772,295 and U.S. Pat. No. 4,343,940) and aryl and heteroaryl quinazoline (U.S. Pat. No. 5,721,237, U.S. Pat. No. 5,714,493, U.S. Pat. No. 5,710,158 and WO 95/15758).

However, none of these compounds have been described as potent and selective inhibitors of c-kit or of the c-kit pathway.

In connection with the present invention, we have found that compounds corresponding to the 2-(3-aminoaryl)amino-4-aryl-thiazoles are potent and selective inhibitors of c-kit or c-kit pathway. These compounds are good candidates for treating diseases such as autoimmunes diseases, inflammatory diseases, cancer and mastocytosis.

DESCRIPTION

Therefore, the present invention relates to compounds belonging to the 2-(3-amino)arylamino-4-aryl-thiazoles. These compounds are capable of selectively inhibiting signal transduction involving the tyrosine phosphokinase c-kit and mutant forms thereof.

In a first embodiment, the invention is aimed at compounds of formula I, which may represent either free base forms of the substances or pharmaceutically acceptable salts thereof:

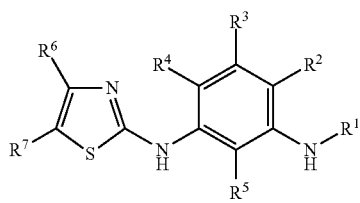

FORMULA I and wherein $R^1$ is:
a) a linear or branched alkyl group containing from 1 to 10 carbon atoms optionally substituted with at least one heteroatom, notably a halogen selected from I, Cl, Br and F, and/or bearing a pendant basic nitrogen functionality;
b) an aryl or heteroaryl group optionally substituted by an alkyl or aryl group optionally substituted with a heteroatom, notably a halogen selected from I, Cl, Br and F or bearing a pendant basic nitrogen functionality;
c) a —CO—NH—R, —CO—R, —CO—OR or a —CO—NRR' group, wherein R and R' are independently chosen from H or an aryl, heteroaryl, alkyl and cycloalkyl group optionally substituted with at least one heteroatom, notably a halogen selected from I, Cl, Br and F, and/or bearing a pendant basic nitrogen functionality;
$R^2$ is hydrogen, halogen or a linear or branched alkyl group containing from 1 to 10 carbon atoms, trifluoromethyl or alkoxy;
$R^3$ is hydrogen, halogen or a linear or branched alkyl group containing from 1 to 10 carbon atoms, trifluoromethyl or alkoxy;
$R^4$ is hydrogen, halogen or a linear or branched alkyl group containing from 1 to 10 carbon atoms, trifluoromethyl or alkoxy;
$R^5$ is hydrogen, halogen or a linear or branched alkyl group containing from 1 to 10 carbon atoms, trifluoromethyl or alkoxy;
$R^6$ is one of the following:
(i) an aryl group such as phenyl or a substituted variant thereof bearing any combination, at any one ring position, of one or more substituents such as halogen, alkyl groups containing from 1 to 10 carbon atoms, trifluoromethyl, and alkoxy;
(ii) a heteroaryl group such as a 2, 3, or 4-pyridyl group, which may additionally bear any combination of one or more substituents such as halogen, alkyl groups containing from 1 to 10 carbon atoms, trifluoromethyl and alkoxy;
(iii) a five-membered ring aromatic heterocyclic group such as for example 2-thienyl, 3-thienyl, 2-thiazolyl, 4-thiazolyl, 5-thiazolyl, which may additionally bear any combination of one or more substituents such as halogen, an alkyl group containing from 1 to 10 carbon atoms, trifluoromethyl, and alkoxy,
iv) H, a halogen selected from I, F, Cl or Br; NH2, NO2 or SO2-R, wherein R is a linear or branched alkyl group containing one or more group such as 1 to 10 carbon atoms, and optionally substituted with at least one heteroatom, notably a halogen selected from I, Cl, Br and F, and/or bearing a pendant basic nitrogen functionality;
and $R^7$ is one of the following:
(i) an aryl group such as phenyl or a substituted variant thereof bearing any combination, at any one ring position, of one or more substituents such as halogen, alkyl groups containing from 1 to 10 carbon atoms, trifluoromethyl, and alkoxy;
(ii) a heteroaryl group such as a 2, 3, or 4-pyridyl group, which may additionally bear any combination of one or more substituents such as halogen, alkyl groups containing from 1 to 10 carbon atoms, trifluoromethyl and alkoxy;
(iii) a five-membered ring aromatic heterocyclic group such as for example 2-thienyl, 3-thienyl, 2-thiazolyl, 4-thiazolyl, 5-thiazolyl, which may additionally bear any combination of one or more substituents such as halogen, an alkyl group containing from 1 to 10 carbon atoms, trifluoromethyl, and alkoxy.
iv) H, a halogen selected from I, F, Cl or Br; NH2, NO2 or SO2-R, wherein R is a linear or branched alkyl group containing one or more group such as 1 to 10 carbon atoms, and optionally substituted with at least one heteroatom, notably a halogen selected from I, Cl, Br and F, and/or bearing a pendant basic nitrogen functionality;

In another preferred embodiment, when $R^1$ has the meaning depicted in c) above, the invention is directed to compounds of the following formula:

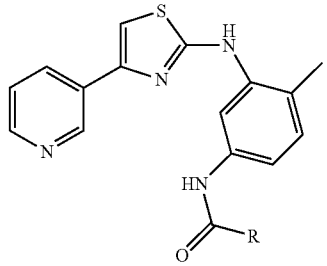

wherein R is H or an organic group that can be selected for example from a linear or branched alkyl group containing from 1 to 10 carbon atoms optionally substituted with at least one heteroatom or bearing a pendant basic nitrogen functionality; a cycloalkyl, an aryl or heteroaryl group optionally substituted by an alkyl, a cycloalkyl, an aryl or heteroaryl group optionally substituted with a heteroatom, notably a halogen selected from I, Cl, Br and F and/or bearing a pendant basic nitrogen functionality.

Among the particular compounds in which R1 has the meaning as depicted in c) above, the invention is directed to amide-aniline compounds of the following formula:

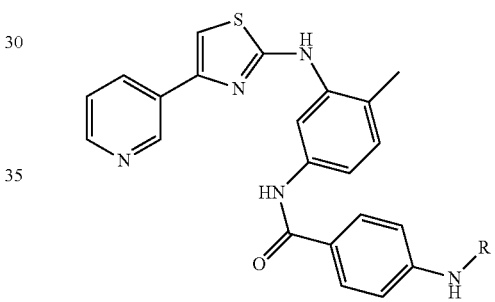

wherein R is H or an organic group that can be selected for example from a linear or branched alkyl group containing from 1 to 10 carbon atoms optionally substituted with at least one heteroatom or bearing a pendant basic nitrogen functionality; a cycloalkyl, an aryl or heteroaryl group optionally substituted with a heteroatom, notably a halogen selected from I, Cl, Br and F and/or bearing a pendant basic nitrogen functionality; or a cycloalkyl, an aryl or heteroaryl group optionally substituted with a cycloalkyl, an aryl or heteroaryl group optionally substituted with a heteroatom, notably a halogen selected from I, Cl, Br and F and/or bearing a pendant basic nitrogen functionality;
a —SO2-R group wherein R is an alkyl, cycloalkyl, aryl or heteroaryl optionally substituted with an heteroatom, notably a halogen selected from I, Cl, Br and F and/or bearing a pendant basic nitrogen functionality; or a —CO—R or a —CO—NRR' group, wherein R and R' are independently chosen from H, an alkyl, a cycloalkyl, an aryl or heteroaryl group optionally substituted with at least one heteroatom, notably selected from I, Cl, Br and F, and/or bearing a pendant basic nitrogen functionality.

Among the particular compounds in which R1 has the meaning as depicted in c) above, the invention is directed to amide-benzylamine compounds of the following formula:

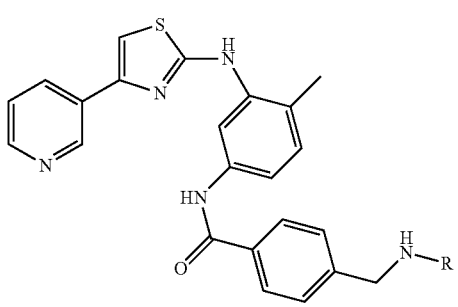

wherein R is H or an organic group that can be selected for example from a linear or branched alkyl group containing from 1 to 10 carbon atoms optionally substituted with at least one heteroatom, notably a halogen selected from I, Cl, Br and F, and/or bearing a pendant basic nitrogen functionality; a cycloalkyl, aryl or heteroaryl group optionally substituted with an heteroatom, notably a halogen selected from I, Cl, Br and F or bearing a pendant basic nitrogen functionality; or an alkyl, cycloalkyl, aryl or heteroaryl group substituted by a alkyl, cycloalkyl, aryl or heteroaryl group optionally substituted with a heteroatom, notably a halogen selected from I, Cl, Br and F or bearing a pendant basic nitrogen functionality; a —SO2-R group wherein R is an alkyl, cycloalkyl, aryl or heteroaryl group optionally substituted with an heteroatom, notably a halogen selected from I, Cl, Br and F or bearing a pendant basic nitrogen functionality; or a —CO—R or a —CO—NRR' group, wherein R and R' are independently chosen from H or an aryl heteroaryl, alkyl and cycloalkyl group optionally substituted with at least one heteroatom and/or bearing a pendant basic nitrogen functionality.

Among the particular compounds in which R1 has the meaning as depicted in c) above, the invention is directed to amide-phenol compounds of the following formula:

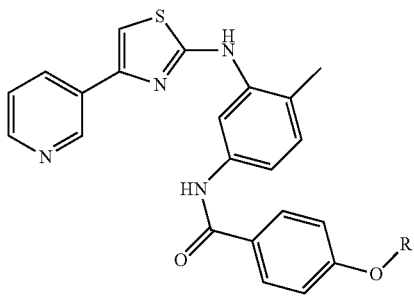

wherein R is H or an organic group that can be selected for example from a linear or branched alkyl group containing from 1 to 10 carbon atoms optionally substituted with at least one heteroatom, notably a halogen selected from I, Cl, Br and F, and/or bearing a pendant basic nitrogen functionality; a cycloalkyl, aryl or heteroaryl group optionally substituted with a heteroatom, notably a halogen selected from I, Cl, Br and F and/or bearing a pendant basic nitrogen functionality; or an alkyl, cycloalkyl, aryl or heteroaryl group substituted by a alkyl, cycloalkyl, aryl or heteroaryl group optionally substituted with a heteroatom, notably a halogen selected from I, Cl, Br and F and/or bearing a pendant basic nitrogen functionality;
a —SO2-R group wherein R is an alkyl, cycloalkyl, aryl or heteroaryl group optionally substituted with an heteroatom, notably a halogen selected from I, Cl, Br and F and/or bearing a pendant basic nitrogen functionality; or a —CO—R or a —CO—NRR' group, wherein R and R' are independently chosen from H or an aryl, heteroaryl, alkyl and cycloalkyl group optionally substituted with at least one heteroatom and/or bearing a pendant basic nitrogen functionality.

Among the particular compounds in which R1 has the meaning as depicted in c) above, the invention is directed to urea compounds of the following formula:

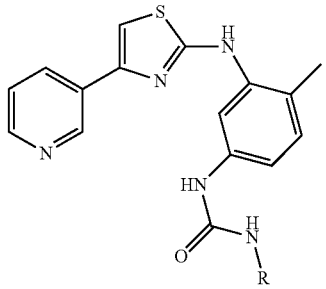

wherein R is H or an organic group that can be selected for example from a linear or branched alkyl group containing from 1 to 10 carbon atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality.

Among the particular compounds in which R1 has the meaning as depicted in a) and b) above, the invention is directed to N-Aminoalkyl-N'-thiazol-2-yl-benzene-1,3-diamine compounds of the following formula:

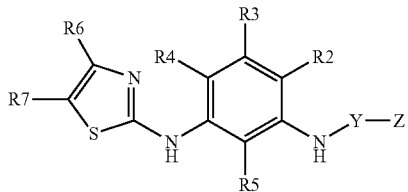

wherein Y is a linear or branched alkyl group containing from 1 to 10 carbon atoms;
wherein Z represents an aryl or heteroaryl group, optionally substituted at one or more ring position with any permutation of the following groups:
  a halogen such as F, Cl, Br, I;
  a linear or branched alkyl group containing from 1 to 10 carbon atoms atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

an O—R, where R is a linear or branched alkyl group containing from 1 to 10 carbon atoms atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

an NRaRb, where Ra and Rb represents a hydrogen, or a linear or branched alkyl group containing from 1 to 10 carbon atoms atoms optionally substituted with at least one heteroatom (for example a halogen) and/or bearing a pendant basic nitrogen functionality or a cycle; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

a COOR, where R is a linear or branched alkyl group containing from 1 to 10 carbon atoms atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

a CONRaRb, where Ra and Rb are a hydrogen or a linear or branched alkyl group containing from 1 to 10 carbon atoms atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

an NHCOR, where R is a linear or branched alkyl group containing from 1 to 10 carbon atoms atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

an NHCOOR, where R is a linear or branched alkyl group containing from 1 to 10 carbon atoms atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

an NHCONRaRb, where Ra and Rb are a hydrogen or a linear or branched alkyl group containing from 1 to 10 carbon atoms atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

an $OSO_2R$, where R is a linear or branched alkyl group containing from 1 to 10 carbon atoms atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

an $NRaOSO_2Rb$, where Ra and Rb are a linear or branched alkyl group containing from 1 to 10 carbon atoms atoms optionally substituted with at least one heteroatom (for example a halogen) and/or bearing a pendant basic nitrogen functionality; Ra can also be a hydrogen; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

$R^2$ is hydrogen, halogen or a linear or branched alkyl group containing from 1 to 10 carbon atoms, trifluoromethyl or alkoxy;

$R^3$ is hydrogen, halogen or a linear or branched alkyl group containing from 1 to 10 carbon atoms, trifluoromethyl or alkoxy;

$R^4$ is hydrogen, halogen or a linear or branched alkyl group containing from 1 to 10 carbon atoms, trifluoromethyl or alkoxy;

$R^5$ is hydrogen, halogen or a linear or branched alkyl group containing from 1 to 10 carbon atoms, trifluoromethyl or alkoxy;

$R^6$ is one of the following:
(i) an aryl group such as phenyl or a substituted variant thereof bearing any combination, at any one ring position, of one or more substituents such as halogen, alkyl groups containing from 1 to 10 carbon atoms, trifluoromethyl, and alkoxy;
(ii) a heteroaryl group such as a 2, 3, or 4-pyridyl group, which may additionally bear any combination of one or more substituents such as halogen, alkyl groups containing from 1 to 10 carbon atoms, trifluoromethyl and alkoxy;
(iii) a five-membered ring aromatic heterocyclic group such as for example 2-thienyl, 3-thienyl, 2-thiazolyl, 4-thiazolyl, 5-thiazolyl, which may additionally bear any combination of one or more substituents such as halogen, an alkyl group containing from 1 to 10 carbon atoms, trifluoromethyl, and alkoxy.
iv) H, a halogen selected from I, F, Cl or Br; NH2, NO2 or SO2-R, wherein R is a linear or branched alkyl group containing one or more group such as 1 to 10 carbon atoms, and optionally substituted with at least one heteroatom, notably a halogen selected from I, Cl, Br and F, and/or bearing a pendant basic nitrogen functionality;
and $R^7$ is one of the following:
(i) an aryl group such as phenyl or a substituted variant thereof bearing any combination, at any one ring position, of one or more substituents such as halogen, alkyl groups containing from 1 to 10 carbon atoms, trifluoromethyl, and alkoxy;
(ii) a heteroaryl group such as a 2, 3, or 4-pyridyl group, which may additionally bear any combination of one or more substituents such as halogen, alkyl groups containing from 1 to 10 carbon atoms, trifluoromethyl and alkoxy;
(iii) a five-membered ring aromatic heterocyclic group such as for example 2-thienyl, 3-thienyl, 2-thiazolyl, 4-thiazolyl, 5-thiazolyl, which may additionally bear any combination of one or more substituents such as halogen, an alkyl group containing from 1 to 10 carbon atoms, trifluoromethyl, and alkoxy.
iv) H, an halogen selected from I, F, Cl or Br; NH2, NO2 or SO2-R, wherein R is a linear or branched alkyl group containing one or more group such as 1 to 10 carbon atoms, and optionally substituted with at least one heteroatom, notably a halogen selected from I, Cl, Br and F, and/or bearing a pendant basic nitrogen functionality An example of preferred compounds of the above formula is depicted below:
001: 4-{[4-Methyl-3-(4-pyridin-3-yl-thiazol-2-ylamino)-phenylamino]-methyl}-benzoic acid methyl ester Among the compounds of formula I, the invention is particularly embodied by the compounds of the following formula II:

FORMULA II wherein X is R or NRR' and wherein R and R' are independently chosen from H, an aryl, a heteroaryl, an alkyl, or a cycloalkyl group optionally substituted with at least one heteroatom, such as for example a halogen chosen from F, I, Cl and Br and optionally bearing a pendant basic nitrogen functionality; or an aryl, a heteroaryl, an alkyl or a cycloalkyl group substituted with an aryl, a heteroaryl, an alkyl or a cycloalkyl group optionally substituted with at least one heteroatom, such as for example a halogen chosen from F, I, Cl and Br and optionally bearing a pendant basic nitrogen functionality,
$R^2$ is hydrogen, halogen or a linear or branched alkyl group containing from 1 to 10 carbon atoms, trifluoromethyl or alkoxy;
$R^3$ is hydrogen, halogen or a linear or branched alkyl group containing from 1 to 10 carbon atoms, trifluoromethyl or alkoxy;
$R^4$ is hydrogen, halogen or a linear or branched alkyl group containing from 1 to 10 carbon atoms, trifluoromethyl or alkoxy;
$R^5$ is hydrogen, halogen or a linear or branched alkyl group containing from 1 to 10 carbon atoms, trifluoromethyl or alkoxy;
$R^6$ is one of the following:
(i) an aryl group such as phenyl or a substituted variant thereof bearing any combination, at any one ring position, of one or more substituents such as halogen, alkyl groups containing from 1 to 10 carbon atoms, trifluoromethyl, and alkoxy;
(ii) a heteroaryl group such as a 2, 3, or 4-pyridyl group, which may additionally bear any combination of one or more substituents such as halogen, alkyl groups containing from 1 to 10 carbon atoms, trifluoromethyl and alkoxy;
(iii) a five-membered ring aromatic heterocyclic group such as for example 2-thienyl, 3-thienyl, 2-thiazolyl, 4-thiazolyl, 5-thiazolyl, which may additionally bear any combination of one or more substituents such as halogen, an alkyl group containing from 1 to 10 carbon atoms, trifluoromethyl, and alkoxy.
iv) H, a halogen selected from I, F, Cl or Br; NH2, NO2 or SO2-R, wherein R is a linear or branched alkyl group containing one or more group such as 1 to 10 carbon atoms, and optionally substituted with at least one heteroatom, notably a halogen selected from I, Cl, Br and F, and/or bearing a pendant basic nitrogen functionality.

In another alternative, substituent $R^6$, which in the formula II is connected to position 4 of the thiazole ring, may instead occupy position 5 of the thiazole ring.

Among the preferred compounds corresponding formula II, the invention is directed to compounds in which X is a substituted alkyl, aryl or heteroaryl group bearing a pendant basic nitrogen functionality represented for example by the structures a to f shown below, wherein the wavy line corresponds to the point of attachment to core structure of formula II:

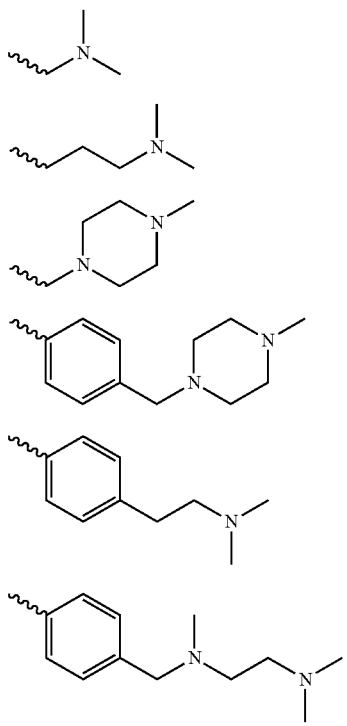

a b c d e f

Among group a to f, X (see formula II) is preferentially group d.

Furthermore, among the preferred compounds of formula I or II, the invention concerns the compounds in which $R^2$ and $R^3$ are hydrogen. Preferentially, $R^4$ is a methyl group and $R^5$ is H. In addition, $R^6$ is preferentially a 3-pyridyl group (cf. structure g below), or a 4-pyridyl group (cf. structure h below). The wavy line in structure g and h correspond to the point of attachment to the core structure of formula I or II.

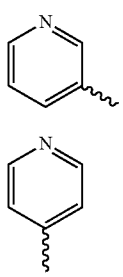

g h

Thus, the invention contemplates:

1—A compound of formula II as depicted above, wherein X is group d and $R^6$ is a 3-pyridyl group.
2—A compound of formula II as depicted above, wherein X is group d and $R^4$ is a methyl group.
3—A compound of formula I or II as depicted above, wherein $R^1$ is group d and $R^2$ is H.
4—A compound of formula I or II as depicted above, wherein $R^1$ is group d and $R^3$ is H.
5—A compound of formula I or II as depicted above, wherein $R^1$ is group d and $R^2$ and/or $R^3$ and/or $R^5$ is H.
6—A compound of formula I or II as depicted above, wherein $R^6$ is a 3-pyridyl group and $R^3$ is a methyl group.
7—A compound of formula I or II as depicted above, wherein $R^6$ is a 3-pyridyl group and $R^2$ is H.
8—A compound of formula I or II as depicted above, wherein $R^2$ and/or $R^3$ and/or $R^5$ is H and $R^4$ is a methyl group.
9—A compound of formula I or II as depicted above wherein $R^2$ and/or $R^3$ and/or $R^5$ is H, $R^4$ is a methyl group and $R^6$ is a 3-pyridyl group.

Among the compounds of formula II, the invention is particularly embodied by the compounds wherein R2, R3, R5 are hydrogen, corresponding to the following formula II-1:

FORMULA II-1

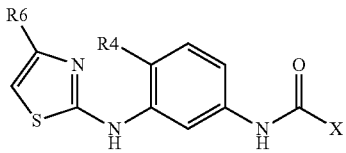

wherein X is R or NRR' and wherein R and R' are independently chosen from H or an organic group that can be selected for example from a linear or branched alkyl group containing from 1 to 10 carbon atoms optionally substituted with at least one heteroatom or bearing a pendant basic nitrogen functionality; a cycloalkyl, an aryl or heteroaryl group optionally substituted with an heteroatom, notably a halogen selected from I, Cl, Br and F or bearing a pendant basic nitrogen functionality; or a cycloalkyl, an aryl or heteroaryl group optionally substituted with a cycloalkyl, an aryl or heteroaryl group optionally substituted with an heteroatom, notably a halogen selected from I, Cl, Br and F or bearing a pendant basic nitrogen functionality;

a —SO2-R group wherein R is an alkyl, cycloalkyl, aryl or heteroaryl optionally substituted with a heteroatom, notably a halogen selected from I, Cl, Br and F or bearing a pendant basic nitrogen functionality; or a —CO—R or a —CO—NRR' group, wherein R and R' are independently chosen from H, an alkyl, a cycloalkyl, an aryl or heteroaryl group optionally substituted with at least one heteroatom, notably selected from I, Cl, Br and F, and/or bearing a pendant basic nitrogen functionality $R^4$ is hydrogen, halogen or a linear or branched alkyl group containing from 1 to 10 carbon atoms, trifluoromethyl or alkoxy;

$R^6$ is one of the following:

(i) an aryl group such as phenyl or a substituted variant thereof bearing any combination, at any one ring position, of one or more substituents such as halogen, alkyl groups containing from 1 to 10 carbon atoms, trifluoromethyl, and alkoxy;

(ii) a heteroaryl group such as a 2, 3, or 4-pyridyl group, which may additionally bear any combination of one or more substituents such as halogen, alkyl groups containing from 1 to 10 carbon atoms, trifluoromethyl and alkoxy;

(iii) a five-membered ring aromatic heterocyclic group such as for example 2-thienyl, 3-thienyl, 2-thiazolyl, 4-thiazolyl, 5-thiazolyl, which may additionally bear any combination of one or more substituents such as halogen, an alkyl group containing from 1 to 10 carbon atoms, trifluoromethyl, and alkoxy.

(iv) H, a halogen selected from I, F, Cl or Br; NH2, NO2 or SO2-R, wherein R is a linear or branched alkyl group containing one or more group such as 1 to 10 carbon atoms, and optionally substituted with at least one heteroatom, notably a halogen selected from I, Cl, Br and F, and/or bearing a pendant basic nitrogen functionality In another alternative, substituent R6, which in the formula II is connected to position 4 of the thiazole ring, may instead occupy position 5 of the thiazole ring.

EXAMPLES

002: 2-(2-methyl-5-amino)phenyl-4-(3-pyridyl)-thiazole

003: 4-(4-Methyl-piperazin-1-ylmethyl)-N-[3-(4-pyridin-3-yl-thiazol-2-ylamino)-phenyl]-benzamide

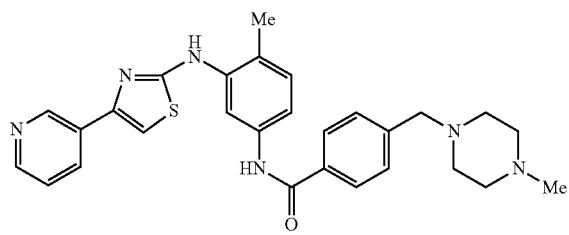 [SMILES: Cc1ccc(NC(=O)c2ccc(CN3CCN(C)CC3)cc2)cc1Nc1nc(-c2cccnc2)cs1]

004: N-[4-Methyl-3-(4-phenyl-thiazol-2-ylamino)-phenyl]-4-(4-methyl-piperazin-1-ylmethyl)-benzamide

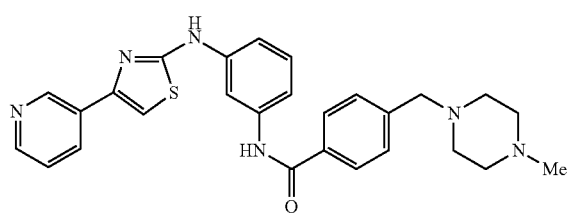 [SMILES: CN1CCN(Cc2ccc(C(=O)Nc3cccc(Nc4nc(-c5cccnc5)cs4)c3)cc2)CC1]

005: N-[3-([2,4']Bithiazolyl-2'-ylamino)-4-methyl-phenyl]-4-(4-methyl-piperazin-1-ylmethyl)-benzamide

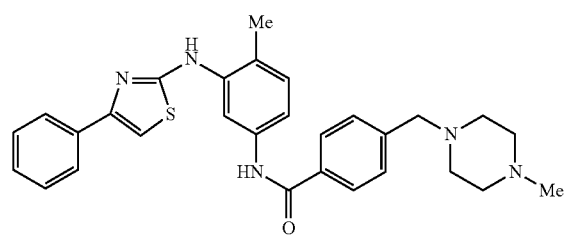 [SMILES: Cc1ccc(NC(=O)c2ccc(CN3CCN(C)CC3)cc2)cc1Nc1nc(-c2ccccc2)cs1]

006: 4-(4-Methyl-piperazin-1-ylmethyl)-N-[4-methyl-3-(4-pyrazin-2-yl-thiazol-2-ylamino)-phenyl]-benzamide

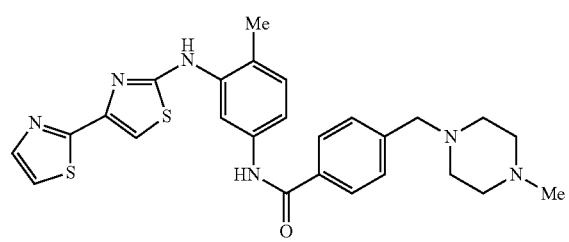 [SMILES: Cc1ccc(NC(=O)c2ccc(CN3CCN(C)CC3)cc2)cc1Nc1nc(-c2nccs2)cs1]

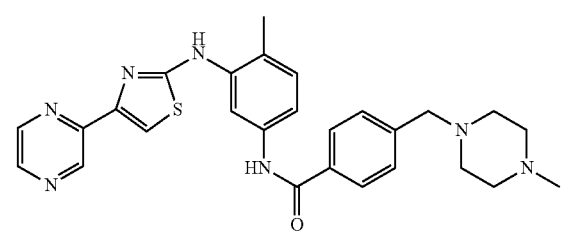 [SMILES: Cc1ccc(NC(=O)c2ccc(CN3CCN(C)CC3)cc2)cc1Nc1nc(-c2cnccn2)cs1]

007: 2-[5-(3-Iodo-benzoylamino)-2-methyl-phenylamino]-thiazole-4-carboxylic acid ethyl ester

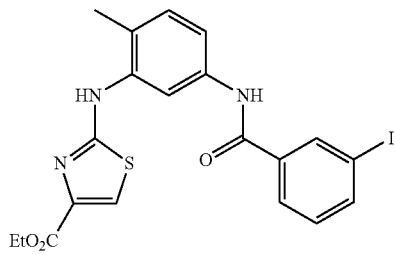 [SMILES: CCOC(=O)c1csc(Nc2cc(NC(=O)c3cccc(I)c3)ccc2C)n1]

008: 2-{2-Methyl-5-[4-(4-methyl-piperazin-1-ylmethyl)-benzoylamino]-phenylamino}-thiazole-4-carboxylic acid ethyl ester

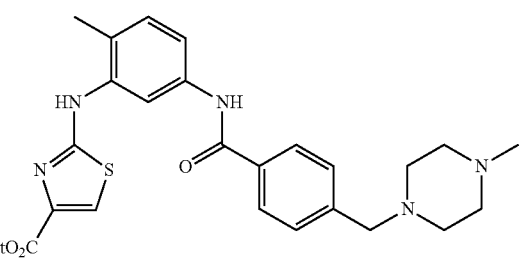

027: 2-(2-chloro-5-amino)phenyl-4-(3-pyridyl)-thiazole

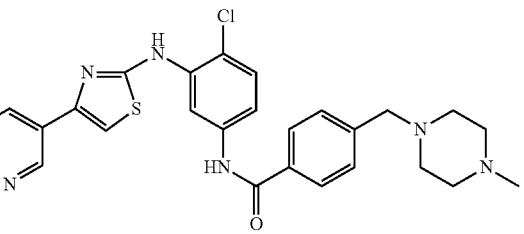

128: 3-Bromo-N-{3-[4-(4-chloro-phenyl)-5-methyl-thiazol-2-ylamino]-4-methyl-phenyl}-benzamide

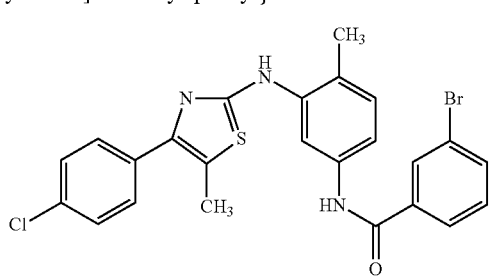

129: {3-[4-(4-Chloro-phenyl)-5-methyl-thiazol-2-ylamino]-4-methyl-phenyl}-carbamic acid isobutyl ester

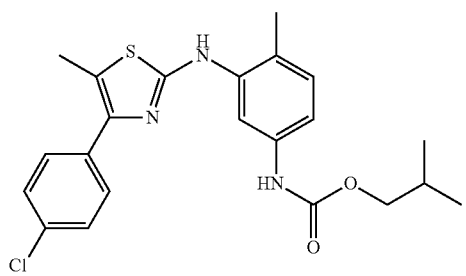 [SMILES: Cc1ccc(NC(=O)OCC(C)C)cc1Nc1nc(-c2ccc(Cl)cc2)c(C)s1]

130: 2-[5-(3-Bromo-benzoylamino)-2-methyl-phenylamino]-5-(4-chloro-phenyl)-thiazole-4-carboxylic acid ethyl ester

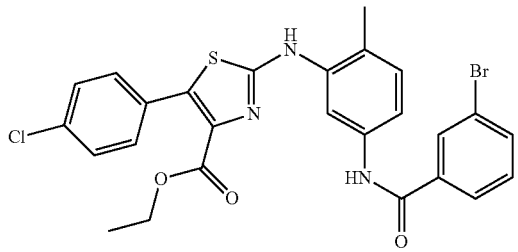 [SMILES: CCOC(=O)c1nc(Nc2cc(NC(=O)c3cccc(Br)c3)ccc2C)sc1-c1ccc(Cl)cc1]

131: 2-[5-(3-Bromo-benzoylamino)-2-methyl-phenylamino]-5-(4-chloro-phenyl)-thiazole-4-carboxylic acid (2-dimethylamino-ethyl)-amide

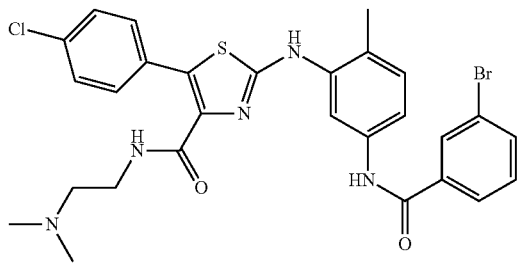 [SMILES: Cc1ccc(NC(=O)c2cccc(Br)c2)cc1Nc1nc(C(=O)NCCN(C)C)c(-c2ccc(Cl)cc2)s1]

110: N-{3-[4-(4-Methoxy-phenyl)-thiazol-2-ylamino]-4-methyl-phenyl}-4-(4-methyl-piperazin-1 ylmethyl)-benzamide

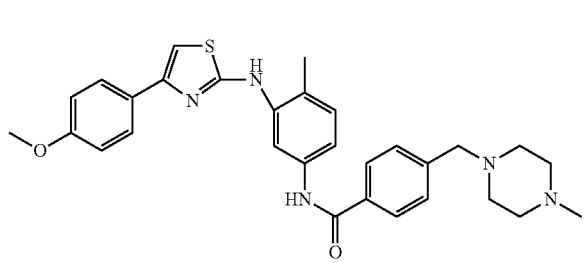

116: 4-(4-Methyl-piperazin-1-ylmethyl)-N-{4-methyl-3-[4-(3-trifluoromethyl-phenyl)-thiazol-2-ylamino]-phenyl}-benzamide

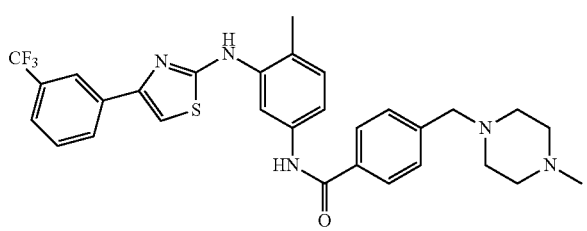 [SMILES: Cc1ccc(NC(=O)c2ccc(CN3CCN(C)CC3)cc2)cc1Nc1nc(-c2cccc(C(F)(F)F)c2)cs1]

117: N-{4-Methyl-3-[4-(3-nitro-phenyl)-thiazol-2-ylamino]-phenyl}-4-(4-methyl-piperazin-1-ylmethyl)-benzamide

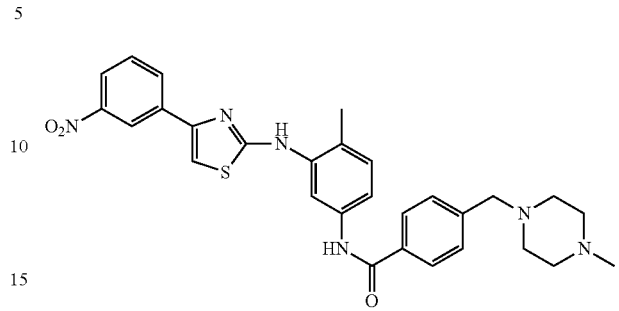

124: N-{3-[4-(2,5-Dimethyl-phenyl)-thiazol-2-ylamino]-4-methyl-phenyl}-4-(4-methyl-piperazin-1-ylmethyl)-benzamide

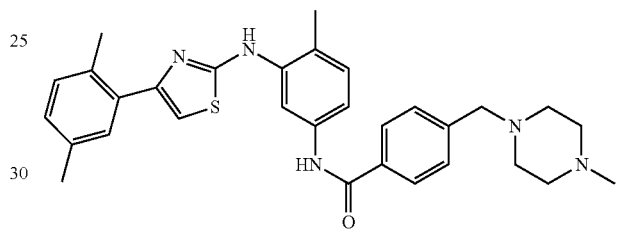

108: N-{3-[4-(4-Chloro-phenyl)-thiazol-2-ylamino]-4-methyl-phenyl}-4-(4-methyl-piperazin-1-ylmethyl)-benzamide

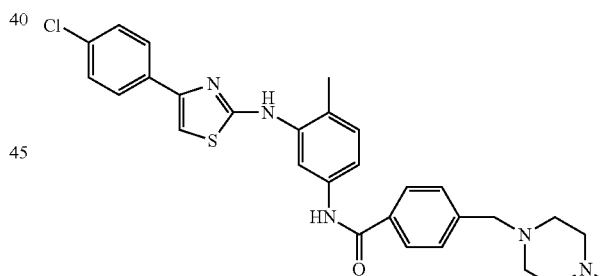

113: N-{3-[4-(3-Methoxy-phenyl)-thiazol-2-ylamino]-4-methyl-phenyl}-4-(4-methyl-piperazin-1-ylmethyl)-benzamide

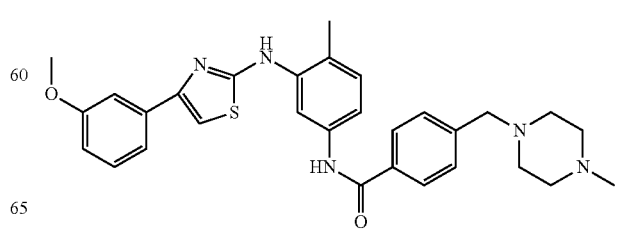

063: N-[4-Methyl-3-(4-pyridin-3-yl-thiazol-2-ylamino)-phenyl]-isonicotinamide

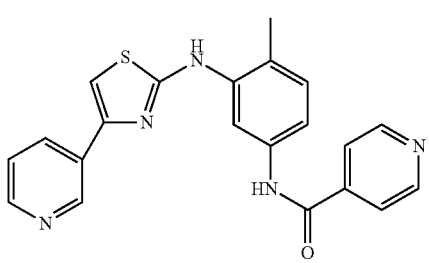 [SMILES: Cc1ccc(NC(=O)c2ccncc2)cc1Nc1nc(-c2cccnc2)cs1]

064: 2,6-Dichloro-N-[4-methyl-3-(4-pyridin-3-yl-thiazol-2-ylamino)-phenyl]-isonicotinamide

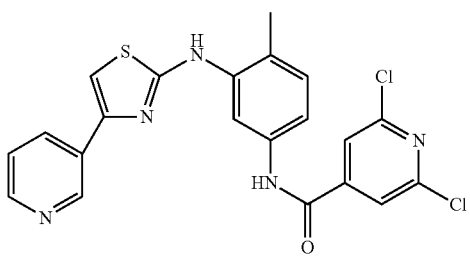 [SMILES: Cc1ccc(NC(=O)c2cc(Cl)nc(Cl)c2)cc1Nc1nc(-c2cccnc2)cs1]

091: 3-Phenyl-propynoic acid [4-methyl-3-(4-pyridin-3-yl-thiazol-2-ylamino)-phenyl]-amide

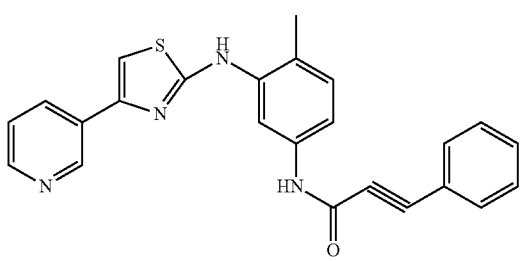 [SMILES: Cc1ccc(NC(=O)C#Cc2ccccc2)cc1Nc1nc(-c2cccnc2)cs1]

092: Cyclohexanecarboxylic acid [4-methyl-3-(4-pyridin-3-yl-thiazol-2-ylmethyl)-phenyl]-amide

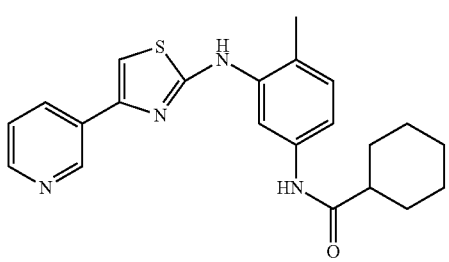 [SMILES: Cc1ccc(NC(=O)C2CCCCC2)cc1Nc1nc(-c2cccnc2)cs1]

093: 5-[4-Methyl-3-(4-pyridin-3-yl-thiazol-2-ylamino)-phenylcarbamoyl]-pentanoic acid ethyl ester

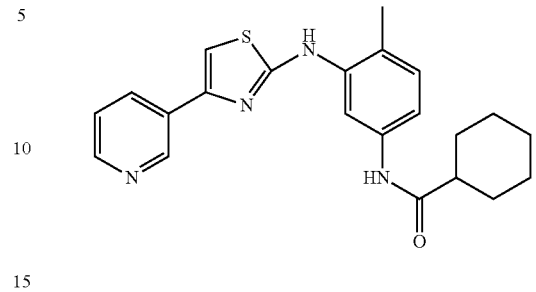

094: 1-Methyl-cyclohexanecarboxylic acid [4-methyl-3-(4-pyridin-3-yl-thiazol-2-ylmethyl)-phenyl]-amide

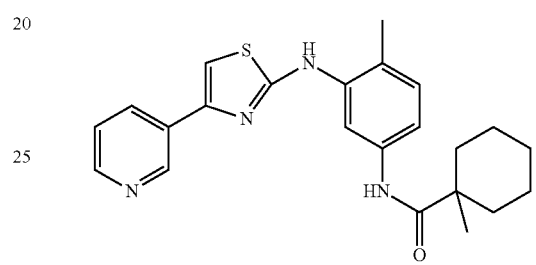

095: 4-tert-Butyl-cyclohexanecarboxylic acid [4-methyl-3-(4-pyridin-3-yl-thiazol-2-ylamino)-phenyl]-amide

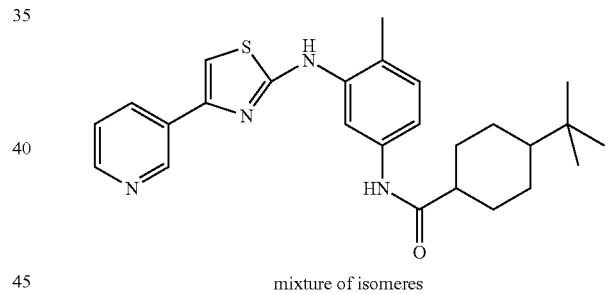

mixture of isomeres cis/trans

096: N-[4-Methyl-3-(4-pyridin-3-yl-thiazol-2-ylamino)-phenyl]-4-morpholin-4-yl-butyramide

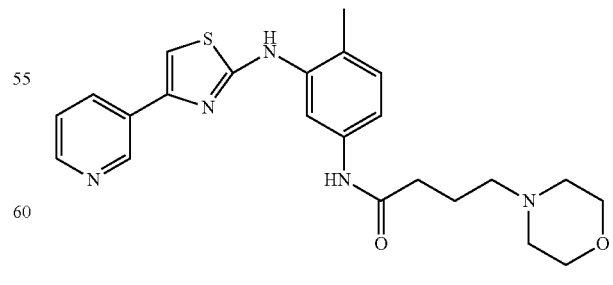

beige powder mp: 116-120° C.

$^1$H RMN (DMSO-d$^6$) δ=1.80-2.00 (m, 2H); 2.29 (s, 3H); 2.30-2.45 (m, 6H); 3.55-3.65 (m, 6H); 7.15-7.25 (m, 2H);

7.46-7.50 (m, 2H); 7.52 (s, 1H); 8.35 (d, J=6.2 Hz, 1H); 8.55 (dd, J=1.5 Hz, J=4.7 Hz, 2H); 9.22 (s, 1H); 9.45 (s, 1H); 9.93 (s, 1H)

Among the compounds of formula II, the invention is particularly embodied by the compounds wherein X is a urea group, a —CO—NRR' group, corresponding to the [3-(thiazol-2-ylamino)-phenyl]-urea family and the following formula II-2:

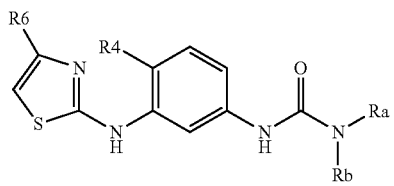

FORMULA II-2 wherein Ra, Rb are independently chosen from H or an organic group that can be selected for example from a linear or branched alkyl group containing from 1 to 10 carbon atoms optionally substituted with at least one heteroatom and/or bearing a pendant basic nitrogen functionality; a cycloalkyl, an aryl or heteroaryl group optionally substituted with a heteroatom, notably a halogen selected from I, Cl, Br and F or bearing a pendant basic nitrogen functionality; or a cycloalkyl, an aryl or heteroaryl group optionally substituted with a cycloalkyl, an aryl or heteroaryl group optionally substituted with a heteroatom, notably a halogen selected from I, Cl, Br and F or bearing a pendant basic nitrogen functionality; a —SO2-R group wherein R is an alkyl, cycloalkyl, aryl or heteroaryl optionally substituted with an heteroatom, notably a halogen selected from I, Cl, Br and F or bearing a pendant basic nitrogen functionality; or a —CO—R or a —CO—NRR' group, wherein R and R' are independently chosen from H, an alkyl, a cycloalkyl, an aryl or heteroaryl group optionally substituted with at least one heteroatom, notably selected from I, Cl, Br and F, or bearing a pendant basic nitrogen functionality.

$R^4$ is hydrogen, halogen or a linear or branched alkyl group containing from 1 to 10 carbon atoms, trifluoromethyl or alkoxy;

$R^6$ is one of the following:

(i) an aryl group such as phenyl or a substituted variant thereof bearing any combination, at any one ring position, of one or more substituents such as halogen, alkyl groups containing from 1 to 10 carbon atoms, trifluoromethyl, and alkoxy;

(ii) a heteroaryl group such as a 2, 3, or 4-pyridyl group, which may additionally bear any combination of one or more substituents such as halogen, alkyl groups containing from 1 to 10 carbon atoms, trifluoromethyl and alkoxy;

(iii) a five-membered ring aromatic heterocyclic group such as for example 2-thienyl, 3-thienyl, 2-thiazolyl, 4-thiazolyl, 5-thiazolyl, which may additionally bear any combination of one or more substituents such as halogen, an alkyl group containing from 1 to 10 carbon atoms, trifluoromethyl, and alkoxy.

iv) H, a halogen selected from I, F, Cl or Br; NH2, NO2 or SO2-R, wherein R is a linear or branched alkyl group containing one or more group such as 1 to 10 carbon atoms, and optionally substituted with at least one heteroatom, notably a halogen selected from I, Cl, Br and F, and/or bearing a pendant basic nitrogen functionality

EXAMPLES

009: 1-(4-Methoxy-phenyl)-3-[4-methyl-3-(4-pyridin-3-yl-thiazol-2-ylamino)-phenyl]-urea

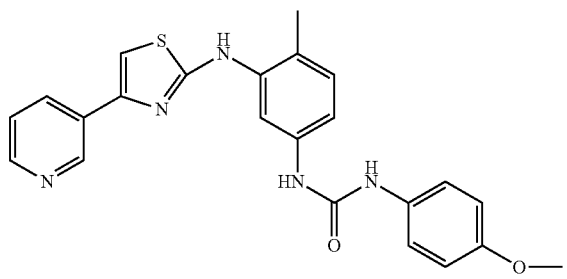 [SMILES: COc1ccc(NC(=O)Nc2ccc(C)c(Nc3nc(-c4cccnc4)cs3)c2)cc1]

010: 1-(4-Bromo-phenyl)-3-[4-methyl-3-(4-pyridin-3-yl-thiazol-2-ylamino)-phenyl]-urea

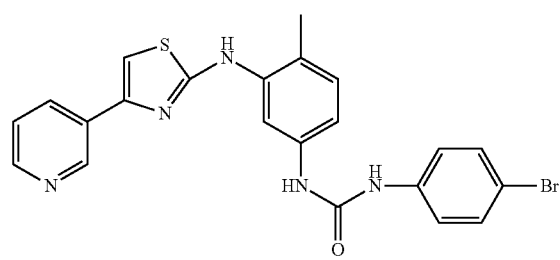 [SMILES: Cc1ccc(NC(=O)Nc2ccc(Br)cc2)cc1Nc1nc(-c2cccnc2)cs1]

011: 1-[4-Methyl-3-(4-pyridin-3-yl-thiazol-2-ylamino)-phenyl]-3-(4-trifluoromethyl-phenyl)-urea

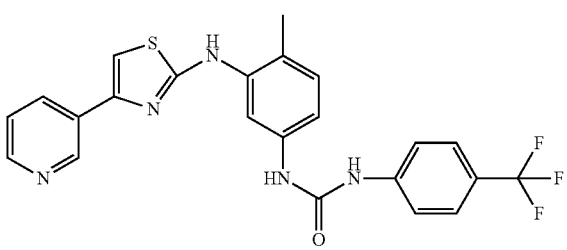 [SMILES: Cc1ccc(NC(=O)Nc2ccc(C(F)(F)F)cc2)cc1Nc1nc(-c2cccnc2)cs1]

012: 1-(4-Fluoro-phenyl)-3-[4-methyl-3-(4-pyridin-3-yl-thiazol-2-ylamino)-phenyl]-urea

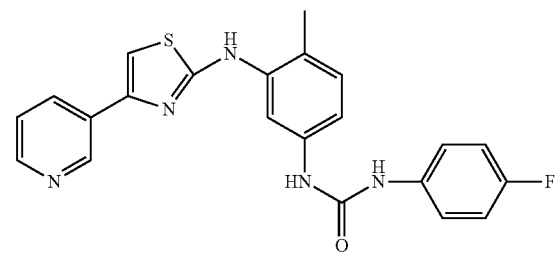 [SMILES: Cc1ccc(NC(=O)Nc2ccc(F)cc2)cc1Nc1nc(-c2cccnc2)cs1]

013: 1-[4-Methyl-3-(4-pyridin-3-yl-thiazol-2-ylamino)-phenyl]-3-(3,4,5-trimethoxy-phenyl)-urea

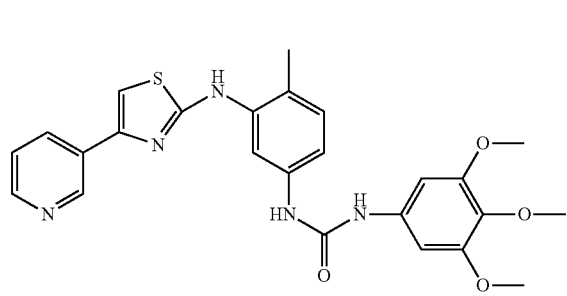 [SMILES: COc1cc(NC(=O)Nc2ccc(C)c(Nc3nc(-c4cccnc4)cs3)c2)cc(OC)c1OC]

014: 4-{3-[4-Methyl-3-(4-pyridin-3-yl-thiazol-2-ylamino)-phenyl]-ureido}-benzoic acid ethyl ester

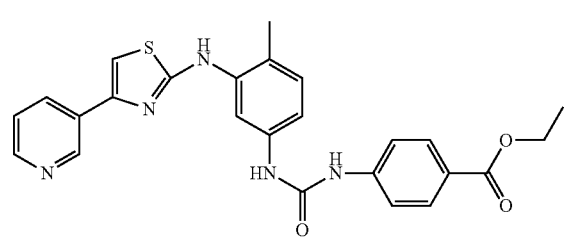 [SMILES: CCOC(=O)c1ccc(NC(=O)Nc2ccc(C)c(Nc3nc(-c4cccnc4)cs3)c2)cc1]

015: 1-[4-Methyl-3-(4-pyridin-3-yl-thiazol-2-ylamino)-phenyl]-3-thiophen-2-yl-urea

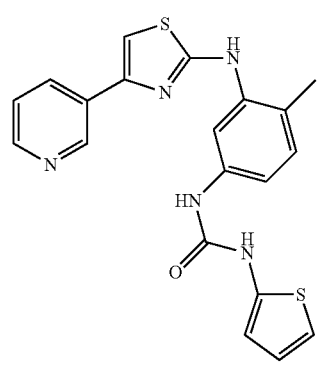 [SMILES: Cc1ccc(NC(=O)Nc2cccs2)cc1Nc1nc(-c2cccnc2)cs1]

016: 1-Cyclohexyl-1-(N-Cyclohexyl-formamide)-3-[4-methyl-3-(4-pyridin-3-yl-thiazol-2-ylamino)-phenyl]-urea

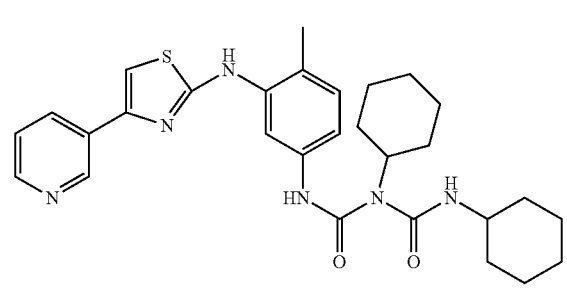 [SMILES: Cc1ccc(NC(=O)N(C(=O)NC2CCCCC2)C2CCCCC2)cc1Nc1nc(-c2cccnc2)cs1]

017: 1-(2,4-Dimethoxy-phenyl)-3-[4-methyl-3-(4-pyridin-3-yl-thiazol-2-ylamino)-phenyl]-urea

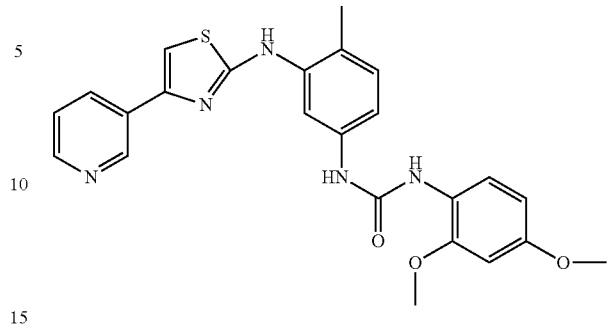

018: 1-(2-Iodo-phenyl)-1-(N-(2-Iodo-phenyl)-formamide)-3-[4-methyl-3-(4-pyridin-3-yl-thiazol-2-ylamino)-phenyl]-urea

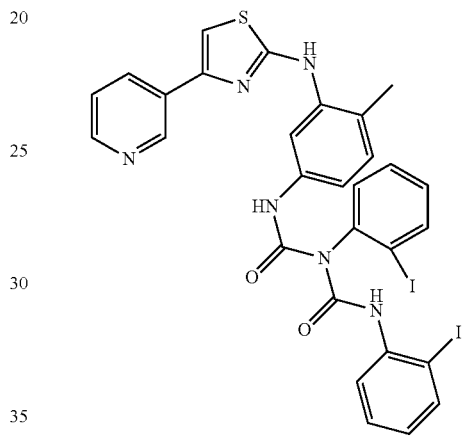

019: 1-(3,5-Dimethyl-isoxazol-4-yl)-3-[4-methyl-3-(4-pyridin-3-yl-thiazol-2-ylamino)-phenyl]-urea

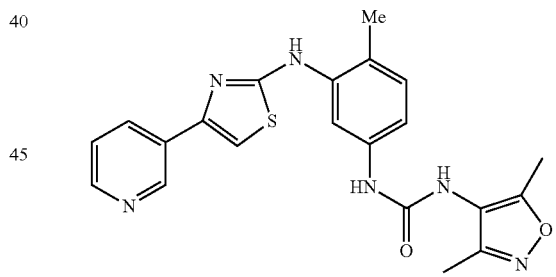

020: 1-(2-Iodo-phenyl)-3-[4-methyl-3-(4-pyridin-3-yl-thiazol-2-ylamino)-phenyl]-urea

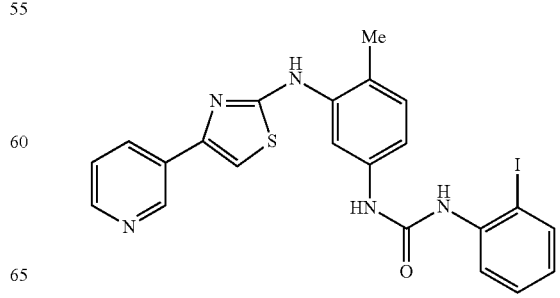

021: 1-(4-Difluoromethoxy-phenyl)-3-[4-methyl-3-(4-pyridin-3-yl-thiazol-2-ylamino)-phenyl]-urea

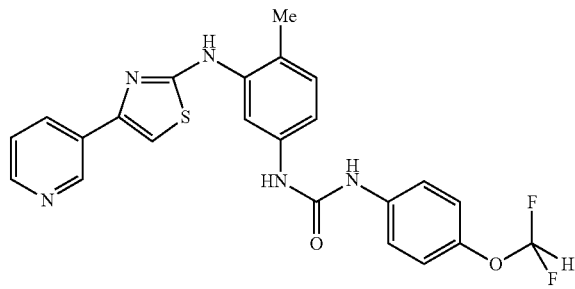 [SMILES: Cc1ccc(NC(=O)Nc2ccc(OC(F)F)cc2)cc1Nc1nc(-c2cccnc2)cs1]

022: 1-(4-Dimethylamino-phenyl)-3-[4-methyl-3-(4-pyridin-3-yl-thiazol-2-ylamino)-phenyl]-urea

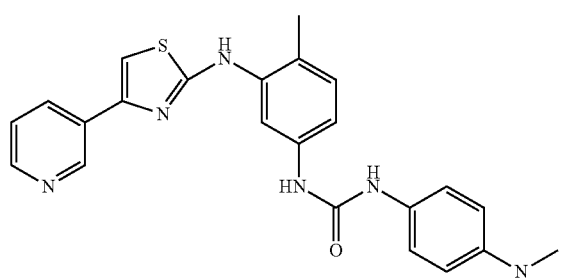

023: 1-(2-Fluoro-phenyl)-3-[4-methyl-3-(4-pyridin-3-yl-thiazol-2-ylamino)-phenyl]-urea

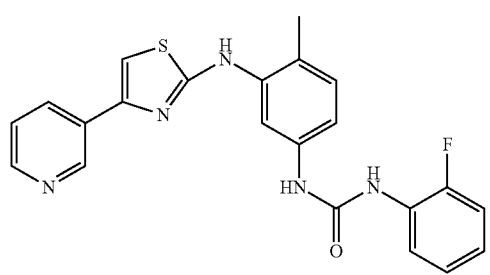

light brown powder mp: 203-206° C.
$^1$H NMR (DMSO-d$^6$): δ=☐2.24 (s, 3H); 6.98-7.00 (m, 2H); 7.10-7.23 (m, 3H); 7.40 (m, 1H); 7.48 (s, 1H); 8.25 (m, 1H); 8.37 (d, J=7.8 Hz, 1H); 8.51 (m, 3H); 9.03 (s, 1H); 9.19 (s, 1H); 9.39 (s, 1H)

024: 1-(2-Chloro-phenyl)-3-[4-methyl-3-(4-pyridin-3-yl-thiazol-2-ylamino)-phenyl]-urea

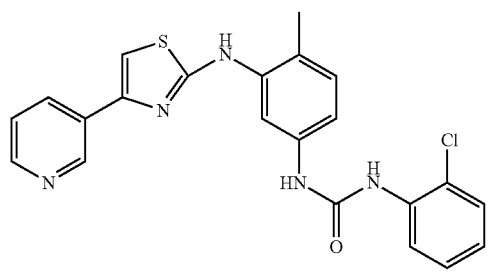 [SMILES: Cc1ccc(NC(=O)Nc2ccccc2Cl)cc1Nc1nc(-c2cccnc2)cs1]

025: 1-(3-Fluoro-phenyl)-3-[4-methyl-3-(4-pyridin-3-yl-thiazol-2-ylamino)-phenyl]-urea

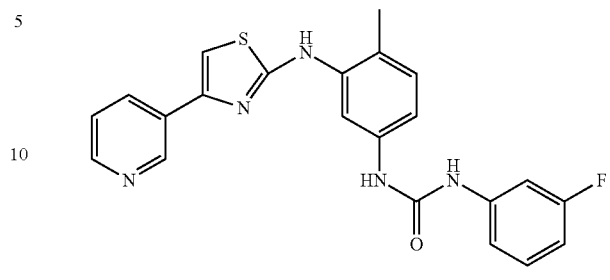

white powder mp: 210-215° C.
$^1$H NMR (DMSO-d$^6$): δ=2.24 (s, 3H); 6.79 (t, J=6.3 Hz, 1H); 6.99 (m, 1H); 7.09-7.14 (m, 2H); 7.30 (m, 1H); 7.41 (t, J=4.7 Hz, 1H); 7.48 (s, 1H); 7.56 (d, J=1.2 Hz, 1H); 8.39 (d, J=8.0 Hz, 1H); 8.49-8.52 (m, 2H); 8.71 (s, 1H); 8.87 (s, 1H); 9.18 (s, 1H); 9.38 (s, 1H)

026: 1-[4-Methyl-3-(4-pyridin-3-yl-thiazol-2-ylamino)-phenyl]-3-p-tolyl-urea

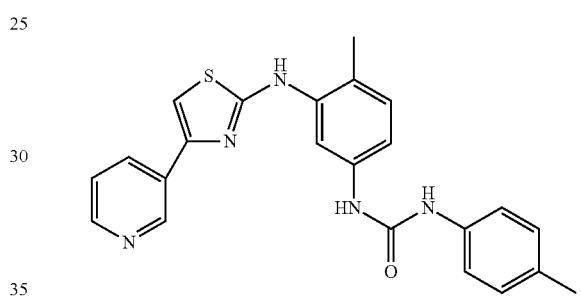

white powder mp: 238-240° C.
$^1$H RMN (DMSO-d$^6$) δ☐=2.29 (s, 3H); 2.31 (s, 3H); 7.05 (d, J=6.2 Hz, 1H); 7.10-1.16 (m, 3H); 7.42-7.49 (m, 3H); 7.53 (s, 1H); 8.35-8.62 (m, 5H); 9.22 (d, J=1.6 Hz, 1H); 9.43 (s, 1H)

Among the compounds of formula II, the invention is particularly embodied by the compounds wherein X is a-substituted Aryl group, corresponding to the N-[3-(Thiazol-2-ylamino)-phenyl]-amide family and the following formula II-3:

FORMULA II-3

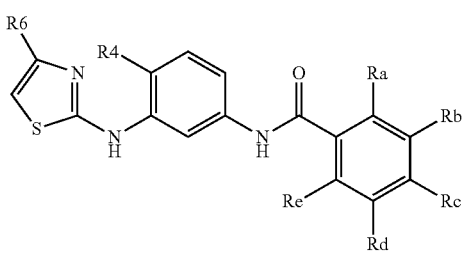

wherein Ra, Rb, Rc, Rd, Re are independently chosen from H or an organic group that can be selected for example from a linear or branched alkyl group containing from 1 to 10 carbon atoms optionally substituted with at least one heteroatom and/or bearing a pendant basic nitrogen functionality; a cycloalkyl, an aryl or heteroaryl group optionally substituted with a heteroatom, notably a halogen selected from I, Cl, Br and F or bearing a pendant basic nitrogen functionality; or a cycloalkyl, an aryl or heteroaryl group optionally substituted with a cycloalkyl, an aryl or heteroaryl group optionally substituted with an heteroatom, notably a halogen selected from I, Cl, Br and F or bearing a pendant basic nitrogen functionality;

a —SO2-R group wherein R is an alkyl, cycloalkyl, aryl or heteroaryl optionally substituted with a heteroatom, notably a halogen selected from I, Cl, Br and F or bearing a pendant basic nitrogen functionality; or a —CO—R or a —CO—NRR' group, wherein R and R' are independently chosen from H, an alkyl, a cycloalkyl, an aryl or heteroaryl group optionally substituted with at least one heteroatom, notably selected from I, Cl, Br and F, and or bearing a pendant basic nitrogen functionality;

Ra, Rb, Rc, Rd, Re may also be
- a halogen such as I, Cl, Br and F
- a NRR' group where R and R' are H or a linear or branched alkyl group containing from 1 to 10 carbon atoms optionally substituted with at least one heteroatom and/or bearing a pendant basic nitrogen functionality; a cycloalkyl, an aryl or heteroaryl group optionally substituted with a heteroatom, notably a halogen selected from I, Cl, Br and F or bearing a pendant basic nitrogen functionality; or a cycloalkyl, an aryl or heteroaryl group optionally substituted with a cycloalkyl, an aryl or heteroaryl group optionally substituted with an heteroatom, notably a halogen selected from I, Cl, Br and F or bearing a pendant basic nitrogen functionality;
- an OR group where R is H or a linear or branched alkyl group containing from 1 to 10 carbon atoms optionally substituted with at least one heteroatom and/or bearing a pendant basic nitrogen functionality; a cycloalkyl, an aryl or heteroaryl group optionally substituted with a heteroatom, notably a halogen selected from I, Cl, Br and F or bearing a pendant basic nitrogen functionality; or a cycloalkyl, an aryl or heteroaryl group optionally substituted with a cycloalkyl, an aryl or heteroaryl group optionally substituted with an heteroatom, notably a halogen selected from I, Cl, Br and F or bearing a pendant basic nitrogen functionality; a —SO2-R' group wherein R' is an alkyl, cycloalkyl, aryl or heteroaryl optionally substituted with a heteroatom, notably a halogen selected from I, Cl, Br and F or bearing a pendant basic nitrogen functionality;
- a NRaCORb group where Ra and Rb are H or a linear or branched alkyl group containing from 1 to 10 carbon atoms optionally substituted with at least one heteroatom and/or bearing a pendant basic nitrogen functionality; a cycloalkyl, an aryl or heteroaryl group optionally substituted with a heteroatom, notably a halogen selected from I, Cl, Br and F or bearing a pendant basic nitrogen functionality; or a cycloalkyl, an aryl or heteroaryl group optionally substituted with a cycloalkyl, an aryl or heteroaryl group optionally substituted with an heteroatom, notably a halogen selected from I, Cl, Br and F or bearing a pendant basic nitrogen functionality;
- a NRaCONRbRc group where Ra and Rb are H or a linear or branched alkyl group containing from 1 to 10 carbon atoms optionally substituted with at least one heteroatom and/or bearing a pendant basic nitrogen functionality; a cycloalkyl, an aryl or heteroaryl group optionally substituted with a heteroatom, notably a halogen selected from I, Cl, Br and F or bearing a pendant basic nitrogen functionality; or a cycloalkyl, an aryl or heteroaryl group optionally substituted with a cycloalkyl, an aryl or heteroaryl group optionally substituted with an heteroatom, notably a halogen selected from I, Cl, Br and F or bearing a pendant basic nitrogen functionality;
- a COOR, where R is a linear or branched alkyl group containing from 1 to 10 carbon atoms atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;
- a CONRaRb, where Ra and Rb are a hydrogen or a linear or branched alkyl group containing from 1 to 10 carbon atoms atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;
- an NHCOOR, where R is a linear or branched alkyl group containing from 1 to 10 carbon atoms atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;
- an $OSO_2R$, where R is a linear or branched alkyl group containing from 1 to 10 carbon atoms atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;
- an $NRaOSO_2Rb$, where Ra and Rb are a linear or branched alkyl group containing from 1 to 10 carbon atoms atoms optionally substituted with at least one heteroatom (for example a halogen) and/or bearing a pendant basic nitrogen functionality; Ra can also be a hydrogen; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

a CN group a trifluoromethyl group

R⁴ is hydrogen, halogen or a linear or branched alkyl group containing from 1 to 10 carbon atoms, trifluoromethyl or alkoxy;

R⁶ is one of the following:

(i) an aryl group such as phenyl or a substituted variant thereof bearing any combination, at any one ring position, of one or more substituents such as halogen, alkyl groups containing from 1 to 10 carbon atoms, trifluoromethyl, and alkoxy;

(ii) a heteroaryl group such as a 2, 3, or 4-pyridyl group, which may additionally bear any combination of one or more substituents such as halogen, alkyl groups containing from 1 to 10 carbon atoms, trifluoromethyl and alkoxy;

(iii) a five-membered ring aromatic heterocyclic group such as for example 2-thienyl, 3-thienyl, 2-thiazolyl, 4-thiazolyl, 5-thiazolyl, which may additionally bear any combination of one or more substituents such as halogen, an alkyl group containing from 1 to 10 carbon atoms, trifluoromethyl, and alkoxy;

iv) H, a halogen selected from I, F, Cl or Br; NH2, NO2 or SO2-R, wherein R is a linear or branched alkyl group containing one or more group such as 1 to 10 carbon atoms, and optionally substituted with at least one heteroatom, notably a halogen selected from I, Cl, Br and F, and/or bearing a pendant basic nitrogen functionality.

EXAMPLES

028:   3-Bromo-N-[4-methyl-3-(4-pyridin-3-yl-thiazol-2-ylamino)-phenyl]-benzamide

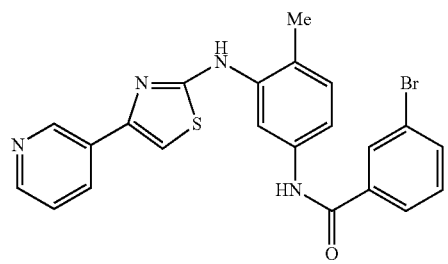 [SMILES: Cc1ccc(NC(=O)c2cccc(Br)c2)cc1Nc1nc(-c2cccnc2)cs1]

029:   3-Iodo-N-[4-methyl-3-(4-pyridin-3-yl-thiazol-2-ylamino)-phenyl]-benzamide

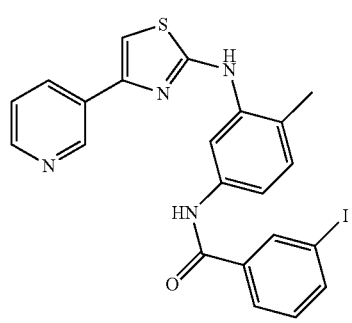 [SMILES: Cc1ccc(NC(=O)c2cccc(I)c2)cc1Nc1nc(-c2cccnc2)cs1]

030: 4-Hydroxymethyl-N-[4-methyl-3-(4-pyridin-3-yl-thiazol-2-ylamino)-phenyl]-benzamide

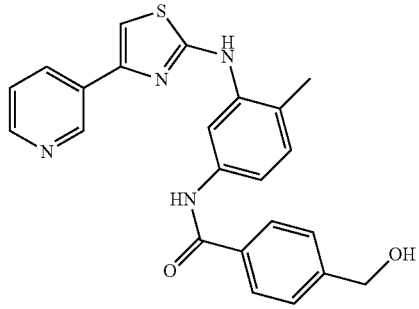 [SMILES: Cc1ccc(NC(=O)c2ccc(CO)cc2)cc1Nc1nc(-c2cccnc2)cs1]

031:   4-Amino-N-[4-methyl-3-(4-pyridin-3-yl-thiazol-2-ylamino)-phenyl]-benzamide

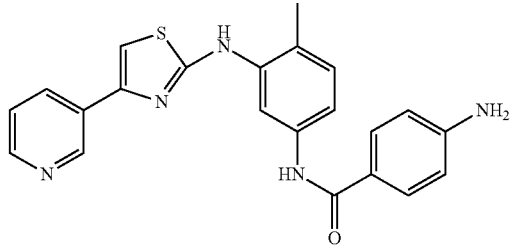 [SMILES: Cc1ccc(NC(=O)c2ccc(N)cc2)cc1Nc1nc(-c2cccnc2)cs1]

032:   2-Iodo-N-[4-methyl-3-(4-pyridin-3-yl-thiazol-2-ylamino)-phenyl]-benzamide

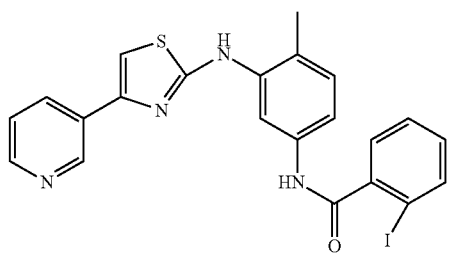 [SMILES: Cc1ccc(NC(=O)c2ccccc2I)cc1Nc1nc(-c2cccnc2)cs1]

033:   4-Iodo-N-[4-methyl-3-(4-pyridin-3-yl-thiazol-2-ylamino)-phenyl]-benzamide

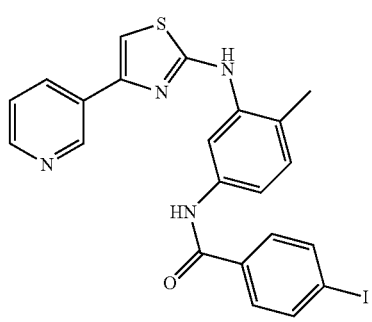 [SMILES: Cc1ccc(NC(=O)c2ccc(I)cc2)cc1Nc1nc(-c2cccnc2)cs1]

034: 4-(3-{4-[4-Methyl-3-(4-pyridin-3-yl-thiazol-2-ylamino)-phenylcarbamoyl]-phenyl}-ureido)-benzoic acid ethyl ester

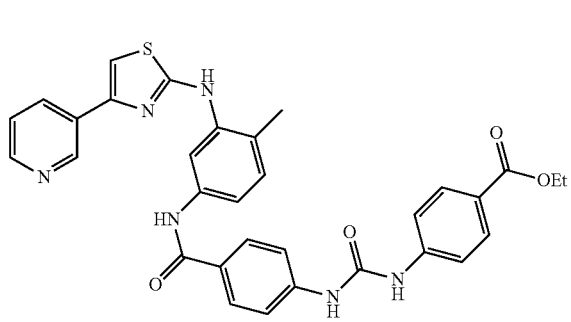 [SMILES: CCOC(=O)c1ccc(NC(=O)Nc2ccc(C(=O)Nc3ccc(C)c(Nc4nc(-c5cccnc5)cs4)c3)cc2)cc1]

035: N-[4-Methyl-3-(4-pyridin-3-yl-thiazol-2-ylamino)-phenyl]-4-[3-(4-trifluoromethyl-phenyl)-ureido]-benzamide

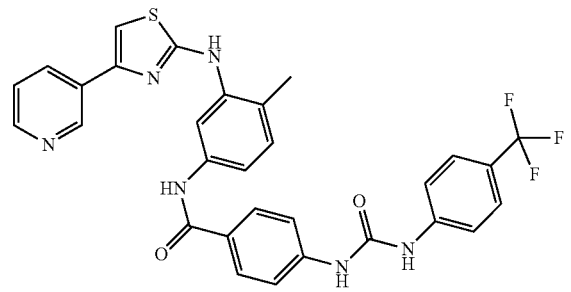 [SMILES: Cc1ccc(NC(=O)c2ccc(NC(=O)Nc3ccc(C(F)(F)F)cc3)cc2)cc1Nc1nc(-c2cccnc2)cs1]

036: 4-[3-(4-Bromo-phenyl)-ureido]-N-[4-methyl-3-(4-pyridin-3-yl-thiazol-2-ylamino)-phenyl]-benzamide

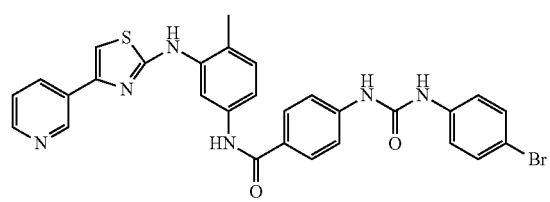 [SMILES: Cc1ccc(NC(=O)c2ccc(NC(=O)Nc3ccc(Br)cc3)cc2)cc1Nc1nc(-c2cccnc2)cs1]

037: 4-Hydroxy-N-[4-methyl-3-(4-pyridin-3-yl-thiazol-2-ylamino)-phenyl]-benzamide

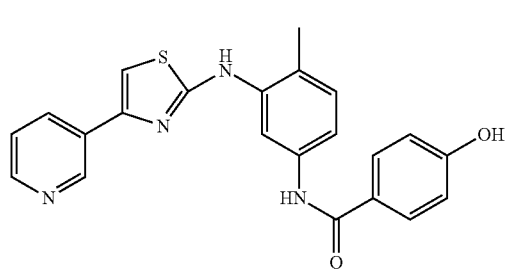 [SMILES: Cc1ccc(NC(=O)c2ccc(O)cc2)cc1Nc1nc(-c2cccnc2)cs1]

038: N-[4-Methyl-3-(4-pyridin-3-yl-thiazol-2-ylamino)-phenyl]-4-(3-thiophen-2-yl-ureido)-benzamide

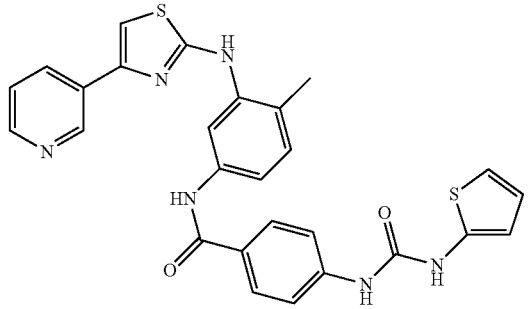 [SMILES: Cc1ccc(NC(=O)c2ccc(NC(=O)Nc3cccs3)cc2)cc1Nc1nc(-c2cccnc2)cs1]

039: 4-[3-(3,5-Dimethyl-isoxazol-4-yl)-ureido]-N-[4-methyl-3-(4-pyridin-3-yl-thiazol-2-ylamino)-phenyl]-benzamide

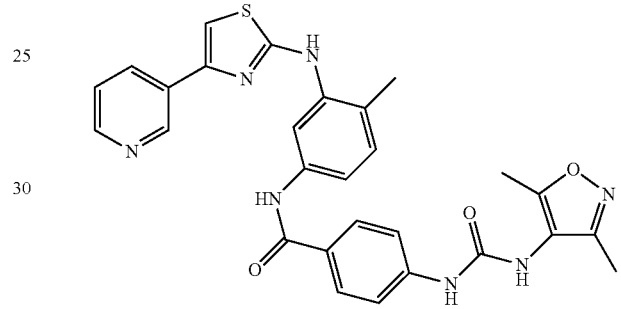

040: 4-[3-(4-Methoxy-phenyl)-ureido]-N-[4-methyl-3-(4-pyridin-3-yl-thiazol-2-ylamino)-phenyl]-benzamide

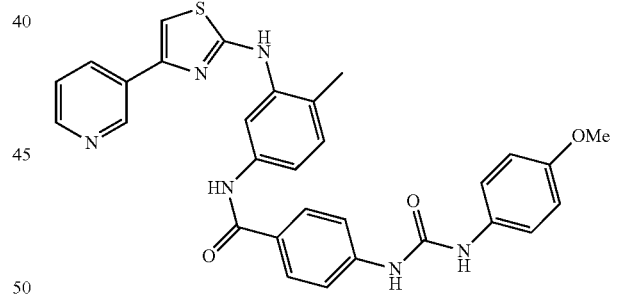

041: 4-[3-(4-Difluoromethoxy-phenyl)-ureido]-N-[4-methyl-3-(4-pyridin-3-yl-thiazol-2-ylamino)-phenyl]-benzamide

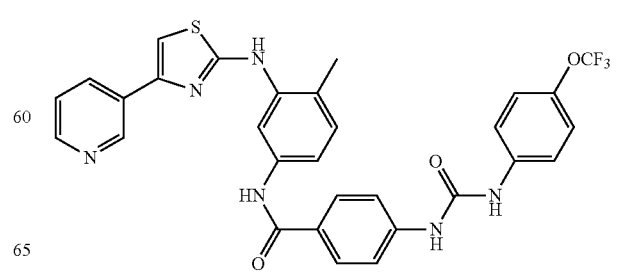

042: Thiophene-2-sulfonic acid 4-[4-methyl-3-(4-pyridin-3-yl-thiazol-2-ylamino)-phenylcarbamoyl]-phenyl ester

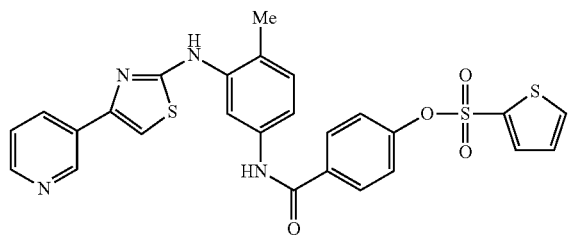 [SMILES: Cc1ccc(NC(=O)c2ccc(OS(=O)(=O)c3cccs3)cc2)cc1Nc1nc(-c2cccnc2)cs1]

043: 4-Iodo-benzenesulfonic acid 4-[4-methyl-3-(4-pyridin-3-yl-thiazol-2-ylamino)-phenylcarbamoyl]-phenyl ester

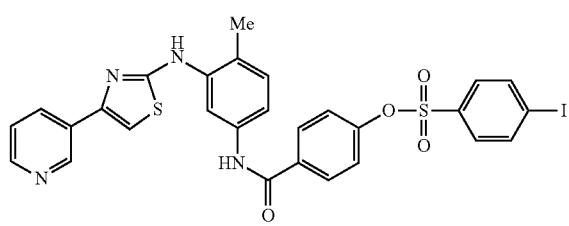 [SMILES: Cc1ccc(NC(=O)c2ccc(OS(=O)(=O)c3ccc(I)cc3)cc2)cc1Nc1nc(-c2cccnc2)cs1]

044: N-[4-Methyl-3-(4-pyridin-3-yl-thiazol-2-ylamino)-phenyl]-4-(thiophene-2-sulfonylamino)-benzamide

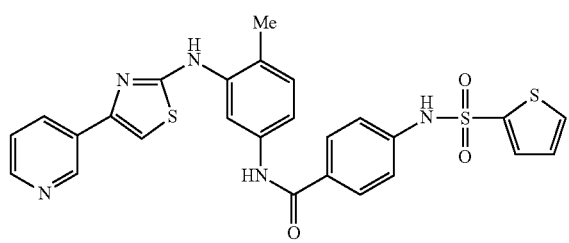 [SMILES: Cc1ccc(NC(=O)c2ccc(NS(=O)(=O)c3cccs3)cc2)cc1Nc1nc(-c2cccnc2)cs1]

brown powder mp: 230-233° C.
$^1$H NMR (DMSO-d$^6$) δ=2.29 (s, 3H); 7.15-7.18 (m, 2H); 7.22-7.32 (m, 3H); 7.48 (m, 2H); 7.67 (dd, J=1.3 Hz, J=3.7 Hz, 1H); 7.90-7.96 (m, 3H); 8.38-8.42 (m, 1H); 8.51 (m, 1H); 8.57 (d, J=1.9 Hz, 1H); 9.17 (d, J=1.7 Hz, 1H); 9.44 (s, 1H); 10.12 (s, 1H); 10.82 (s, 1H)

045: 3-Fluoro-N-[4-methyl-3-(4-pyridin-3-yl-thiazol-2-ylamino)-phenyl]-benzamide

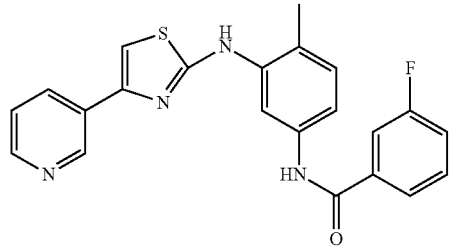 [SMILES: Cc1ccc(NC(=O)c2cccc(F)c2)cc1Nc1nc(-c2cccnc2)cs1]

off-white foam mp: 184-186° C.
$^1$H NMR (CD$_3$OD-d$^4$): δ=□□2.23 (s, 3H); 7.12-7.14 (m, 2H); 7.20-7.23 (m, 2H); 7.30 (m, 1H); 7.43 (m, 1H); 7.50 (m, 1H); 7.66 (d, J=1.0 Hz, 1H); 8.23 (m, 1H); 8.33 (m, 1H); 8.38 (s, 1H); 8.98 (s, 1H)

046: N-[4-Methyl-3-(4-pyridin-3-yl-thiazol-2-ylamino)-phenyl]-4-pyridin-4-yl-benzamide

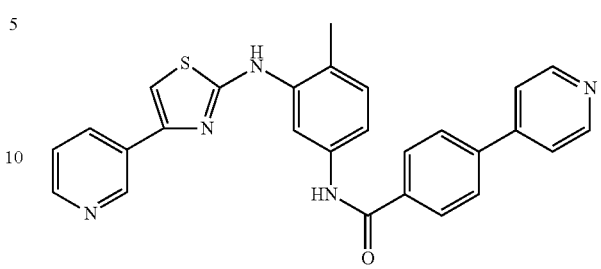

yellow powder mp: 254-256° C.
$^1$H NMR (DMSO-d$^6$): δ 2.34 (s, 3H); 7.28 (d, J=8.0 Hz, 1H); 7.45-7.49 (m, 2H); 7.54 (s, 1H); 7.78 (t, J=7.6 Hz, 1H); 7.89-7.91 (m, 2H); 8.10 (t, J=7.8 Hz, 2H); 8.37-8.42 (m, 2H); 8.55 (d, J=4.7 Hz, 1H); 8.73-8.77 (m, 3H); 9.24 (s, 1H); 9.52 (s, 1H); 10.43 (s, 1H)

047: 4-Dimethylamino-N-[4-methyl-3-(4-pyridin-3-yl-thiazol-2-ylamino)-phenyl]-benzamide

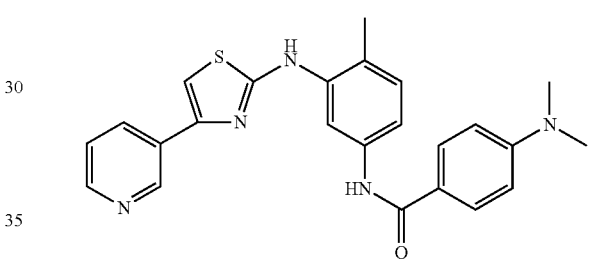

beige powder mp: 147-150° C.
$^1$H NMR (DMSO-d$^6$): δ 2.25 (s, 3H); 2.99 (s, 6H); 6.76 (d, J=8.9 Hz, 2H); 7.16 (d, J=8.3 Hz, 1H); 7.35 (d, J=2.0 Hz, 1H); 7.44-7.47 (m, 2H); 7.86-7.89 (m, 2H); 8.34-8.36 (m, 1H); 8.48-8.50 (m, 1H); 8.56-8.57 (m, 1H); 9.16 (s, 1H); 9.44 (s, 1H); 9.85 (s, 1H)

048: 2-Fluoro-5-methyl-N-[4-methyl-3-(4-pyridin-3-yl-thiazol-2-ylamino)-phenyl]-benzamide

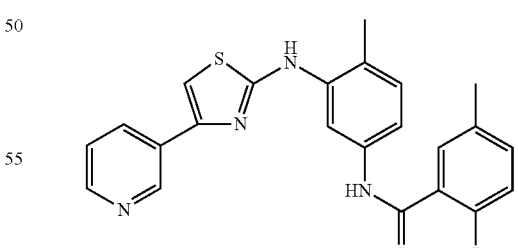

brown orange powder mp: 103-106° C.
$^1$H RMN (DMSO-d$^6$) δ=2.26 (s, 3H); 2.35 (s, 3H); 7.17-7.47 (m, 7H); 8.29 (dd, J=1.6 Hz, J=7.9 Hz, 1H); 8.47 (d, J=3.5 Hz, 1H); 8.57 (s, 1H); 9.15 (d, J=2.0 Hz, 1H); 9.44 (s, 1H); 10.33 (s, 1H)

049: 4-tert-Butyl-N-[4-methyl-3-(4-pyridin-3-yl-thiazol-2-ylamino)-phenyl]-benzamide

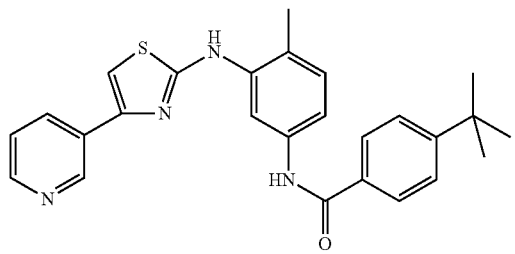 [SMILES: Cc1ccc(NC(=O)c2ccc(C(C)(C)C)cc2)cc1Nc1nc(-c2cccnc2)cs1]

brown powder mp: 145-150° C.

$^1$H RMN (DMSO-d$^6$) δ=1.32 (s, 9H); 2.04 (s, 3H); 7.18 (d, J=8.4 Hz, 1H); 7.35-7.44 (m, 2H); 7.46 (s, 1H); 7.55 (d, J=8.5 Hz, 1H); 7.90 (d, J=8.5 Hz, 1H); 8.32 (d, J=7.9 Hz, 1H); 8.47 (dd, J=1.5 Hz, J=4.7 Hz, 1H); 8.60 (d, J=2.0 Hz, 1H); 9.15 (d, J=1.7 Hz, 1H); 9.43 (s, 1H); 10.15 (s, 1H)

050: 4-Isopropoxy-N-[4-methyl-3-(4-pyridin-3-yl-thiazol-2-ylmethyl)-phenyl]-benzamide

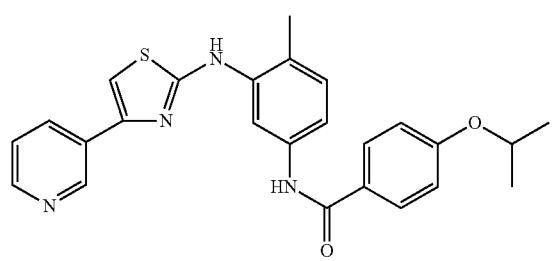 [SMILES: Cc1ccc(NC(=O)c2ccc(OC(C)C)cc2)cc1Nc1nc(-c2cccnc2)cs1]

brown powder mp: 154-155° C.

$^1$H RMN (DMSO-d$^6$) δ=1.34 (d, J=5.9 Hz, 6H); 4.72 (hept, J=5.9 Hz, 1H); 7.01 (d, J=7.0 Hz, 2H); 7.18 (d, J=8.5 Hz, 1H); 7.35-7.44 (m, 2H); 7.46 (s, 1H); 7.94 (dd, J=2.0 Hz, J=6.7 Hz, 2H); 8.32 (d, J=8.3 Hz, 1H); 8.48 (dd, J=3.3 Hz, J=4.8 Hz, 1H); 8.58 (d, J=2.0 Hz, 1H); 9.15 (d, J=1.8 Hz, 1H); 9.43 (s, 1H); 10.4 (s, 1H)

051: Benzo[1,3]dioxole-5-carboxylic acid [4-methyl-3-(4-pyridin-3-yl-thiazol-2-ylmethyl)-phenyl]-amide

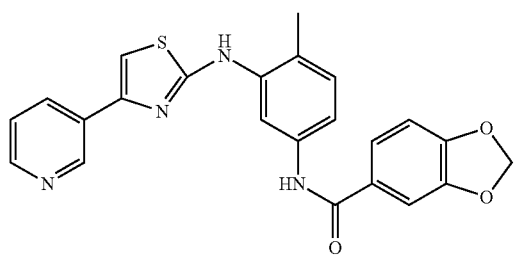 [SMILES: Cc1ccc(NC(=O)c2ccc3c(c2)OCO3)cc1Nc1nc(-c2cccnc2)cs1]

brown orange powder mp: 130432° C.

$^1$H RMN (DMSO-d$^6$) δ=2.23 (s, 3H); 6.10 (s, 2H); 7.03 (d, J=8.1 Hz, 1H); 7.15 (d, J=8.3 Hz, 1H); 7.25-7.55 (m, 6H); 8.26 (s, 1H); 8.45 (dd, J=1.5 Hz, J=4.7, 1H); 8.55 (d, J=2.0 Hz, 1H); 9.12 (d, J=1.7 Hz, 1H); 9.40 (s, 1H); 10.01 (s, 1H)

052: N-[4-Methyl-3-(4-pyridin-3-yl-thiazol-2-ylamino)-phenyl]-3-(2-morpholin-4-yl-ethoxy)-benzamide

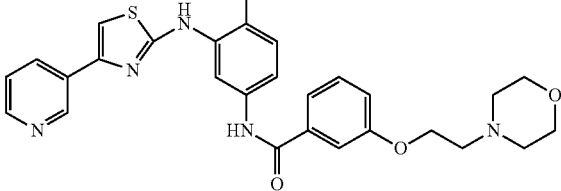

beige yellow powder mp: 75-80° C.

$^1$H RMN (DMSO-d$^6$) δ=2.10-2.25 (m, 4H); 2.50-2.60 (m, 2H); 3.19 (s, 3H); 3.41-3.48 (m, 4H); 4.00-4.06 (m, 2H); 7.00-7.11 (m, 2H); 7.22-7.35 (m, 6H); 8.18 (d, J=8.0 Hz, 1H); 8.33 (d, J=0.9 Hz, 1H); 8.49 (d, J=1.7 Hz, 1H); 9.03 (s, 1H); 9.31 (s, 1H); 10.05 (s, 1H)

053: N-[4-Methyl-3-(4-pyridin-3-yl-thiazol-2-ylmethyl)-phenyl]-4-pyridin-4-yl-benzamide

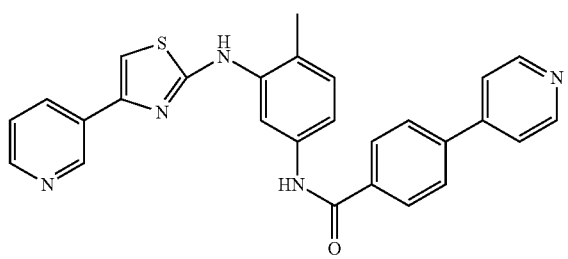 [SMILES: Cc1ccc(NC(=O)c2ccc(-c3ccncc3)cc2)cc1Nc1nc(-c2cccnc2)cs1]

brown powder mp: dec. 250° C.

$^1$H RMN (DMSO-d$^6$) δ=2.28 (s, 3H); 7.21 (d, J=7.9 Hz, 1H); 7.30-7.50 (m, 3H); 7.81 (d, J=4.7 Hz, 1H); 7.98 (d, J=7.5 Hz, 2H); 8.13 (d, J=7.9 Hz, 2H); 8.32 (d, J=7.7 Hz, 1H); 8.48 (d, J=4.9 Hz, 1H); 8.62-8.69 (m, 3H); 9.16 (s, 1H); 9.45 (s, 1H); 10.34 (s, 1H)

054: 3-Cyano-N-[4-methyl-3-(4-pyridin-3-yl-thiazol-2-ylamino)-phenyl]-benzamide

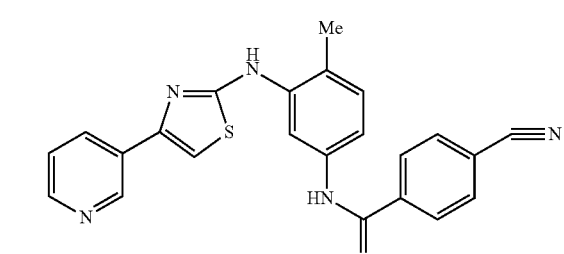

055: 2-Fluoro-N-[4-methyl-3-(4-pyridin-3-yl-thiazol-2-ylamino)-phenyl]-3-trifluoromethyl-benzamide

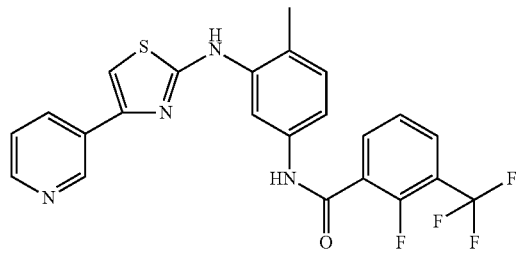 [SMILES: Cc1ccc(NC(=O)c2cccc(C(F)(F)F)c2F)cc1Nc1nc(-c2cccnc2)cs1]

056: 3-Fluoro-benzenesulfonic acid 4-[4-methyl-3-(4-pyridin-3-yl-thiazol-2-ylamino)-phenylcarbamoyl]-phenyl ester

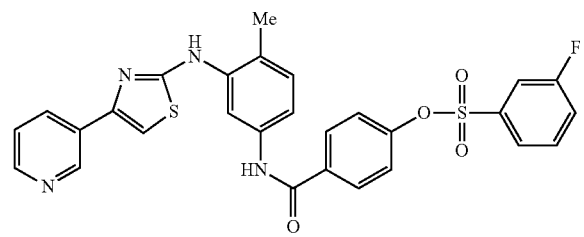 [SMILES: Cc1ccc(NC(=O)c2ccc(OS(=O)(=O)c3cccc(F)c3)cc2)cc1Nc1nc(-c2cccnc2)cs1]

057: 4-Aminomethyl-N-[4-methyl-3-(4-pyridin-3-yl-thiazol-2-ylamino)-phenyl]-benzamide

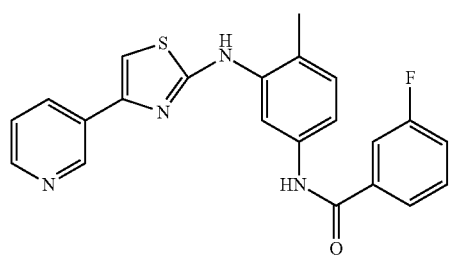 [SMILES: Cc1ccc(NC(=O)c2cccc(F)c2)cc1Nc1nc(-c2cccnc2)cs1]

058: 2-Fluoro-benzenesulfonic acid 4-[4-methyl-3-(4-pyridin-3-yl-thiazol-2-ylamino)-phenylcarbamoyl]-phenyl ester

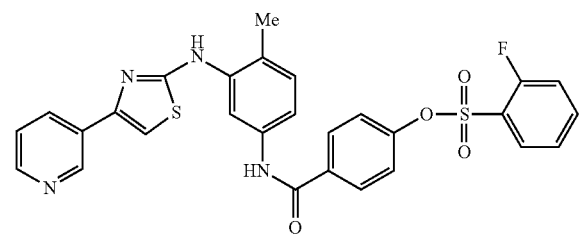 [SMILES: Cc1ccc(NC(=O)c2ccc(OS(=O)(=O)c3ccccc3F)cc2)cc1Nc1nc(-c2cccnc2)cs1]

059: -Methoxy-N-[4-methyl-3-(4-pyridin-3-yl-thiazol-2-ylmethyl)-phenyl]-benzamide

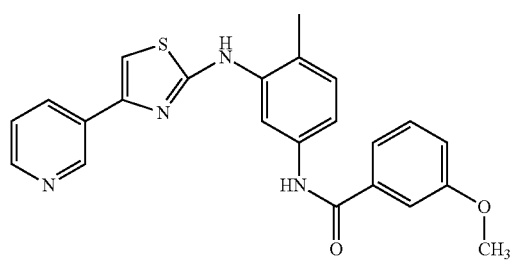 [SMILES: COc1cccc(C(=O)Nc2ccc(C)c(Nc3nc(-c4cccnc4)cs3)c2)c1]

white powder mp: 76-79° C.
$^1$H RMN (DMSO-d$^6$) δ=2.32 (s, 3H); 3.89 (s, 3H); 7.22-7.25 (m, 2H), 7.44-7.58 (m, 4H); 8.28-8.35 (m, 1H); 8.52 (dd, J=1.6 Hz, J=4.7 Hz, 1H); 8.66 (d, J=2.0 Hz, 1H); 9.20 (d, J=1.4 Hz, 1H); 9.50 (s, 1H); 10.25 (s, 1H)

060: 4-(4-Methyl-piperazin-1-yl)-N-[4-methyl-3-(4-pyridin-3-yl-thiazol-2-ylmethyl)-phenyl]-benzamide

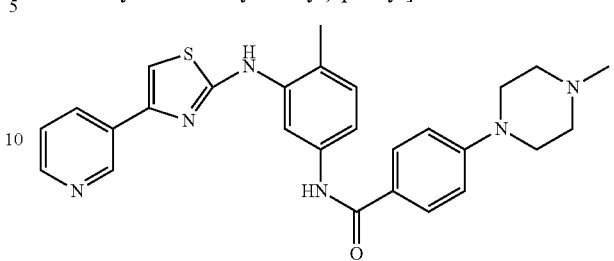

beige brown powder mp: 128-130° C.
$^1$H RMN (DMSO-d$^6$) δ=2.15 (s, 3H); 2.18 (s, 3H); 2.35-2.41 (m, 4H); 3.18-3.3.24 (m, 4H); 6.94 (d, J=8.9 Hz, 2H); 7.09 (d, J=8.4 Hz, 1H); 7.28-7.38 (m, 3H); 7.81 (d, J=8.9 Hz, 2H); 8.20-8.25 (m, 1H); 8.40 (dd, J=1.6 Hz, J=4.7, 1H); 8.48 (d, J=1.9 Hz, 1H); 9.07 (d, J=1.5 Hz, 1H); 9.35 (s, 1H); 9.84 (s, 1H)

061: 3-Methyl-N-[4-methyl-3-(4-pyridin-3-yl-thiazol-2-ylamino)-phenyl]-benzamide

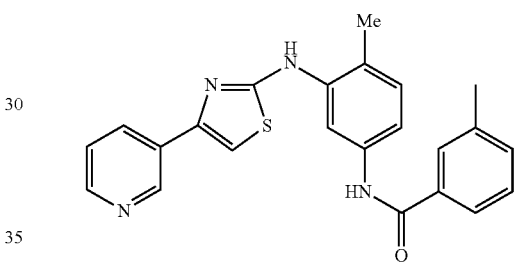

062: Biphenyl-3-carboxylic acid [4-methyl-3-(4-pyridin-3-yl-thiazol-2-ylamino phenyl]-amide

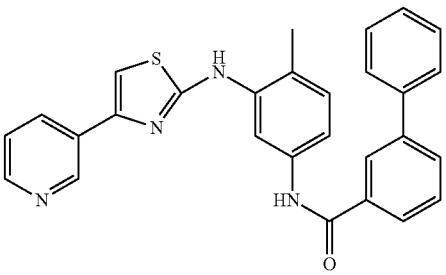 [SMILES: Cc1ccc(NC(=O)c2cccc(-c3ccccc3)c2)cc1Nc1nc(-c2cccnc2)cs1]

065: N-[4-Methyl-3-(4-pyridin-3-yl-thiazol-2-ylamino)-phenyl]-3-trifluoromethyl-benzamide

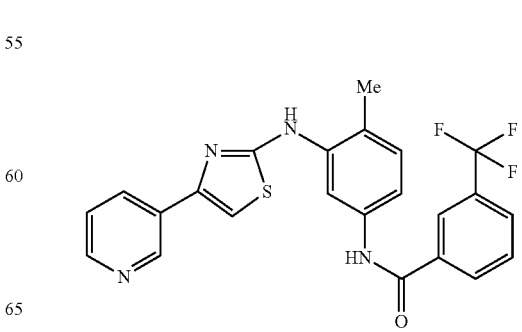

099: N-[4-Methyl-3-(4-pyridin-3-yl-thiazol-2-ylamino)-phenyl]-4-pyrrolidin-1-ylmethyl-benzamide

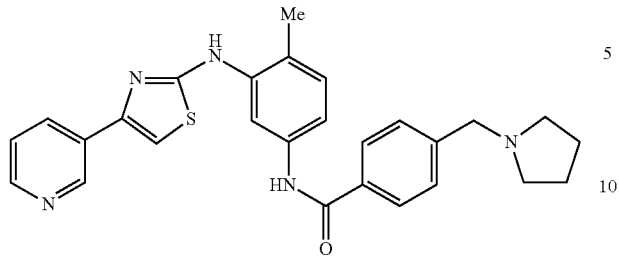

100: 4-[3-(2,4-Dimethoxy-phenyl)-ureido]-N-[4-methyl-3-(4-pyridin-3-yl-thiazol-2-ylamino)-phenyl]-benzamide

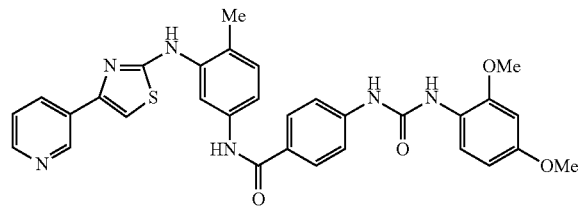 [SMILES: COc1ccc(NC(=O)Nc2ccc(C(=O)Nc3ccc(C)c(Nc4nc(-c5cccnc5)cs4)c3)cc2)c(OC)c1]

101: 4-[3-(2-Iodo-phenyl)-ureido]-N-[4-methyl-3-(4-pyridin-3-yl-thiazol-2-ylamino)-phenyl]-benzamide

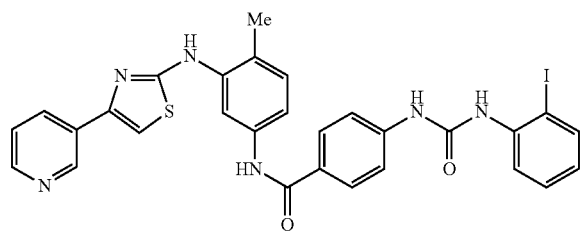 [SMILES: Cc1ccc(NC(=O)c2ccc(NC(=O)Nc3ccccc3I)cc2)cc1Nc1nc(-c2cccnc2)cs1]

102: 4-[3-(4-Fluoro-phenyl)-ureido]-N-[4-methyl-3-(4-pyridin-3-yl-thiazol-2-ylamino)-phenyl]-benzamide

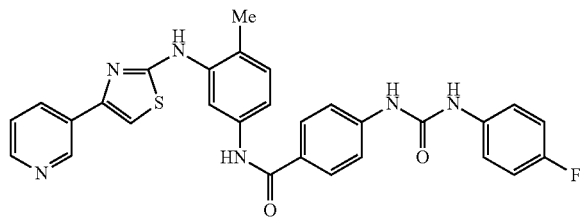 [SMILES: Cc1ccc(NC(=O)c2ccc(NC(=O)Nc3ccc(F)cc3)cc2)cc1Nc1nc(-c2cccnc2)cs1]

105: 3-Bromo-4-methyl-N-[4-methyl-3-(4-pyridin-3-yl-thiazol-2-ylamino)-phenyl]-benzamide 106: 4-Fluoro-N-[4-methyl-3-(4-pyridin-3-yl-thiazol-2-ylamino)-phenyl]-benzamide

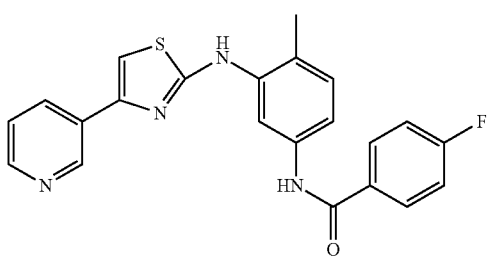 [SMILES: Cc1ccc(NC(=O)c2ccc(F)cc2)cc1Nc1nc(-c2cccnc2)cs1]

103: 4-Cyano-N-[4-methyl-3-(4-pyridin-3-yl-thiazol-2-ylamino)-phenyl]-benzamide

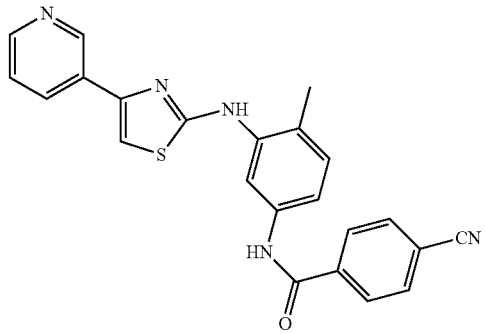 [SMILES: Cc1ccc(NC(=O)c2ccc(C#N)cc2)cc1Nc1nc(-c2cccnc2)cs1]

104: 4-Fluoro-N-[4-methyl-3-(4-pyridin-3-yl-thiazol-2-ylamino)-phenyl]-benzamide

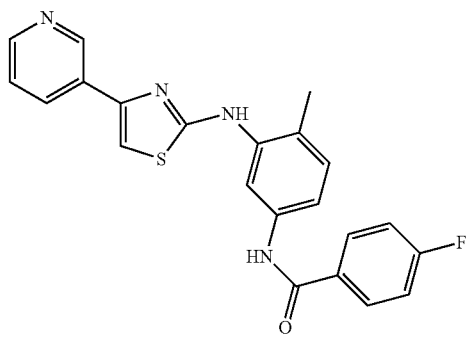 [SMILES: Cc1ccc(NC(=O)c2ccc(F)cc2)cc1Nc1nc(-c2cccnc2)cs1]

Among compounds of formula II, the invention is particularly embodied by the compounds wherein X is a -substituted-aryl group, corresponding to the 4-(4-substituted-1-yl-methyl)-N-[3-(thiazol-2-ylamino)-phenyl]-benzamide family and the following formula II-4:

FORMULA II-4

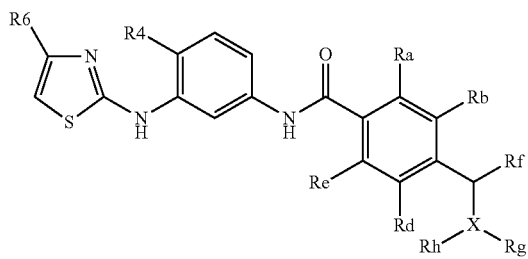

wherein X is a heteroatom, such as O or N
wherein Ra, Rb, Rd, Re, Rf, Rg, Rh are independently chosen from H or an organic group that can be selected for example from a linear or branched alkyl group containing from 1 to 10 carbon atoms optionally substituted with at least one heteroatom and/or bearing a pendant basic nitrogen functionality; a cycloalkyl, an aryl or heteroaryl group optionally substituted with a heteroatom, notably a halogen selected from I, Cl, Br and F or bearing a pendant basic nitrogen functionality; or a cycloalkyl, an aryl or heteroaryl group optionally substituted with a cycloalkyl, an aryl or heteroaryl group optionally substituted with an heteroatom, notably a halogen selected from I, Cl, Br and F or bearing a pendant basic nitrogen functionality;
or a NRR' group where R and R' are H or a linear or branched alkyl group containing from 1 to 10 carbon atoms optionally substituted with at least one heteroatom and/or bearing a pendant basic nitrogen functionality; a cycloalkyl, an aryl or heteroaryl group optionally substituted with a heteroatom, notably a halogen selected from I, Cl, Br and F or bearing a pendant basic nitrogen functionality; or a cycloalkyl, an aryl or heteroaryl group optionally substituted with a cycloalkyl, an aryl or heteroaryl group optionally substituted with an heteroatom, notably a halogen selected from I, Cl, Br and F or bearing a pendant basic nitrogen functionality;

or an OR group where R is H or a linear or branched alkyl group containing from 1 to 10 carbon atoms optionally substituted with at least one heteroatom and/or bearing a pendant basic nitrogen functionality; a cycloalkyl, an aryl or heteroaryl group optionally substituted with a heteroatom, notably a halogen selected from I, Cl, Br and F or bearing a pendant basic nitrogen functionality; or a cycloalkyl, an aryl or heteroaryl group optionally substituted with a cycloalkyl, an aryl or heteroaryl group optionally substituted with an heteroatom, notably a halogen selected from I, Cl, Br and F or bearing a pendant basic nitrogen functionality; a —SO2-R' group wherein R' is an alkyl, cycloalkyl, aryl or heteroaryl optionally substituted with a heteroatom, notably a halogen selected from I, Cl, Br and F or bearing a pendant basic nitrogen functionality;

or a NRaCORb group where Ra and Rb are H or a linear or branched alkyl group containing from 1 to 10 carbon atoms optionally substituted with at least one heteroatom and/or bearing a pendant basic nitrogen functionality; a cycloalkyl, an aryl or heteroaryl group optionally substituted with a heteroatom, notably a halogen selected from I, Cl, Br and F or bearing a pendant basic nitrogen functionality; or a cycloalkyl, an aryl or heteroaryl group optionally substituted with a cycloalkyl, an aryl or heteroaryl group optionally substituted with an heteroatom, notably a halogen selected from I, Cl, Br and F or bearing a pendant basic nitrogen functionality;

or a NRaCONRbRc group where Ra and Rb are H or a linear or branched alkyl group containing from 1 to 10 carbon atoms optionally substituted with at least one heteroatom and/or bearing a pendant basic nitrogen functionality; a cycloalkyl, an aryl or heteroaryl group optionally substituted with a heteroatom, notably a halogen selected from I, Cl, Br and F or bearing a pendant basic nitrogen functionality; or a cycloalkyl, an aryl or heteroaryl group optionally substituted with a cycloalkyl, an aryl or heteroaryl group optionally substituted with an heteroatom, notably a halogen selected from I, Cl, Br and F or bearing a pendant basic nitrogen functionality;

or a COOR, where R is a linear or branched alkyl group containing from 1 to 10 carbon atoms atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

or a CONRaRb, where Ra and Rb are a hydrogen or a linear or branched alkyl group containing from 1 to 10 carbon atoms atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

or an NHCOOR, where R is a linear or branched alkyl group containing from 1 to 10 carbon atoms atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

an $OSO_2R$, where R is a linear or branched alkyl group containing from 1 to 10 carbon atoms atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

or an $NRaOSO_2Rb$, where Ra and Rb are a linear or branched alkyl group containing from 1 to 10 carbon atoms atoms optionally substituted with at least one heteroatom (for example a halogen) and/or bearing a pendant basic nitrogen functionality; Ra can also be a hydrogen; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

or a —SO2-R group wherein R is an alkyl, cycloalkyl, aryl or heteroaryl optionally substituted with an heteroatom, notably a halogen selected from I, Cl, Br and F or bearing a pendant basic nitrogen functionality; or a —CO—R or a —CO—NRR' group, wherein R and R' are independently chosen from H, an alkyl, a cycloalkyl, an aryl or heteroaryl group optionally substituted with at least one heteroatom, notably selected from I, Cl, Br and F, and/or bearing a pendant basic nitrogen functionality.

Ra, Rb, Rd, Re can also be halogen such as Cl, F, Br, I or trifluoromethyl;

$R^4$ is hydrogen, halogen or a linear or branched alkyl group containing from 1 to 10 carbon atoms, trifluoromethyl or alkoxy;

$R^6$ is one of the following:

(i) an aryl group such as phenyl or a substituted variant thereof bearing any combination, at any one ring position, of one or more substituents such as halogen, alkyl groups containing from 1 to 10 carbon atoms, trifluoromethyl, and alkoxy;

(ii) a heteroaryl group such as a 2, 3, or 4-pyridyl group, which may additionally bear any combination of one or more substituents such as halogen, alkyl groups containing from 1 to 10 carbon atoms, trifluoromethyl and alkoxy;

(iii) a five-membered ring aromatic heterocyclic group such as for example 2-thienyl, 3-thienyl, 2-thiazolyl, 4-thiazolyl, 5-thiazolyl, which may additionally bear any combination of one or more substituents such as halogen, an alkyl group containing from 1 to 10 carbon atoms, trifluoromethyl, and alkoxy;

iv) H, a halogen selected from I, F, Cl or Br; NH2, NO2 or SO2-R, wherein R is a linear or branched alkyl group containing one or more group such as 1 to 10 carbon atoms, and optionally substituted with at least one heteroatom, notably a halogen selected from I, Cl, Br and F, and/or bearing a pendant basic nitrogen functionality

EXAMPLES

066: 4-(4-methyl-piperazin-1-ylmethyl)-N-[4-methyl-3-(4-pyridin-3-yl-thiazol-2-ylamino)-phenyl]-benzamide

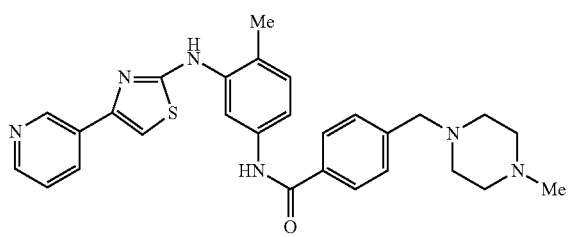 [SMILES: Cc1ccc(NC(=O)c2ccc(CN3CCN(C)CC3)cc2)cc1Nc1nc(-c2cccnc2)cs1]

067: 3,5-Dibromo-4-(4-methyl-piperazin-1-ylmethyl)-N-[4-methyl-3-(4-pyridin-3-yl-thiazol-2-ylamino)-phenyl]-benzamide

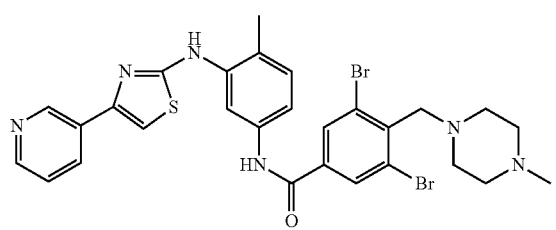 [SMILES: Cc1ccc(NC(=O)c2cc(Br)c(CN3CCN(C)CC3)c(Br)c2)cc1Nc1nc(-c2cccnc2)cs1]

068: 4-Diethylaminomethyl-N-[4-methyl-3-(4-pyridin-3-yl-thiazol-2-ylamino)-phenyl]-benzamide

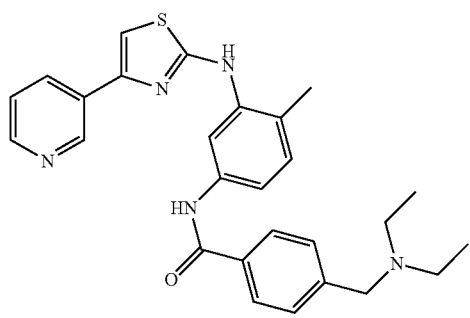 [SMILES: CCN(CC)Cc1ccc(C(=O)Nc2ccc(C)c(Nc3nc(-c4cccnc4)cs3)c2)cc1]

069: N-[4-Methyl-3-(4-pyridin-3-yl-thiazol-2-ylamino)-phenyl]-4-morpholin-4-ylmethyl-benzamide

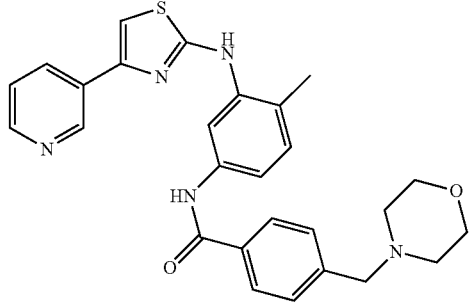 [SMILES: Cc1ccc(NC(=O)c2ccc(CN3CCOCC3)cc2)cc1Nc1nc(-c2cccnc2)cs1]

070: 4-Dipropylaminomethyl-N-[4-methyl-3-(4-pyridin-3-yl-thiazol-2-ylamino)-phenyl]-benzamide

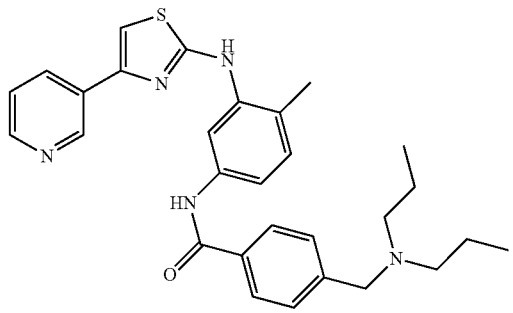 [SMILES: CCCN(CCC)Cc1ccc(C(=O)Nc2ccc(C)c(Nc3nc(-c4cccnc4)cs3)c2)cc1]

071: N-[4-Methyl-3-(4-pyridin-3-yl-thiazol-2-ylamino)-phenyl]-4-piperidin-1-ylmethyl-benzamide

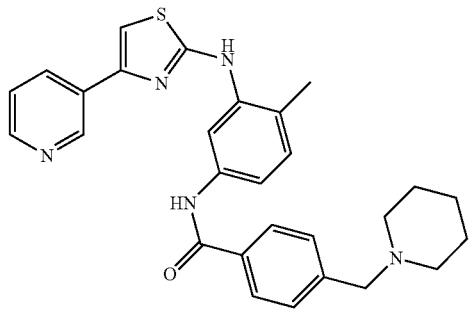 [SMILES: Cc1ccc(NC(=O)c2ccc(CN3CCCCC3)cc2)cc1Nc1nc(-c2cccnc2)cs1]

072: 4-[(Diisopropylamino)-methyl]-N-[4-methyl-3-(4-pyridin-3-yl-thiazol-2-ylamino)-phenyl]-benzamide

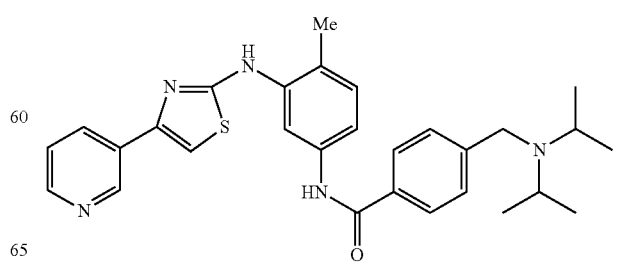

073: {4-[4-Methyl-3-(4-pyridin-3-yl-thiazol-2-ylamino)-phenylcarbamoyl]-benzyl}-carbamic acid tert-butyl ester

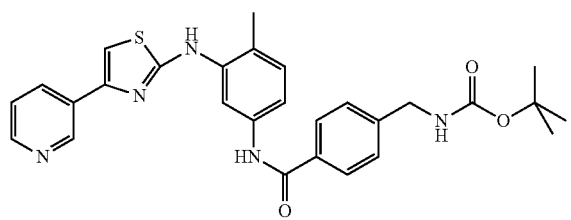 [SMILES: Cc1ccc(NC(=O)c2ccc(CNC(=O)OC(C)(C)C)cc2)cc1Nc1nc(-c2cccnc2)cs1]

074: 3-Fluoro-4-(4-methyl-piperazin-1-ylmethyl)-N-[4-methyl-3-(4-pyridin-3-yl-thiazol-2-ylamino)-phenyl]-benzamide

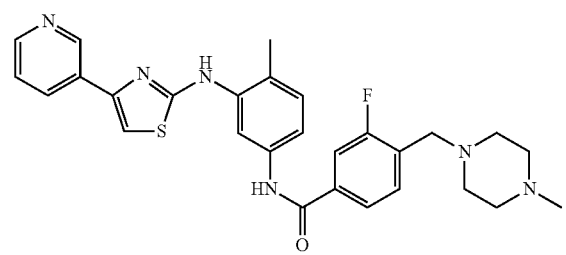 [SMILES: Cc1ccc(NC(=O)c2ccc(CN3CCN(C)CC3)c(F)c2)cc1Nc1nc(-c2cccnc2)cs1]

075: 4-(4-Methyl-piperazin-1-ylmethyl)-N-[4-methyl-3-(4-pyridin-3-yl-thiazol-2-ylmethyl)-phenyl]-3-trifluoromethyl-benzamide

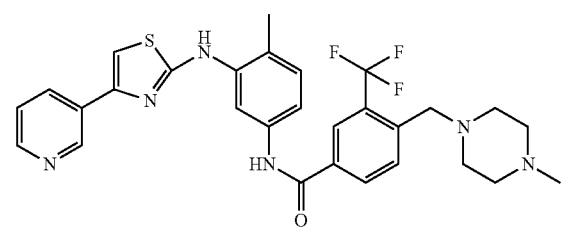 [SMILES: Cc1ccc(NC(=O)c2ccc(CN3CCN(C)CC3)c(C(F)(F)F)c2)cc1Nc1nc(-c2cccnc2)cs1]

yellow crystals mp: 118-120° C.

$^1$H RMN (DMSO-d$^6$) δ=2.22 (s, 3H); 2.33 (s, 3H); 2.34-2.50 (m, 8H); 3.74 (s, 2H); 7.26 (d, J=8.3 Hz, 1H); 7.41-7.49 (m, 2H); 7.53 (s, 1H); 7.99 (d, J=8.0 Hz, 1H); 8.28-8.31 (m, 2H); 8.38 (d, J=7.9 Hz, 1H); 8.53 (dd, J=1.3 Hz, J=4.7 Hz, 1H); 8.68 (d, J=1.9 Hz, 1H); 9.21 (d, J=2.0 Hz, 1H); 9.53 (s, 1H); 10.49 (s, 1H)

076: 2,3,5,6-Tetrafluoro-4-(4-methyl-piperazin-1-ylmethyl)-N-[4-methyl-3-(4-pyridin-3-yl-thiazol-2-ylamino)-phenyl]-benzamide

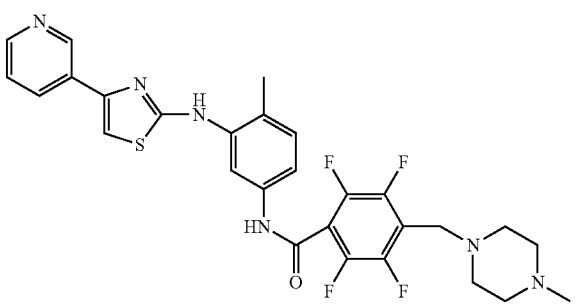 [SMILES: Cc1ccc(NC(=O)c2c(F)c(F)c(CN3CCN(C)CC3)c(F)c2F)cc1Nc1nc(-c2cccnc2)cs1]

077: N-{3-[4-(4-Fluoro-phenyl)-thiazol-2-ylamino]-4-methyl-phenyl}-4-(4-methyl-piperazin-1-ylmethyl)-benzamide

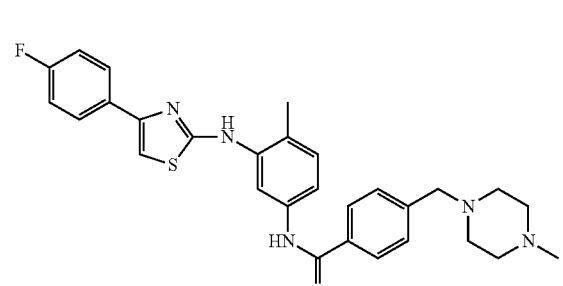

078: 3-Bromo-4-(4-methyl-piperazin-1-ylmethyl)-N-[4-methyl-3-(4-pyridin-3-yl-thiazol-2-ylamino)-phenyl]-benzamide

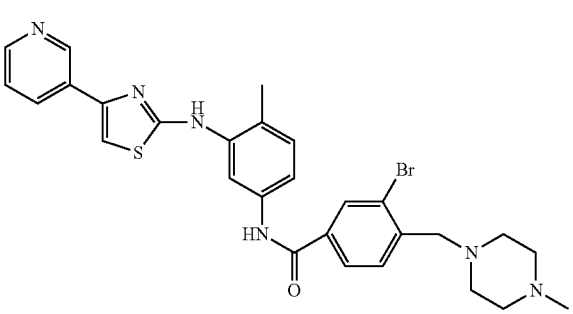 [SMILES: Cc1ccc(NC(=O)c2ccc(CN3CCN(C)CC3)c(Br)c2)cc1Nc1nc(-c2cccnc2)cs1]

079: 3-Chloro-4-(4-methyl-piperazin-1-ylmethyl)-N-[4-methyl-3-(4-pyridin-3-yl-thiazol-2-ylamino)-phenyl]-benzamide

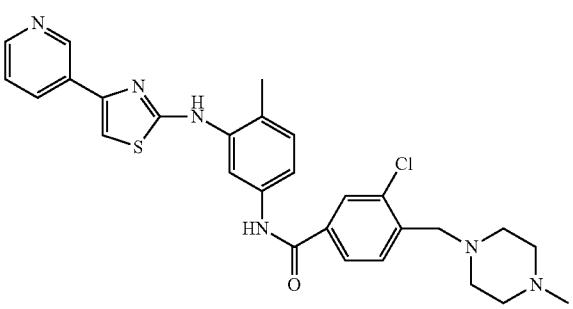 [SMILES: Cc1ccc(NC(=O)c2ccc(CN3CCN(C)CC3)c(Cl)c2)cc1Nc1nc(-c2cccnc2)cs1]

080: 4-(4-Methyl-piperazin-1-ylmethyl)-N-[4-methyl-3-(4-pyridin-4-yl-thiazol-2-ylamino)-phenyl]-benzamide

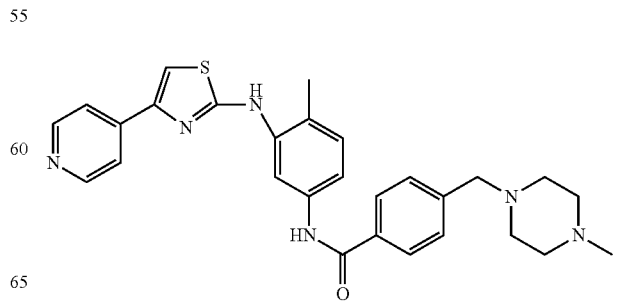

081: N-{3-[4-(4-Cyano-phenyl)-thiazol-2-ylamino]-4-methyl-phenyl}-4-(4-methyl-piperazin-1-ylmethyl)-benzamide

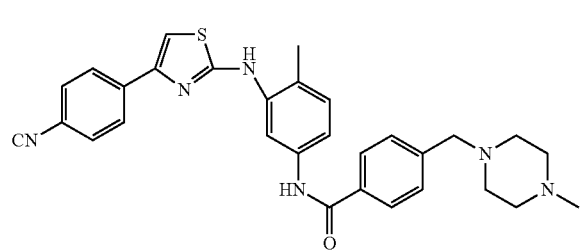

082: 4-[1-(4-Methyl-piperazin-1-yl)-ethyl]-N-[4-methyl-3-(4-pyridin-3-yl-thiazol-2-ylmethyl)-phenyl]-benzamide

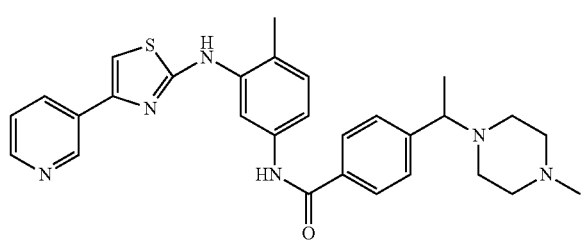 [SMILES: Cc1ccc(NC(=O)c2ccc(C(C)N3CCN(C)CC3)cc2)cc1Nc1nc(-c2cccnc2)cs1]

beige powder mp: 153-155° C.

$^1$H RMN (DMSO-d$^6$) δ=1.29 (d, J=6.6 Hz, 3H); 2.15 (s, 3H); 2.26 (s, 3H); 3.15-3.25 (m, 9H); 7.18 (d, J=8.4 Hz, 1H); 7.35-7.47 (m, 5H); 7.91 (d, J=8.2 Hz, 2H); 8.31 (d, =8.0 Hz, 1H); 8.47 (dd, J=1.6 Hz, J=4.7 Hz, 1H); 8.60 (d, J=2.0, 1H); 9.15 (d, J=0.6, 1H); 9.45 (s, 1H); 10.18 (s, 1H)

083: 4-(1-Methoxy-ethyl)-N-[4-methyl-3-(4-pyridin-3-yl-thiazol-2-ylmethyl)-phenyl]-benzamide 084: N-{4-Methyl-3-[4-(5-methyl-pyridin-3-yl)-thiazol-2-ylamino]-phenyl}-4-(4-methyl-piperazin-1-ylmethyl)-benzamide

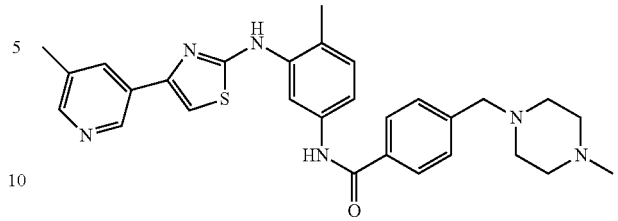

085: 3-Iodo-4-(4-methyl-piperazin-1-ylmethyl)-N-[4-methyl-3-(4-pyridin-3-yl-thiazol-2-ylmethyl)-phenyl]-benzamide

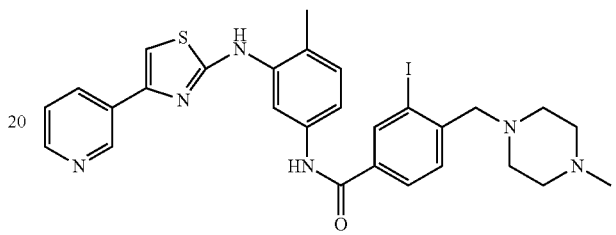

086: N-[4-Methyl-3-(4-pyridin-3-yl-thiazol-2-ylamino)-phenyl]-4-[3-(4-trifluoromethyl-phenyl)-ureidomethyl]-benzamide

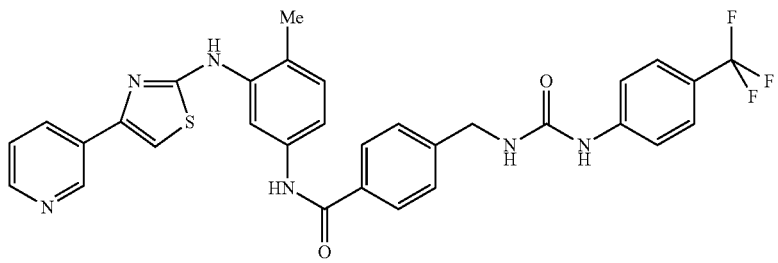 [SMILES: Cc1ccc(NC(=O)c2ccc(CNC(=O)Nc3ccc(C(F)(F)F)cc3)cc2)cc1Nc1nc(-c2cccnc2)cs1]

087: 3,5-Dibromo-N-[4-methyl-3-(4-pyridin-3-yl-thiazol-2-ylamino)-phenyl]-4-[(3-morpholin-4-yl-propylamino)-methyl]-benzamide

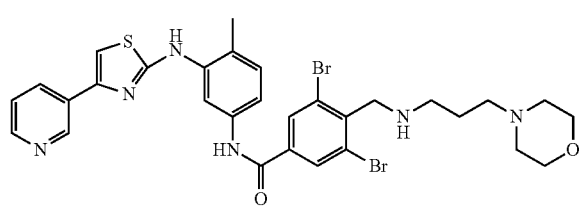 [SMILES: Cc1ccc(NC(=O)c2cc(Br)c(CNCCCN3CCOCC3)c(Br)c2)cc1Nc1nc(-c2cccnc2)cs1]

107: 3,5-Dibromo-N-[4-methyl-3-(4-pyridin-3-yl-thiazol-2-ylamino)-phenyl]-4-piperidin-1-ylmethyl-benzamide

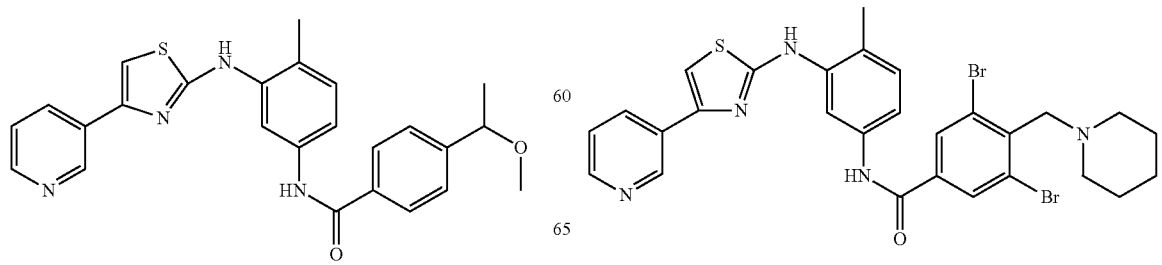

122: 4-(4-Methyl-piperazin-1-ylmethyl)-N-[4-methyl-3-(4-pyridin-2-yl-thiazol-2-ylamino)-phenyl]-benzamide

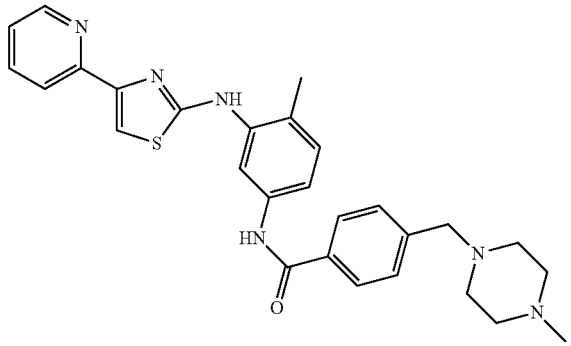 [SMILES: Cc1ccc(NC(=O)c2ccc(CN3CCN(C)CC3)cc2)cc1Nc1nc(-c2ccccn2)cs1]

111: N-{3-[4-(3-Fluoro-phenyl)-thiazol-2-ylamino]-4-methyl-phenyl}-4-(4-methyl-piperazin-1-ylmethyl)-benzamide

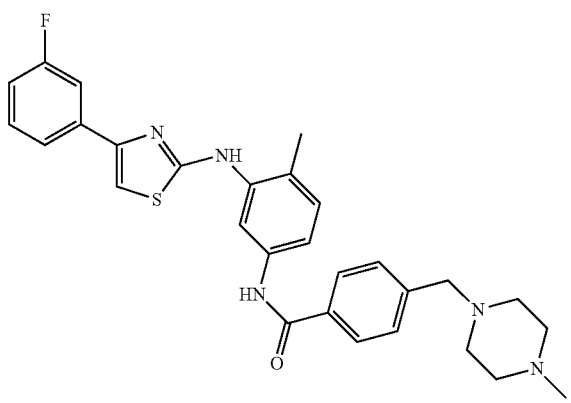 [SMILES: Cc1ccc(NC(=O)c2ccc(CN3CCN(C)CC3)cc2)cc1Nc1nc(-c2cccc(F)c2)cs1]

118: N-{3-[4-(2-Fluoro-phenyl)-thiazol-2-ylamino]-4-methyl-phenyl}-4-(4-methyl-piperazin-1-ylmethyl)-benzamides

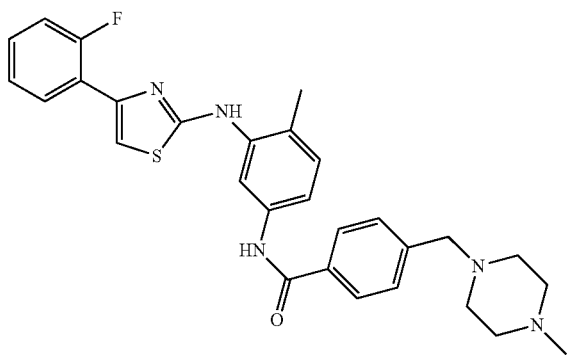 [SMILES: Cc1ccc(NC(=O)c2ccc(CN3CCN(C)CC3)cc2)cc1Nc1nc(-c2ccccc2F)cs1]

Among compounds of formula II, the invention is particularly embodied by the compounds wherein X is a -aryl-substituted group, corresponding to the 3-Disubstituted-amino-N-[3-(thiazol-2-ylamino)-phenyl]-benzamide family and the following formula II-5:

FORMULA II-5

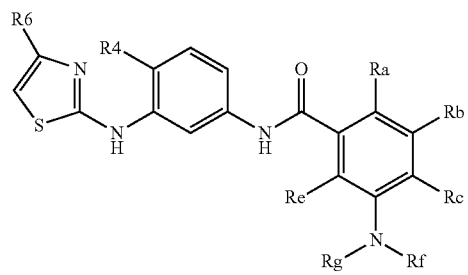

wherein Ra, Rb, Rc, Re, Rf, Rg are independently chosen from H or an organic group that can be selected for example from a linear or branched alkyl group containing from 1 to 10 carbon atoms optionally substituted with at least one heteroatom and/or bearing a pendant basic nitrogen functionality; a cycloalkyl, an aryl or heteroaryl group optionally substituted with a heteroatom, notably a halogen selected from I, Cl, Br and F or bearing a pendant basic nitrogen functionality; or a cycloalkyl, an aryl or heteroaryl group optionally substituted with a cycloalkyl, an aryl or heteroaryl group optionally substituted with an heteroatom, notably a halogen selected from I, Cl, Br and F or bearing a pendant basic nitrogen functionality;

or a NRR' group where R and R' are H or a linear or branched alkyl group containing from 1 to 10 carbon atoms optionally substituted with at least one heteroatom and/or bearing a pendant basic nitrogen functionality; a cycloalkyl, an aryl or heteroaryl group optionally substituted with a heteroatom, notably a halogen selected from I, Cl, Br and F or bearing a pendant basic nitrogen functionality; or a cycloalkyl, an aryl or heteroaryl group optionally substituted with a cycloalkyl, an aryl or heteroaryl group optionally substituted with an heteroatom, notably a halogen selected from I, Cl, Br and F or bearing a pendant basic nitrogen functionality;

or an OR group where R is H or a linear or branched alkyl group containing from 1 to 10 carbon atoms optionally substituted with at least one heteroatom and/or bearing a pendant basic nitrogen functionality; a cycloalkyl, an aryl or heteroaryl group optionally substituted with a heteroatom, notably a halogen selected from I, Cl, Br and F or bearing a pendant basic nitrogen functionality; or a cycloalkyl, an aryl or heteroaryl group optionally substituted with a cycloalkyl, an aryl or heteroaryl group optionally substituted with an heteroatom, notably a halogen selected from I, Cl, Br and F or bearing a pendant basic nitrogen functionality; a —SO2-R' group wherein R' is an alkyl, cycloalkyl, aryl or heteroaryl optionally substituted with a heteroatom, notably a halogen selected from I, Cl, Br and F or bearing a pendant basic nitrogen functionality;

or a NRaCORb group where Ra and Rb are H or a linear or branched alkyl group containing from 1 to 10 carbon atoms optionally substituted with at least one heteroatom and/or bearing a pendant basic nitrogen functionality; a cycloalkyl, an aryl or heteroaryl group optionally substituted with a heteroatom, notably a halogen selected from I, Cl, Br and F or bearing a pendant basic nitrogen functionality; or a cycloalkyl, an aryl or heteroaryl group optionally substituted with a cycloalkyl, an aryl or heteroaryl group optionally substituted with an heteroatom, notably a halogen selected from I, Cl, Br and F or bearing a pendant basic nitrogen functionality;

or a NRaCONRbRc group where Ra and Rb are H or a linear or branched alkyl group containing from 1 to 10 carbon atoms optionally substituted with at least one heteroatom and/or bearing a pendant basic nitrogen functionality; a cycloalkyl, an aryl or heteroaryl group optionally substituted with a heteroatom, notably a halogen selected from I, Cl, Br and F or bearing a pendant basic nitrogen functionality; or a cycloalkyl, an aryl or heteroaryl group optionally substituted with a cycloalkyl, an aryl or heteroaryl group optionally substituted with an heteroatom, notably a halogen selected from I, Cl, Br and F or bearing a pendant basic nitrogen functionality;

or a COOR, where R is a linear or branched alkyl group containing from 1 to 10 carbon atoms atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

or a CONRaRb, where Ra and Rb are a hydrogen or a linear or branched alkyl group containing from 1 to 10 carbon atoms atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

or an NHCOOR, where R is a linear or branched alkyl group containing from 1 to 10 carbon atoms atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

an OSO$_2$R, where R is a linear or branched alkyl group containing from 1 to 10 carbon atoms atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

or an NRaOSO$_2$Rb, where Ra and Rb are a linear or branched alkyl group containing from 1 to 10 carbon atoms atoms optionally substituted with at least one heteroatom (for example a halogen) and/or bearing a pendant basic nitrogen functionality; Ra can also be a hydrogen; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

or a —SO2-R group wherein R is an alkyl, cycloalkyl, aryl or heteroaryl optionally substituted with an heteroatom, notably a halogen selected from I, Cl, Br and F or bearing a pendant basic nitrogen functionality; or a —CO—R or a —CO—NRR' group, wherein R and R' are independently chosen from H, an alkyl, a cycloalkyl, an aryl or heteroaryl group optionally substituted with at least one heteroatom, notably selected from I, Cl, Br and F, and/or bearing a pendant basic nitrogen functionality.

Ra, Rb, Rc, Re can also be halogen such as Cl, F, Br, I or trifluoromethyl;

$R^4$ is hydrogen, halogen or a linear or branched alkyl group containing from 1 to 10 carbon atoms, trifluoromethyl or alkoxy;

$R^6$ is one of the following:

(i) an aryl group such as phenyl or a substituted variant thereof bearing any combination, at any one ring position, of one or more substituents such as halogen, alkyl groups containing from 1 to 10 carbon atoms, trifluoromethyl, and alkoxy;

(ii) a heteroaryl group such as a 2, 3, or 4-pyridyl group, which may additionally bear any combination of one or more substituents such as halogen, alkyl groups containing from 1 to 10 carbon atoms, trifluoromethyl and alkoxy;

(iii) a five-membered ring aromatic heterocyclic group such as for example 2-thienyl, 3-thienyl, 2-thiazolyl, 4-thiazolyl, 5-thiazolyl, which may additionally bear any combination of one or more substituents such as halogen, an alkyl group containing from 1 to 10 carbon atoms, trifluoromethyl, and alkoxy;

iv) H, a halogen selected from I, F, Cl or Br; NH2, NO2 or SO2-R, wherein R is a linear or branched alkyl group containing one or more group such as 1 to 10 carbon atoms, and optionally substituted with at least one heteroatom, notably a halogen selected from I, Cl, Br and F, and/or bearing a pendant basic nitrogen functionality.

EXAMPLES

088: 3-Dimethylamino-N-[4-methyl-3-(4-pyridin-3-yl-thiazol-2-ylamino)-phenyl]-benzamide

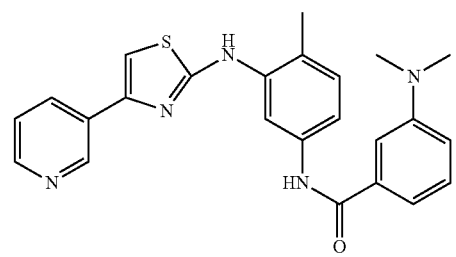 [SMILES: Cc1ccc(NC(=O)c2cccc(N(C)C)c2)cc1Nc1nc(-c2cccnc2)cs1]

beige powder mp: 197-198° C.

$^1$H NMR (DMSO-d$^6$): δ=2.32 (s, 3H); 3.03 (s, 6H); 6.97 (d, J=6.4 Hz, 1H); 7.23-7.56 (m, 7H); 8.37 (d, J=7.3 Hz, 1H); 8.53 (d, J=4.7 Hz, 1H); 8.63 (s, 1H); 9.20 (s, 1H); 9.48 (s, 1H); 10.15 (s, 1H)

089: 3-(4-Methyl-piperazin-1-yl)-N-[4-methyl-3-(4-pyridin-3-yl-thiazol-2-ylamino)-phenyl]-benzamide

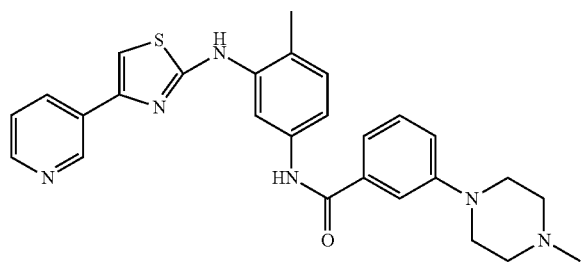 [SMILES: Cc1ccc(NC(=O)c2cccc(N3CCN(C)CC3)c2)cc1Nc1nc(-c2cccnc2)cs1]

beige powder mp: 274-246° C.
$^1$H RMN (DMSO-d$^6$) δ=2.23 (s, 3H); 2.24-2.30 (m, 4H); 3.22-3.27 (m, 4H); 7.07-7.20 (m, 2H); 7.36-7.53 (m, 6H); 8.31 (d, J=7.5 Hz, 1H); 8.47 (d, J=3.7 Hz, 1H); 8.58 (s, 1H); 9.12 (d, J=7.8 Hz, 1H); 9.44 (s, 1H); 10.12 (s, 1H)

090: N-[4-Methyl-3-(4-pyridin-3-yl-thiazol-2-ylamino)-phenyl]-3-morpholin-4-yl-benzamide

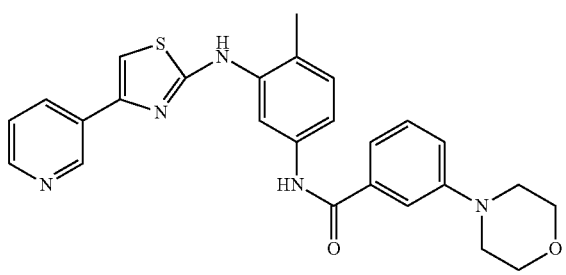 [SMILES: Cc1ccc(NC(=O)c2cccc(N3CCOCC3)c2)cc1Nc1nc(-c2cccnc2)cs1]

beige powder mp: 247-248° C.
$^1$H RMN (CDCl$_3$) δ=1.50 (s, 3H); 3.15-3.18 (m, 4H); 3.79-3.82 (m, 3H); 6.85 (s, 1H); 7.00-7.30 (m, 7H); 7.41 (s, 1H); 7.75 (s, 1H); 8.08 (d, J=7.9 Hz, 1H); 8.22 (d, J=1.7 Hz, 1H); 8.46 (dd, J=1.3 Hz, J=4.7 Hz, 1H); 9.01 (d, J=1.6 Hz, 1H)

Among the compounds of formula II, the invention is particularly embodied by the compounds wherein X is a —OR group, corresponding to the family [3-(Thiazol-2-ylamino)-phenyl]-carbamate and the following formula II-6

FORMULA II-6

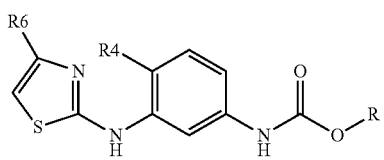

wherein R is independently chosen from an organic group that can be selected for example from a linear or branched alkyl group containing from 1 to 10 carbon atoms optionally substituted with at least one heteroatom and/or bearing a pendant basic nitrogen functionality; a cycloalkyl, an aryl or heteroaryl group optionally substituted with an heteroatom, notably a halogen selected from I, Cl, Br and F and/or bearing a pendant basic nitrogen functionality; or a cycloalkyl, an aryl or heteroaryl group optionally substituted with a cycloalkyl, an aryl or heteroaryl group optionally substituted with a heteroatom, notably a halogen selected from I, Cl, Br and F and/or bearing a pendant basic nitrogen functionality;

R$^4$ is hydrogen, halogen or a linear or branched alkyl group containing from 1 to 10 carbon atoms, trifluoromethyl or alkoxy;

R$^6$ is one of the following:
(i) an aryl group such as phenyl or a substituted variant thereof bearing any combination, at any one ring position, of one or more substituents such as halogen, alkyl groups containing from 1 to 10 carbon atoms, trifluoromethyl, and alkoxy;
(ii) a heteroaryl group such as a 2, 3, or 4-pyridyl group, which may additionally bear any combination of one or more substituents such as halogen, alkyl groups containing from 1 to 10 carbon atoms, trifluoromethyl and alkoxy;
(iii) a five-membered ring aromatic heterocyclic group such as for example 2-thienyl, 3-thienyl, 2-thiazolyl, 4-thiazolyl, 5-thiazolyl, which may additionally bear any combination of one or more substituents such as halogen, an alkyl group containing from 1 to 10 carbon atoms, trifluoromethyl, and alkoxy;
iv) H, a halogen selected from I, F, Cl or Br; NH2, NO2 or SO2-R, wherein R is a linear or branched alkyl group containing one or more group such as 1 to 10 carbon atoms, and optionally substituted with at least one heteroatom, notably a halogen selected from I, Cl, Br and F, and/or bearing a pendant basic nitrogen functionality

EXAMPLES

097: [4-Methyl-3-(4-pyridin-3-yl-thiazol-2-ylamino)-phenyl]-carbamic acid isobutyl ester

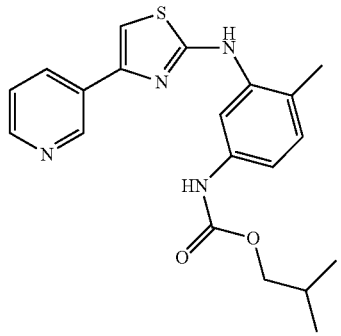 [SMILES: Cc1ccc(NC(=O)OCC(C)C)cc1Nc1nc(-c2cccnc2)cs1]

098: 2-(2-methyl-5-tert-butoxycarbonylamino)phenyl-4-(3-pyridyl)-thiazole

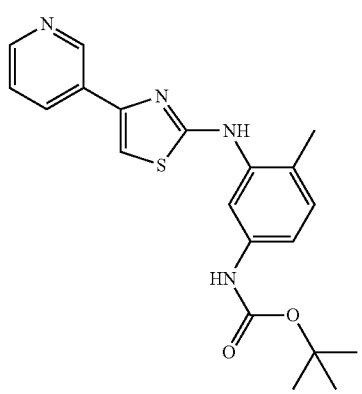 [SMILES: Cc1ccc(NC(=O)OC(C)(C)C)cc1Nc1nc(-c2cccnc2)cs1]

In a second embodiment, the invention is directed to a process for manufacturing a compound of formula I depicted above. This entails the condensation of a substrate of general formula 10 with a thiourea of the type 11.

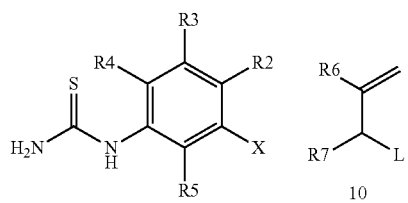

11a: X = NH—R1
11b: X = NH2
11c: X = NH—PG
11d: X = NO2

Substituent "L" in formula 10 is a nucleofugal leaving group in nucleophilic substitution reactions (for example, L can be selected from chloro, bromo, iodo, toluenesulfonyloxy, methanesulfonyloxy, trifluoromethanesulfonyloxy, etc., with L being preferentially a bromo group).

Group R1 in formula 11a corresponds to group R1 as described in formula I.

Group "PG" in formula 11c is a suitable protecting group of a type commonly utilized by the person skilled in the art.

The reaction of 10 with 1 a-d leads to a thiozole-type product of formula 12a-d.

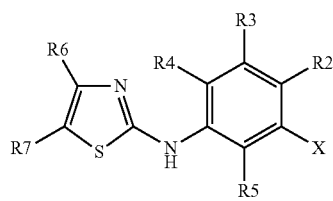

12a: X = NH—R1
12b: X = NH2
12c: X = NH—PG
12d: X = NO2

Formula 12a is the same as formula I. Therefore, R1 in 12a corresponds to R1 in formula I.

Formula 12b describes a precursor to compounds of formula I which lack substituent R1. Therefore, in a second phase of the synthesis, substituent R1 is connected to the free amine group in 12b, leading to the complete structure embodied by formula I:

12b+"R1"→I

The introduction of R1, the nature of which is as described on page 3 for the general formula I, is achieved by the use of standard reactions that are well known to the person skilled in the art, such as alkylation, acylation, sulfonylation, formation of ureas, etc.

Formula 12c describes an N-protected variant of compound 12b. Group "PG" in formula 12c represents a protecting group of the type commonly utilized by the person skilled in the art. Therefore, in a second phase of the synthesis, group PG is cleaved to transform compound 12c into compound 12b. Compound 12b is subsequently advanced to structures of formula I as detailed above.

Formula 12d describes a nitro analogue of compound 12b. In a second phase of the synthesis, the nitro group of compound 12d is reduced by any of the several methods utilized by the person skilled in the art to produce the corresponding amino group, namely compound 12b. Compound 12b thus obtained is subsequently advanced to structures of formula I as detailed above.

Examples of Compound synthesis

General: All chemicals used were commercial reagent grade products. Dimethylformamide (DMF), methanol (MeOH) were of anhydrous commercial grade and were used without further purification. Dichloromethane and tetrahydrofuran (THF) were freshly distilled under a stream of argon before use. The progress of the reactions was monitored by thin layer chromatography using precoated silica gel 60F 254, Fluka TLC plates, which were visualized under UV light. Multiplicities in $^1$H NMR spectra are indicated as singlet (s), broad singlet (br s), doublet (d), triplet (t), quadruplet (q), and multiplet (m) and the NMR spectrum were realized on a 300 MHz Bruker spectrometer.

3-Bromoacetyl-pyridine, HBr salt

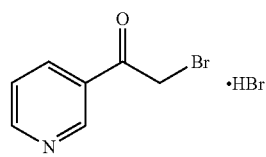

Dibromine (17.2 g, 108 mmol) was added dropwise to a cold (0° C.) solution of 3-acetyl-pyridine (12 g, 99 mmol) in acetic acid containing 33% of HBr (165 mL) under vigourous stirring. The vigorously stirred mixture was warmed to 40° C. for 2 h and then to 75° C. After 2 h at 75° C., the mixture was cooled and diluted with ether (400 mL) to precipitate the product. which was recovered by filtration and washed with ether and acetone to give white crystals (100%). This material may be recrystallised from methanol and ether.

IR (neat): 3108, 2047, 2982, 2559, 1709, 1603, 1221, 1035, 798 cm$^{-1}$—$^1$H NMR (DMSO-d$^6$) δ=5.09 (s, 2H, CH$_2$Br); 7.88 (m, 1H, pyridyl-H); 8.63 (m, 1H, pyridyl-H); 8.96 (m, 1H, pyridyl-H); 9.29 (m, 1H, pyridyl-H).

Methyl-[4-(1-N-methyl-piperazino)-methyl]-benzoate

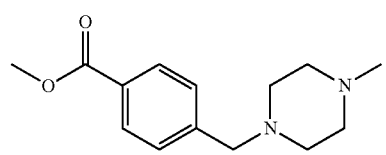

To methyl-4-formyl benzoate (4.92 g, 30 mmol) and N-methyl-piperazine (3.6 mL, 32 mmol) in acetonitrile (100 mL) was added dropwise 2.5 mL of trifluoroacetic acid. The reaction mixture was stirred at room temperature for 1 h. After slow addition of sodium cyanoborohydride (2 g, 32 mmol), the solution was left stirring overnight at room temperature. Water (10 mL) was then added to the mixture, which was further acidified with 1N HCl to pH=6-7. The acetonitrile was removed under reduced pressure and the residual aqueous solution was extracted with diethyl ether (4×30 mL). These extracts were discarded. The aqueous phase was then basified (pH>12) by addition of 2.5N aqueous sodium hydroxyde solution. The crude product was extracted with ethyl acetate (4×30 mL). The combined organic layers were dried over MgSO$_4$ and concentrated under reduced pressure to afford a slightly yellow oil which became colorless after purification by Kugelrohr distillation (190° C.) in 68% yield.

IR (neat): 3322, 2944, 2802, 1721, 1612, 1457, 1281, 1122, 1012—$^1$H NMR (CDCl$_3$) δ=2.27 (s, 3H, NCH$_3$); 2.44 (m, 8H, 2×NCH$_2$CH$_2$N); 3.53 (s, 2H, ArCH$_2$N); 3.88 (s, 3H, OCH$_3$); 7.40 (d, 2H, J=8.3 Hz, 2×ArH); 7.91 (d, 2H, J=8.3 Hz, 2×ArH)—$^{13}$C NMR (CDCl$_3$) δ=45.8 (NCH$_3$); 51.8 (OCH$_3$); 52.9 (2×CH$_2$N); 54.9 (2×CH$_2$N); 62.4 (ArCH$_2$N); 128.7 (2×ArC); 129.3 (2×ArC); 143.7 (ArC); 166.7 (ArCO$_2$CH$_3$)—MS CI (m/z) (%): 249 (M+1, 100%).

2-Methyl-5-tert-butoxycarbonylamino-aniline

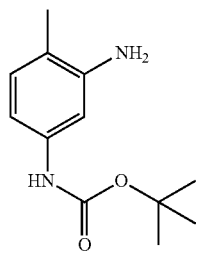 [SMILES: Cc1ccc(NC(=O)OC(C)(C)C)cc1N]

A solution of di-tert-butyldicarbonate (70 g, 320 mmol) in methanol (200 mL) was added over 2 h to a cold (−10° C.) solution of 2,4-diaminotoluene (30 g, 245 mmol) and triethylamine (30 mL) in methanol (15 mL). The reaction was followed by thin layer chromatography (hexane/ethyl acetate, 3:1) and stopped after 4 h by adding 50 mL of water. The mixture was concentrated in vacuo and the residue was dissolved in 500 ml of ethyl acetate. This organic phase was washed with water (1×150 mL) and brine (2×150 mL), dried over MgSO$_4$, and concentrated under reduced pressure. The resulting light brown solid was washed with small amounts of diethyl ether to give off-white crystals of 2-methyl-5-tert-butoxycarbonylamino-aniline in 67% yield.

IR (neat): 3359; 3246; 2970; 1719; 1609; 1557; 1173; 1050 cm$^{-1}$—$^1$H NMR (CDCl$_3$): δ=1.50 (s, 9H, tBu); 2.10 (s, 3H, ArCH$_3$); 3.61 (br s, 2H, NH$_2$); 6.36 (br s, 1H, NH); 6.51 (dd, 1H, J=7.9 Hz, 2.3 Hz, ArH); 6.92 (d, 1H, J=7.9 Hz, ArH); 6.95 (s, 1H, ArH)—$^{13}$C NMR (CDCl$_3$) δ=16.6 (ArCH$_3$); 28.3 (C(CH$_3$)$_3$); 80.0 (C(CH$_3$)$_3$); 105.2 (ArC); 108.6 (ArC); 116.9 (ArC); 130.4 (ArC-CH$_3$); 137.2 (ArC-NH); 145.0 (ArC-NH$_2$); 152.8 (COOtBu)

MS ESI (m/z) (%): 223 (M+1), 167 (55, 100%).

N-(2-methyl-5-tert-butoxycarbonylamino)phenyl-thiourea

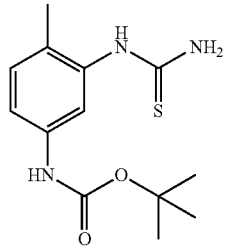 [SMILES: Cc1ccc(NC(=O)OC(C)(C)C)cc1NC(N)=S]

Benzoyl chloride (5.64 g, 80 mmol) was added dropwise to a well-stirred solution of ammonium thiocyanate (3.54 g, 88 mmol) in acetone (50 mL). The mixture was refluxed for 15 min, then, the hydrobromide salt of 2-methyl-5-tert-butoxycarbonylamino-aniline (8.4 g, 80 mmol) was added slowly portionswise. After 1 h, the reaction mixture was poured into ice-water (350 ml) and the bright yellow precipitate was isolated by filtration. This crude solid was then refluxed for 45 min in 70 mL of 2.5 N sodium hydroxide solution. The mixture was cooled down and basified with ammonium hydroxide. The precipitate of crude thiourea was recovered by filtration and dissolved in 150 mL of ethyl acetate. The organic phase was washed with brine, dried over Na$_2$SO$_4$, and concentrated under reduced pressure. The residue was purified by column chromatography (hexane/ethyl acetate, 1:1) to afford 63% of N-(2-methyl-5-tert-butoxycarbonylamino) phenyl-thiourea as a white solid.

IR (neat): 3437, 3292, 3175, 2983, 1724, 1616, 1522, 1161, 1053 cm$^{-1}$—$^1$H NMR (DMSO-d$^6$) δ=1.46 (s, 9H, tBu); 2.10 (s, 3H, ArCH$_3$); 3.60 (br s, 2H, NH$_2$); 7.10 (d, 1H, J=8.29 Hz, ArH); 7.25 (d, 1H, J=2.23 Hz, ArH); 7.28 (d, 1H, J=2.63 Hz, ArH); 9.20 (s, 1H, ArNH); 9.31 (s, 1H, ArNH)—$^{13}$C NMR (DMSO-d$^6$) δ=25.1 (ArCH$_3$); 28.1 (C(CH$_3$)$_3$); 78.9 (C(CH$_3$)$_3$); 116.6 (ArC); 117.5 (ArC); 128.0 (ArC); 130.4 (ArC-CH$_3$); 136.5 (ArC-NH); 137.9 (ArC-NH); 152.7 (COOtBu); 181.4 (C=S)—MS CI (m/z): 282 (M+1, 100%); 248 (33); 226 (55); 182 (99); 148 (133); 93 (188).

2-(2-methyl-5-tert-butoxycarbonylamino)phenyl-4-(3-pyridyl)-thiazole

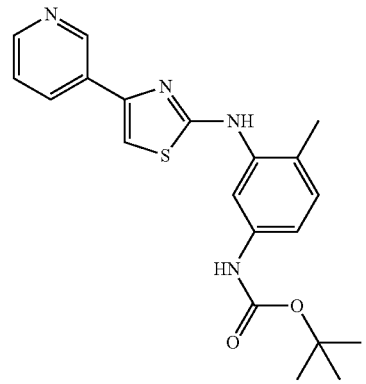 [SMILES: Cc1ccc(NC(=O)OC(C)(C)C)cc1Nc1nc(-c2cccnc2)cs1]

A mixture of 3-bromoacetyl-pyridine, HBr salt (0.81 g, 2.85 mmol), N-(2-methyl-5-tert-butoxycarbonylamino)phenyl-thiourea (0.8 g, 2.85 mmol) and KHCO$_3$ (~0.4 g) in ethanol (40 mL) was heated at 75° C. for 20 h. The mixture was cooled, filtered (removal of KHCO$_3$) and evaporated under reduced pressure. The residue was dissolved in CHCl$_3$ (40 mL) and washed with saturated aqueous sodium hydrogen carbonate solution and with water. The organic layer was dried over Na$_2$SO$_4$ and concentrated. Column chromatographic purification of the residue (hexane/ethyl acetate, 1:1) gave the desired thiazole in 70% yield as an orange solid IR (neat): 3380, 2985, 2942, 1748, 1447, 1374, 1239, 1047, 938—$^1$H NMR (CDCl$_3$) δ=1.53 (s, 9H, tBu); 2.28 (s, 3H, ArCH$_3$); 6.65 (s, 1H, thiazole-H); 6.89 (s, 1H); 6.99 (dd, 1H, J=8.3 Hz, 2.3 Hz); 7.12 (d, 2H, J=8.3 Hz); 7.35 (dd, 1H, J=2.6 Hz, 4.9 Hz); 8.03 (s, 1H); 8.19 (dt, 1H, J=1.9 Hz, 7.9 Hz); 8.54 (br s, 1H, NH); 9.09 (s, 1H, NH)—$^{13}$C NMR (CDCl$_3$) δ=18.02 (ArCH$_3$); 29.2 (C(CH$_3$)$_3$); 81.3 (C(CH$_3$)$_3$); 104.2 (thiazole-C); 111.6; 115.2; 123.9; 124.3; 131.4; 132.1; 134.4; 139.5; 148.2; 149.1; 149.3; 153.6; 167.3 (C=O)—MS CI (m/z) (%): 383 (M+1, 100%); 339 (43); 327 (55); 309 (73); 283 (99); 71 (311).

2-(2-methyl-5-amino)phenyl-4-(3-pyridyl)-thiazole

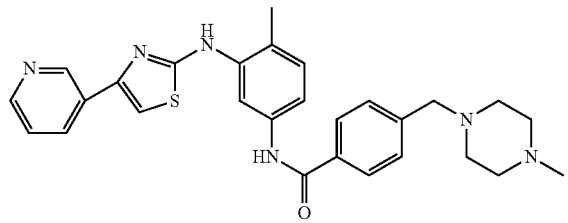 [SMILES: Cc1ccc(NC(=O)c2ccc(CN3CCN(C)CC3)cc2)cc1Nc1nc(-c2cccnc2)cs1]

2-(2-methyl-5-tert-butoxycarbonylamino)phenyl-4-(3-pyridyl)-thiazole (0.40 g, 1.2 mmol) was dissolved in 10 mL of 20% TFA/CH$_2$Cl$_2$. The solution was stirred at room temperature for 2 h, then it was evaporated under reduced pressure. The residue was dissolved in ethyl acetate. The organic layer was washed with aqueous 1N sodium hydroxide solution, dried over MgSO$_4$, and concentrated to afford 2-(2-methyl-5-amino)phenyl-4-(3-pyridyl)-thiazole as a yellow-orange solid in 95% yield. This crude product was used directly in the next step.

A 2M solution of trimethyl aluminium in toluene (2.75 mL) was added dropwise to a cold (0° C.) solution of 2-(2-methyl-5-amino)phenyl-4-(3-pyridyl)-thiazole (0.42 g, 1.5 mmol) in anhydrous dichloromethane (10 mL) under argon atmosphere. The mixture was warmed to room temperature and stirred at room temperature for 30 min. A solution of methyl-4-(1-N-methyl-piperazino)-methyl benzoate (0.45 g, 1.8 mmol) in anhydrous dichloromethane (1 mL) and added slowly, and the resulting mixture was heated at reflux for 5 h. The mixture was cooled to 0° C. and quenched by dropwise addition of a 4N aqueous sodium hydroxide solution (3 mL). The mixture was extracted with dichloromethane (3×20 mL). The combined organic layers were washed with brine (3×20 mL) and dried over anhydrous MgSO$_4$. (2-(2-methyl-5-amino)phenyl-4-(3-pyridyl)-thiazole) is obtained in 72% after purification by column chromatography (dichloromethane/methanol, 3:1)

IR (neat): 3318, 2926, 1647, 1610, 1535, 1492, 1282, 1207, 1160, 1011, 843—$^1$H NMR (CDCl$_3$) δ=2.31 (br s, 6H, ArCH$_3$+NCH$_3$); 2.50 (br s, 8H, 2×NCH$_2$CH$_2$N); 3.56 (s, 2H, ArCH$_2$N); 6.89 (s, 1H, thiazole H); 7.21-7.38 (m, 4H); 7.45 (m, 2H); 7.85 (d, 2H, J=8.3 Hz); 8.03 (s, 1H); 8.13 (s, 1H); 8.27 (s, 1H); 8.52 (br s, 1H); 9.09 (s, 1H, NH)—$^{13}$C NMR (CDCl$_3$) δ=17.8 (ArCH$_3$); 46.2 (NCH$_3$); 53.3 (NCH$_2$); 55.3 (NCH$_2$); 62.8 (ArCH$_2$N); 99.9 (thiazole-C); 112.5; 123.9; 125.2; 127.5; 129.6; 131.6; 133.7; 134.0; 137.6; 139.3; 142.9; 148.8; 149.1; 166.2 (C=O); 166.7 (thiazole C—NH)—MS CI (m/z) (%): 499 (M+H, 100%); 455 (43); 430 (68); 401 (97); 374 (124); 309 (189); 283 (215); 235 (263); 121 (377); 99 (399).

In a third embodiment, the invention relates to a pharmaceutical composition comprising a compound as depicted above.

Such medicament can take the form of a pharmaceutical composition adapted for oral administration, which can be formulated using pharmaceutically acceptable carriers well known in the art in suitable dosages. Such carriers enable the pharmaceutical compositions to be formulated as tablets, pills, dragees, capsules, liquids, gels, syrups, slurries, suspensions, and the like, for ingestion by the patient. In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Maack Publishing Co., Easton, Pa.).

The composition of the invention can also take the form of a pharmaceutical or cosmetic composition for topical administration.

Such compositions may be presented in the form of a gel, paste, ointment, cream, lotion, liquid suspension aqueous, aqueous-alcoholic or, oily solutions, or dispersions of the lotion or serum type, or anhydrous or lipophilic gels, or emulsions of liquid or semi-solid consistency of the milk type, obtained by dispersing a fatty phase in an aqueous phase or vice versa, or of suspensions or emulsions of soft, semi-solid consistency of the cream or gel type, or alternatively of microemulsions, of microcapsules, of microparticles or of vesicular dispersions to the ionic and/or nonionic type. These compositions are prepared according to standard methods.

The composition according to the invention comprises any ingredient commonly used in dermatology and cosmetic. It may comprise at least one ingredient selected from hydrophilic or lipophilic gelling agents, hydrophilic or lipophilic active agents, preservatives, emollients, viscosity enhancing polymers, humectants, surfactants, preservatives, antioxidants, solvents, and fillers, antioxidants, solvents, perfumes, fillers, screening agents, bactericides, odor absorbers and coloring matter.

As oils which can be used in the invention, mineral oils (liquid paraffin), vegetable oils (liquid fraction of shea butter, sunflower oil), animal oils, synthetic oils, silicone oils (cyclomethicone) and fluorinated oils may be mentioned. Fatty alcohols, fatty acids (stearic acid) and waxes (paraffin, carnauba, beeswax) may also be used as fatty substances.

As emulsifiers which can be used in the invention, glycerol stearate, polysorbate 60 and the PEG-6/PEG-32/glycol stearate mixture are contemplated.

As hydrophilic gelling agents, carboxyvinyl polymers (carbomer), acrylic copolymers such as acrylate/alkylacrylate copolymers, polyacrylamides, polysaccharides such as hydroxypropylcellulose, clays and natural gums may be mentioned, and as lipophilic gelling agents, modified clays such as bentones, metal salts of fatty acids such as aluminum stearates and hydrophobic silica, or alternatively ethylcellulose and polyethylene may be mentioned.

As hydrophilic active agents, proteins or protein hydrolysates, amino acids, polyols, urea, allantoin, sugars and sugar derivatives, vitamins, starch and plant extracts, in particular those of Aloe vera may be used.

As lipophilic active, agents, retinol (vitamin A) and its derivatives, tocopherol (vitamin E) and its derivatives, essential fatty acids, ceramides and essential oils may be used. These agents add extra moisturizing or skin softening features when utilized.

In addition, a surfactant can be included in the composition so as to provide deeper penetration of the compound capable of depleting mast cells, such as a tyrosine kinase inhibitor, preferably a c-kit inhibitor.

Among the contemplated ingredients, the invention embraces penetration enhancing agents selected for example from the group consisting of mineral oil, water, ethanol, triacetin, glycerin and propylene glycol; cohesion agents selected for example from the group consisting of polyisobutylene, polyvinyl acetate and polyvinyl alcohol, and thickening agents.

Chemical methods of enhancing topical absorption of drugs are well known in the art. For example, compounds with penetration enhancing properties include sodium lauryl sulfate (Dugard, P. H. and Sheuplein, R. J., "Effects of Ionic Surfactants on the Permeability of Human Epidermis: An Electrometric Study," J. Ivest. Dermatol., V. 60, pp. 263-69, 1973), lauryl amine oxide (Johnson et. al., U.S. Pat. No. 4,411,893), azone (Rajadhyaksha, U.S. Pat. Nos. 4,405,616 and 3,989,816) and decylmethyl sulfoxide (Sekura, D. L. and Scala, J., "The Percutaneous Absorption of Alkylmethyl Sulfides," Pharmacology of the Skin, Advances In Biology of Skin, (Appleton-Century Craft) V. 12, pp. 257-69, 1972). It has been observed that increasing the polarity of the head group in amphoteric molecules increases their penetration-enhancing properties but at the expense of increasing their skin irritating properties (Cooper, E. R. and Berner, B., "Interaction of Surfactants with Epidermal Tissues: Physiochemical Aspects," Surfactant Science Series, V. 16, Reiger, M. M. ed. (Marcel Dekker, Inc.) pp. 195-210, 1987).

A second class of chemical enhancers are generally referred to as co-solvents. These materials are absorbed topically relatively easily, and, by a variety of mechanisms, achieve permeation enhancement for some drugs. Ethanol (Gale et. al., U.S. Pat. No. 4,615,699 and Campbell et. al., U.S. Pat. Nos. 4,460,372 and 4,379,454), dimethyl sulfoxide (U.S. Pat. Nos. 3,740,420 and 3,743,727, and U.S. Pat. No. 4,575,515), and glycerine derivatives (U.S. Pat. No. 4,322,433) are a few examples of compounds which have shown an ability to enhance the absorption of various compounds.

The pharmaceutical compositions of the invention can also be intended for administration with aerosolized formulation to target areas of a patient's respiratory tract.

Devices and methodologies for delivering aerosolized bursts of a formulation of a drug is disclosed in U.S. Pat. No. 5,906,202. Formulations are preferably solutions, e.g. aqueous solutions, ethanoic solutions, aqueous/ethanoic solutions, saline solutions, colloidal suspensions and microcrystalline suspensions. For example aerosolized particles comprise the active ingredient mentioned above and a carrier, (e.g., a pharmaceutically active respiratory drug and carrier) which are formed upon forcing the formulation through a nozzle which nozzle is preferably in the form of a flexible porous membrane. The particles have a size which is sufficiently small such that when the particles are formed they remain suspended in the air for a sufficient amount of time such that the patient can inhale the particles into the patient's lungs.

The invention encompasses the systems described in U.S. Pat. No. 5,556,611:
  liquid gas systems (a liquefied gas is used as propellent gas (e.g. low-boiling FCHC or propane, butane) in a pressure container,
  suspension aerosol (the active substance particles are suspended in solid form in the liquid propellent phase),
  pressurized gas system (a compressed gas such as nitrogen, carbon dioxide, dinitrogen monoxide, air is used.

Thus, according to the invention the pharmaceutical preparation is made in that the active substance is dissolved or dispersed in a suitable nontoxic medium and said solution or dispersion atomized to an aerosol, i.e. distributed extremely finely in a carrier gas. This is technically possible for example in the form of aerosol propellent gas packs, pump aerosols or other devices known per se for liquid misting and solid atomizing which in particular permit an exact individual dosage.

Therefore, the invention is also directed to aerosol devices comprising the compound as defined above and such a formulation, preferably with metered dose valves.

The pharmaceutical compositions of the invention can also be intended for intranasal administration.

In this regard, pharmaceutically acceptable carriers for administering the compound to the nasal mucosal surfaces will be readily appreciated by the ordinary artisan. These carriers are described in the Remington's Pharmaceutical Sciences" 16th edition, 1980, Ed. By Arthur Osol, the disclosure of which is incorporated herein by reference.

The selection of appropriate carriers depends upon the particular type of administration that is contemplated. For administration via the upper respiratory tract, the composition can be formulated into a solution, e.g., water or isotonic saline, buffered or unbuffered, or as a suspension, for intranasal administration as drops or as a spray. Preferably, such solutions or suspensions are isotonic relative to nasal secretions and of about the same pH, ranging e.g., from about pH 4.0 to about pH 7.4 or, from pH 6.0 to pH 7.0. Buffers should be physiologically compatible and include, simply by way of example, phosphate buffers. For example, a representative nasal decongestant is described as being buffered to a pH of about 6.2 (Remington's, Id. at page 1445). Of course, the ordinary artisan can readily determine a suitable saline content and pH for an innocuous aqueous carrier for nasal and/or upper respiratory administration.

Common intranasal carriers include nasal gels, creams, pastes or ointments with a viscosity of, e.g., from about 10 to about 3000 cps, or from about 2500 to 6500 cps, or greater, may also be used to provide a more sustained contact with the nasal mucosal surfaces. Such carrier viscous formulations may be based upon, simply by way of example, alkylcelluloses and/or other biocompatible carriers of high viscosity well known to the art (see e.g., Remington's, cited supra. A preferred alkylcellulose is, e.g., methylcellulose in a concentration ranging from about 5 to about 1000 or more mg per 100 ml of carrier. A more preferred concentration of methyl cellulose is, simply by way of example, from about 25 to about mg per 100 ml of carrier.

Other ingredients, such as art known preservatives, colorants, lubricating or viscous mineral or vegetable oils, perfumes, natural or synthetic plant extracts such as aromatic oils, and humectants and viscosity enhancers such as, e.g., glycerol, can also be included to provide additional viscosity, moisture retention and a pleasant texture and odor for the formulation. For nasal administration of solutions or suspensions according to the invention, various devices are available in the art for the generation of drops, droplets and sprays.

A premeasured unit dosage dispenser including a dropper or spray device containing a solution or suspension for delivery as drops or as a spray is prepared containing one or more doses of the drug to be administered and is another object of the invention. The invention also includes a kit containing one or more unit dehydrated doses of the compound, together with any required salts and/or buffer agents, preservatives, colorants and the like, ready for preparation of a solution or suspension by the addition of a suitable amount of water.

Another aspect of the invention is directed to the use of said compound to manufacture a medicament. In other words, the invention embraces a method for treating a disease related to unregulated c-kit transduction comprising administering an effective amount of a compound as defined above to a mammal in need of such treatment.

More particularly, the invention is aimed at a method for treating a disease selected from autoimmune diseases, allergic diseases, bone loss, cancers such as leukemia and GIST, tumor angiogenesis, inflammatory diseases, inflammatory bowel diseases (IBD), interstitial cystitis, mastocytosis, infections diseases, metabolic disorders, fibrosis, diabetes and CNS disorders comprising administering an effective amount a compound depicted above to a mammal in need of such treatment.

The above described compounds are useful for manufacturing a medicament for the treatment of diseases related to unregulated c-kit transduction, including, but not limited to:
  neoplastic diseases such as mastocytosis, canine mastocytoma, human gastrointestinal stromal tumor ("GIST"), small cell lung cancer, non-small cell lung cancer, acute myelocytic leukemia, acute lymphocytic leukemia, myelodysplastic syndrome, chronic myelogenous leukemia, colorectal carcinomas, gastric carcinomas, gastrointestinal stromal tumors, testicular cancers, glioblastomas, solid tumors and astrocytomas
  tumor angiogenesis.
  metabolic diseases such as diabetes mellitus and its chronic complications; obesity; diabete type II; hyperlipidemias and dyslipidemias; atherosclerosis; hypertension; and cardiovascular disease.

allergic diseases such as asthma, allergic rhinitis, allergic sinusitis, anaphylactic syndrome, urticaria, angioedema, atopic dermatitis, allergic contact dermatitis, erythema nodosum, erythema multifoime, cutaneous necrotizing venulitis and insect bite skin inflammation and blood sucking parasitic infestation.

interstitial cystitis.

bone loss (osteoporosis).

inflammatory diseases such as rheumatoid arthritis, conjunctivitis, rheumatoid spondylitis, osteoarthritis, gouty arthritis and other arthritic conditions.

autoimmune diseases such as multiple sclerosis, psoriasis, intestine inflammatory disease, ulcerative colitis, Crohn's disease, rheumatoid arthritis and polyarthritis, local and systemic scleroderma, systemic lupus erythematosus, discoid lupus erythematosus, cutaneous lupus, dermatomyositis, polymyositis, Sjogren's syndrome, nodular panarteritis, autoimmune enteropathy, as well as proliferative glomerulonephritis.

graft-versus-host disease or graft rejection in any organ transplantation including kidney, pancreas, liver, heart, lung, and bone marrow.

Other autoimmune diseases embraced by the invention active chronic hepatitis and chronic fatigue syndrome.

subepidermal blistering disorders such as pemphigus.

Vasculitis.

melanocyte dysfunction associated diseases such as hypermelanosis resulting from melanocyte dysfunction and including lentigines, solar and senile lentigo, Dubreuilh melanosis, moles as well as malignant melanomas. In this regard, the invention embraces the use of the compounds defined above to manufacture a medicament or a cosmetic composition for whitening human skin.

CNS disorders such as psychiatric disorders, migraine, pain, memory loss and nerve cells degeneracy. More particularly, the method according to the invention is useful for the treatment of the following disorders: Depression including dysthymic disorder, cyclothymic disorder, bipolar depression, severe or "melancholic" depression, atypical depression, refractory depression, seasonal depression, anorexia, bulimia, premenstrual syndrome, post-menopause syndrome, other syndromes such as mental slowing and loss of concentration, pessimistic worry, agitation, self-deprecation, decreased libido, pain including, acute pain, postoperative pain, chronic pain, nociceptive pain, cancer pain, neuropathic pain, psychogenic pain syndromes, anxiety disorders including anxiety associated with hyperventilation and cardiac arrhythmias, phobic disorders, obsessive-compulsive disorder, posttraumatic stress disorder, acute stress disorder, generalized anxiety disorder, psychiatric emergencies such as panic attacks, including psychosis, delusional disorders, conversion disorders, phobias, mania, delirium, dissociative episodes including dissociative amnesia, dissociative fugue and dissociative identity disorder, depersonalization, catatonia, seizures, severe psychiatric emergencies including suicidal behaviour, self-neglect, violent or aggressive behaviour, trauma, borderline personality, and acute psychosis, schizophrenia including paranoid schizophrenia, disorganized schizophrenia, catatonic schizophrenia, and undifferentiated schizophrenia, neurodegenerative diseases including Alzheimer's disease, Parkinson's disease, Huntington's disease, the prion diseases, Motor Neurone Disease (WIND), and Amyotrophic Lateral Sclerosis (ALS).

substance use disorders as referred herein include but are not limited to drug addiction, drug abuse, drug habituation, drug dependence, withdrawal syndrome and overdose.

Cerebral ischemia

Fibrosis

Duchenne muscular dystrophy

Regarding mastocytosis, the invention contemplates the use of the compounds as defined above for treating the different categories which can be classified as follows:

The category I is composed by two sub-categories (IA and IB). Category IA is made by diseases in which mast cell infiltration is strictly localized to the skin. This category represents the most frequent form of the disease and includes: i) urticaria pigmentosa, the most common form of cutaneous mastocytosis, particularly encountered in children, ii) diffuse cutaneous mastocytosis, iii) solitary mastocytoma and iv) some rare subtypes like bullous, erythrodermic and teleangiectatic mastocytosis. These forms are characterized by their excellent prognosis with spontaneous remissions in children and a very indolent course in adults. Long term survival of this form of disease is generally comparable to that of the normal population and the translation into another form of mastocytosis is rare. Category IB is represented by indolent systemic disease (SM) with or without cutaneous involvement. These forms are much more usual in adults than in children. The course of the disease is often indolent, but sometimes signs of aggressive or malignant mastocytosis can occur, leading to progressive impaired organ function.

The category II includes mastocytosis with an associated hematological disorder, such as a myeloproliferative or myelodysplastic syndrome, or acute leukemia. These malignant mastocytosis does not usually involve the skin. The progression of the disease depends generally on the type of associated hematological disorder that conditioner the prognosis.

The category III is represented by aggressive systemic mastocytosis in which massive infiltration of multiple organs by abnormal mast cells is common. In patients who pursue this kind of aggressive clinical course, peripheral blood features suggestive of a myeloproliferative disorder are more prominent. The progression of the disease can be very rapid, similar to acute leukemia, or some patients can show a longer survival time.

Finally, the category IV of mastocytosis includes the mast cell leukemia, characterized by the presence of circulating mast cells and mast cell progenitors representing more than 10% of the white blood cells. This entity represents probably the rarest type of leukemia in humans, and has a very poor prognosis, similar to the rapidly progressing variant of malignant mastocytosis. Mast cell leukemia can occur either de novo or as the terminal phase of urticaria pigmentosa or systemic mastocytosis.

The invention also contemplates the method as depicted for the treatment of recurrent bacterial infections, resurging infections after asymptomatic periods such as bacterial cystitis. More particularly, the invention can be practiced for treating FimH expressing bacteria infections such as Gram-negative enterobacteria including *E. coli, Klebsiella pneumoniae, Serratia marcescens, Citrobactor freudii* and *Salmonella typhimurium*.

In this method for treating bacterial infection, separate, sequential or concomitant administration of at least one antibiotic selected bacitracin, the cephalosporins, the penicillins, the aminoglycosides, the tetracyclines, the streptomycins and the macrolide antibiotics such as erythromycin; the fluoroquinolones, actinomycin, the sulfonamides and trimethoprim, is of interest.

In one preferred embodiment, the invention is directed to a method for treating neoplastic diseases such as mastocytosis, canine mastocytoma, human gastrointestinal stromal tumor ("GIST"), small cell lung cancer, non-small cell lung cancer, acute myelocytic leukemia, acute lymphocytic leukemia, myelodysplastic syndrome, chronic myelogenous leukemia, colorectal carcinomas, gastric carcinomas, gastrointestinal stromal tumors, testicular cancers, glioblastomas, and astrocytomas comprising administering a compound as defined herein to a human or mammal, especially dogs and cats, in need of such treatment.

In one other preferred embodiment, the invention is directed to a method for treating allergic diseases such as asthma, allergic rhinitis, allergic sinusitis, anaphylactic syndrome, urticaria, angioedema, atopic dermatitis, allergic contact dermatitis, erythema nodosum, erythema multiforme, cutaneous necrotizing venulitis and insect bite skin inflammation and blood sucking parasitic infestation comprising administering a compound as defined herein to a human or mammal, especially dogs and cats, in need of such treatment.

In still another preferred embodiment, the invention is directed to a method for treating inflammatory diseases such as rheumatoid arthritis, conjunctivitis, rheumatoid spondylitis, osteoarthritis, gouty arthritis and other arthritic conditions comprising administering a compound as defined herein to a human in need of such treatment.

In still another preferred embodiment, the invention is directed to a method for treating autoimmune diseases such as multiple sclerosis, psoriasis, intestine inflammatory disease, ulcerative colitis, Crohn's disease, rheumatoid arthritis and polyarthritis, local and systemic scleroderma, systemic lupus erythematosus, discoid lupus erythematosus, cutaneous lupus, dermatomyositis, polymyositis, Sjogren's syndrome, nodular panarteritis, autoimmune enteropathy, as well as proliferative glomerulonephritis comprising administering a compound as defined herein to a human in need of such treatment.

In still another preferred embodiment, the invention is directed to a method for treating graft-versus-host disease or graft rejection in any organ transplantation including kidney, pancreas, liver, heart, lung, and bone marrow comprising administering a compound as defined herein to a human in need of such treatment.

Example 1

In Vitro TK Inhibition Assays

Procedure

Experiments were performed using purified intracellular domain of c-kit expressed in baculovirus. Estimation of the kinase activity was assessed by the phosphorylation of tyrosine containing target peptide estimated by established ELISA assay.

Experimental Results on Tested Compounds

Result in Table 1 shows the potent inhibitory action of the catalytic activity of c-kit with an IC50<10 μM. Further experiments (not shown) indicates that at least one compound acts as perfect competitive inhibitors of ATP.

TABLE 1

| Compounds | In vitro Inhibition assay results c-kit IC50 (μM) |
|---|---|
| 066; 074; 078; 084; 012; 016; 073; 021; 088; 023; 025; 047; 048; 055; 049; 026; 087; 075; 089; 051; 082; 090; 060; 085; 052; 053; 096 | <10 μM |

Example 2

Ex Vivo TK Inhibition Assays

Procedures

C-Kit WT and Mutated C-Kit (JM) Assay

Proliferation Assays

Cells were washed two times in PBS before plating at 5×104 cells per well of 96-well plates in triplicate and stimulated either with hematopoietic growth factors (HGF) or without. After 2 days of culture, 37 Bq (1.78 Tbq/mmol) of [$_3$H] thymidine (Amersham Life Science, UK) was added for 6 hours. Cells were harvested and filtered through glass fiber filters and [$_3$H] thymidine incorporation was measured in a scintillation counter. For proliferation assay, all drugs were prepared as 20 mM stock solutions in DMSO and conserved at −80° C. Fresh dilutions in PBS were made before each experiment. DMSO dissolved drugs were added at the beginning of the culture. Control cultures were done with corresponding DMSO dilutions. Results are represented in percentage by taking the proliferation without inhibitor as 100%.

Cells

Ba/F3 murine kit and human kit, Ba/F3 mkitΔ27 (juxtamembrane deletion) are derived from the murine IL-3 dependent Ba/F3 proB lymphoid cells. The FMA3 and P815 cell lines are mastocytoma cells expressing endogenous mutated forms of Kit, i.e., frame deletion in the murine juxtamembrane coding region of the receptor-codons 573 to 579. The human leukaemic MC line HMC-1 expresses mutations JM-V560G;

Immunoprecipitation Assays and Western Blotting Analysis

For each assay, 5.10$_6$ Ba/F3 cells and Ba/F3-derived cells with various c-kit mutations were lysed and immunoprecipitated as described (Beslu et al., 1996), excepted that cells were stimulated with 250 ng/ml of rmKL. Cell lysates were immunoprecipitated with a rabbit immunserum anti murine KIT, directed against the KIT cytoplasmic domain (Rottapel et al., 1991). Western blot was hybridized either with the 4G10 anti-phosphotyrosine antibody (UBI) or with the rabbit immunserum anti-murine KIT or with different antibodies (described in antibodies paragraph). The membrane was then incubated either with HRP-conjugated goat anti mouse IgG antibody or with HRP-conjugated goat anti rabbit IgG antibody (Immunotech), Proteins of interest were then visualized by incubation with ECL reagent (Amersham).

Experimental Results

The experimental results for various compounds according to the invention using above-described protocols are set forth at Table 2:

TABLE 2

| Target | IC50 (μm) | Compounds |
|---|---|---|
| c-Kit WT | IC50 < 10 μM | 002; 005; 006; 007; 008; 009; 010; 012; 017; 019; 020; 021; 023; 024; 025; 026; 028; 029; 030; 032; 042; 043; 045; 047; 048; 049; 050; 051; 052; 053; 054; 055; 056; 057; 059; 060; 061; 062; 063; 064; 065; 066; 067; 072; 073; 074; 075; 077; 078; 079; 080; 081; 082; 083; 084; 085; 086; 087; 088; 089; 090; 092; 093; 094; 095; 096; 097; 106; 105; 104; 103; 128; 129; 130; 131; 117; 110; 116; 124; 108; 122; 111; 113; 118; 107; |
| c-Kit JM Δ27 | IC50 < 1 μM | 028; 074; 029; 009; 012; 073; 020; 042; 061; 065; 088; 025; 048; 049; 050; 089; 051; 082; 090; 083; 059; 052; 053; 066; 103; 067; 104; 078; 079; 105; 081; 084; 030; 010; 021; 043; 054; 062; 106; 023; 024; 064; 047; 055; 026; 087; 075; 085; 005; 077; 092; 060; 032; 017; 063; 093; 094; 095; 086; 093; 096; 108; 117; 122; 008; 080; 111; 118; 113; 007; 072; 019; 056; 057; 107; 097; |

Example 3

In Vivo Activity

Procedures
GIST
cells: Ba/F3 cells were transfected by c-kit gene having Δ27 mutation (GIST model). Ba/F3 expressing the mutated c-kit gene readily proliferate in the absence of IL3 or SCF and are tumorigenic in nude mice.
Protocol:
Mice were irradiated at J-1 (5 Gy)
Tumor cells ($10^6$) were subcutaneously grafted at Jo
Tumor size were daily measured from J14
Number of survival mice were daily estimated
In this experimental model, the tumor size at J14 is about 20 $mm^3$
Treated mice received per os twice a day a dose of 100 mg/kg of one compound of formula II-3 during 5 days (from J26 to J30).

Rheumatoid Arthritis
The mice were pretreated with the compound of formula II-3 (2×, 12.5 mg/kg) for two days (day −2, day −1) before induction of arthritis. Arthritis was induced by ip injection of 150-ul serums at days 0 and 2. The treatment with the compound (2×, 12.5 mg/kg) was continued for 14 days. The control mice were injected with, 1% PBS before the induction of arthritis and during the course of the disease. Ankle thickness and arthritis score was evaluated for 15 days. Arthritis Score: Sum of scores of each limb (0 no disease; 1 mild swelling of paw or of just a few digits; 2 clear joint inflammation; 3 severe joint inflammation) maximum score=12. Table 3A and Table 3B show the number of mice used in this study. Two sets of experiments were done with different number of mice, one with 4 mices the other with 8 mices.

TABLE 3A

| Treated Mice | C57B1/6 |
|---|---|
| 2×, 12.5 mg/Kg | 6 |

TABLE 3B

| Controls | C57B1/6 |
|---|---|
| 2×, 1% PBS | 6 |

Histology
At the end of the experiment the hind limbs were collected. The skin of the limb was removed and the limbs were subsequently fixed in 2% Para formaldehyde.
Experimental Results
GIST
Treated mice (with one compound of formula II-3) displays significant decrease of tumor size at J30 and J33 compared to control.
When administrated per os, one tested compound of the formula II-3 displays a significant antitumor activity against tumors cells expressing c-kit Δ27.
RA
A compound of the formula II-3 has demonstrated significant activity in the in vivo mouse model of arthritis. Results are shown on FIGS. 1, 2, 3, 4.

FIGURE LEGENDS

FIG. 1: Effect of the compound in serum transfer experiments, Protocol, ip daily treatment with the compound (2×12.5 mg/kg) and on days −2 and −1, set of experiment with 4 mices (T: treated, C: control)

Figure 2:
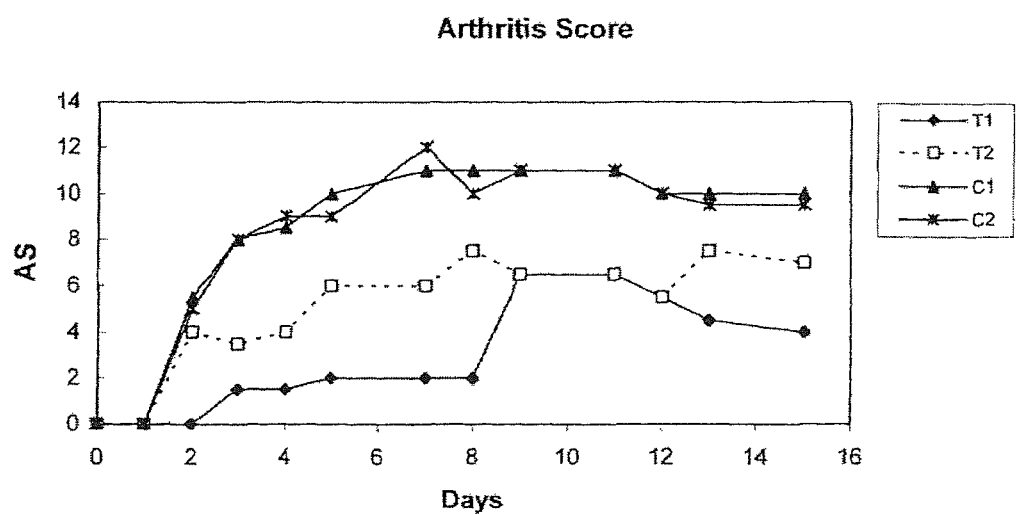

FIG. 2: Effect of the compound in serum transfer experiments, Protocol, ip daily treatment with the compound (2×12.5 mg/kg) and on days −2 and −1, set of experiment with 4 mices (T: treated, C: control)

Figure 3:
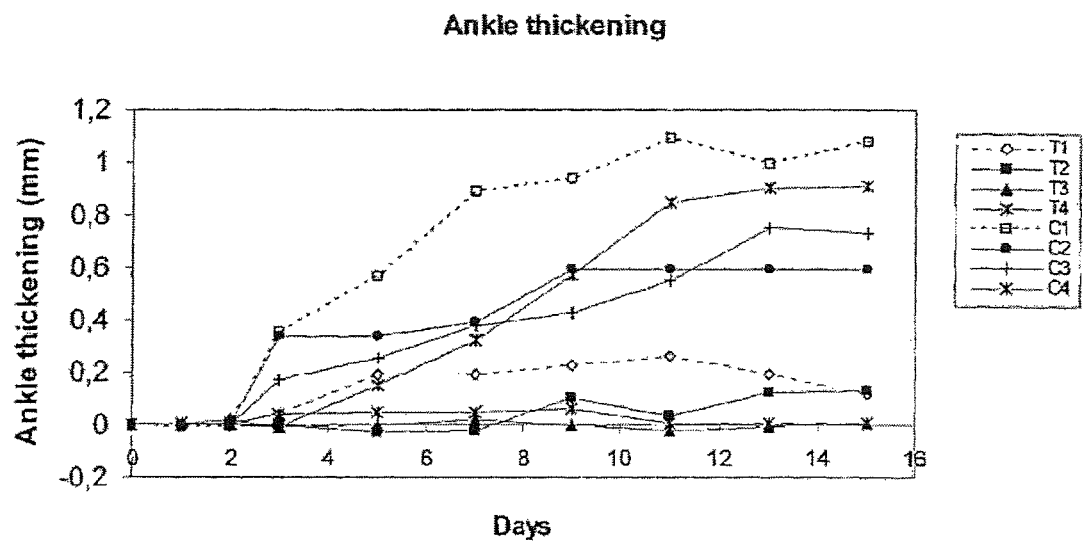

FIG. 3: Effect of the compound in serum transfer experiments, Protocol, ip daily treatment with the compound (2×12.5 mg/kg) and on days −2 and −1, set of experiment with 8 mices (T: treated, C: control)

Figure 4:
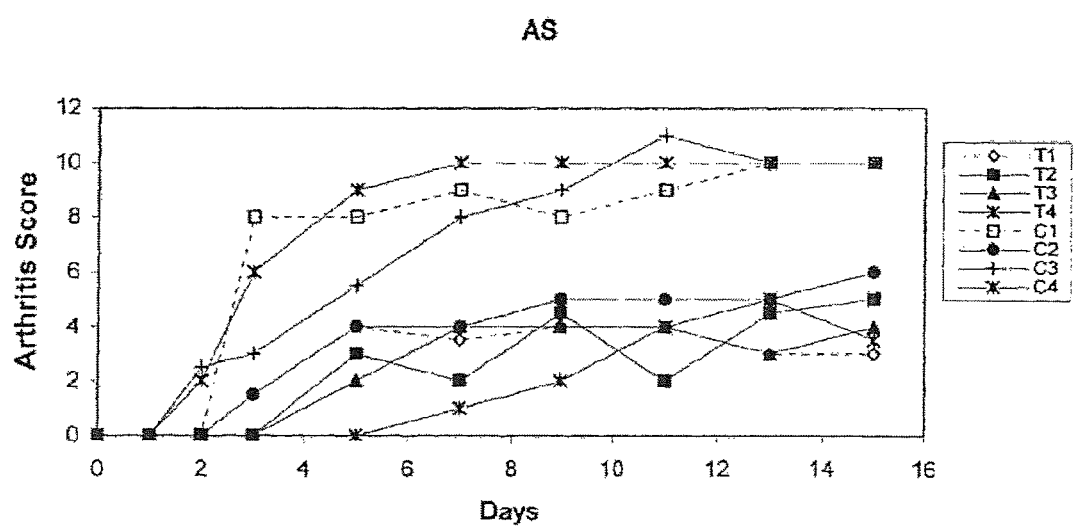

FIG. 4: Effect of the compound in serum transfer experiments, Protocol, ip daily treatment with the compound (2×12.5 mg/kg) and on days −2 and −1, set of experiment with 8 mices (T: treated, C: control)

The invention claimed is:
1. A pharmaceutical composition comprising a compound of the formula:

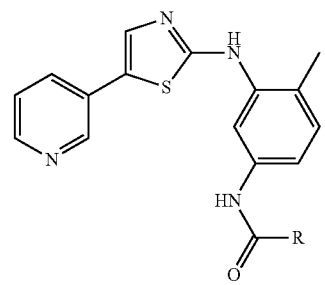

wherein R is:
H or a linear or branched alkyl group containing from 1 to 10 carbon atoms optionally substituted with at least one substituent selected from the group consisting of halogen and a pendant basic nitrogen functionality; or
a cycloalkyl, an aryl or heteroaryl group optionally substituted with at least one substituent selected from the group consisting of halogen and a pendant basic nitrogen functionality; or
a cycloalkyl, an aryl or heteroaryl group substituted by an alkyl, a cycloalkyl, an aryl or heteroaryl group optionally substituted with at least one substituent selected from the group consisting of halogen and a pendant basic nitrogen functionality;

wherein said pendant basic nitrogen functionality is selected from the group consisting of

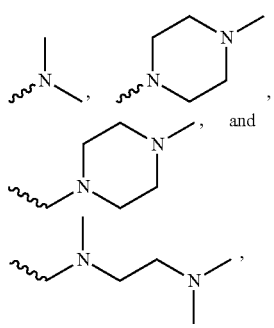

wherein the wavy line corresponds to the point of attachment;
and one or more pharmaceutically acceptable carriers.

2. The pharmaceutical composition of claim 1, which is an oral composition.

3. The pharmaceutical composition of claim 1, which is an aerosol composition.

4. The pharmaceutical composition of claim 1, which is a topical composition.

5. An oral pharmaceutical composition comprising 4-(4-methyl-piperazin-1-ylmethyl)-N-[4-methyl-3-(4-pyridin-3-yl-thiazol-2-ylamino)-phenyl]-benzamide:

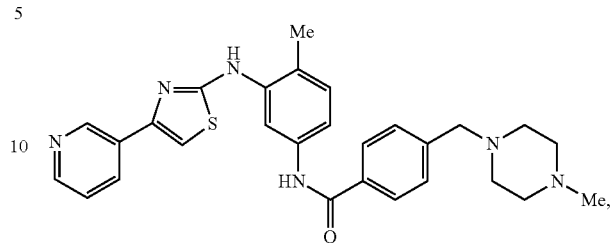

and one or more pharmaceutically acceptable carriers.

6. The oral pharmaceutical composition of claim 5, which is in the form of a tablet, a pill, a dragee, a capsule, a liquid, a gel, a syrup, a slurry or a suspension.

7. The oral pharmaceutical composition of claim 6, which is in the form of a tablet.

8. The oral pharmaceutical composition of claim 6, which is in the form of a capsule.

9. The oral pharmaceutical composition of claim 6, which is in the form of a liquid.

10. The oral pharmaceutical composition of claim 6, which is in the form of a suspension.

* * * * *